United States Patent
Hayakawa et al.

(10) Patent No.: US 9,788,745 B2
(45) Date of Patent: Oct. 17, 2017

(54) BIOLOGICAL SIGNAL MEASURING EQUIPMENT

(75) Inventors: Tomohiro Hayakawa, Saitama (JP); Haruhiko Soma, Tokyo (JP); Seiji Wada, Kanagawa (JP); Fan Wang, Tokyo (JP); Natsuki Kimura, Tokyo (JP); Mitsuhiro Nakamura, Kanagawa (JP); Shiko Yamashita, Tokyo (JP); Yusaku Nakashima, Tokyo (JP); Takuro Yamamoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 1002 days.

(21) Appl. No.: 13/379,954

(22) PCT Filed: Jun. 28, 2010

(86) PCT No.: PCT/JP2010/061361
§ 371 (c)(1),
(2), (4) Date: Jan. 25, 2012

(87) PCT Pub. No.: WO2011/002092
PCT Pub. Date: Jan. 6, 2011

(65) Prior Publication Data
US 2015/0133762 A1    May 14, 2015

(30) Foreign Application Priority Data

Jun. 29, 2009  (JP) ................................. 2009-153985
Oct. 23, 2009  (JP) ................................. 2009-244875
Jun. 21, 2010  (JP) ................................. 2010-140712

(51) Int. Cl.
*A61B 5/0478*    (2006.01)
*A61B 5/0496*    (2006.01)
(Continued)

(52) U.S. Cl.
CPC ........ *A61B 5/0478* (2013.01); *A61B 5/04012* (2013.01); *A61B 5/0488* (2013.01);
(Continued)

(58) Field of Classification Search
CPC ................ A61B 5/0476; A61B 5/0478; A61B 5/0482–5/04847; A61B 5/4058;
(Continued)

(56) References Cited

U.S. PATENT DOCUMENTS 2,426,958 A  *  9/1947  Ulett, Jr. et al. .............. 600/383
4,189,788 A  *  2/1980  Schenke .............. H04R 1/1066
                                                      2/209
(Continued)

FOREIGN PATENT DOCUMENTS

CN         1909828      2/2007
JP         51-002454    1/1976
(Continued)

OTHER PUBLICATIONS

Japanese Patent Office, Notification of Reason(s) for Refusal issued in connection with Japanese Patent Application No. 2010-140711, dated Apr. 1, 2014. (7 pages).
(Continued)

*Primary Examiner* — Lee S Cohen
*Assistant Examiner* — Erin M Cardinal
(74) *Attorney, Agent, or Firm* — Chip Law Group

(57) ABSTRACT

A biological signal measuring equipment used in a measurement of a biological signal in a head portion, has a jaw contact portion that comes into contact with a forehead; an occiput contact portion that comes into contact with an occiput; and a supporter that is interposed in a front and rear direction of the head portion and is supported by the head portion by using the jaw contact portion and the occiput contact portion as ends. The biological signal measuring
(Continued)

equipment performs the measurement in the same manner as the case of measuring a wave motion of a short period, even in the case of measuring the wave motion of a long period generated in a head portion.

8 Claims, 50 Drawing Sheets

(51) Int. Cl.
 *A61B 5/00* (2006.01)
 *A61B 5/04* (2006.01)
 *A61B 5/0488* (2006.01)
(52) U.S. Cl.
 CPC .......... *A61B 5/0496* (2013.01); *A61B 5/4806* (2013.01); *A61B 5/4815* (2013.01); *A61B 5/6814* (2013.01); *A61B 5/6887* (2013.01)
(58) Field of Classification Search
 CPC ... A61B 5/4064; A61B 5/4076–5/4094; A61B 5/4806–5/4821; A61B 5/6801; A61B 5/6803; A61B 5/6814; A61B 5/6831; A61B 5/6839; A61B 2560/04; A61B 2560/0406; A61B 2560/0468; A61B 2562/0209; A61B 2562/14
 USPC ................. 600/372, 382, 383, 390, 544–545
 See application file for complete search history.

(56) References Cited

U.S. PATENT DOCUMENTS

| | | | | |
|---|---|---|---|---|
| 4,928,696 | A * | 5/1990 | Henderson et al. | 600/383 |
| 5,479,934 | A * | 1/1996 | Imran | 600/544 |
| 6,077,237 | A * | 6/2000 | Campbell | G06F 3/011 600/587 |
| 6,154,669 | A * | 11/2000 | Hunter et al. | 600/383 |
| 8,392,251 | B2 * | 3/2013 | Pradeep et al. | 705/14.41 |
| 8,692,677 | B2 * | 4/2014 | Wada et al. | 340/575 |
| 8,734,343 | B2 * | 5/2014 | Lin | A61B 5/11 600/300 |
| 2002/0188216 | A1 * | 12/2002 | Kayyali | A61B 5/04085 600/544 |
| 2005/0107716 | A1 * | 5/2005 | Eaton et al. | 600/544 |
| 2007/0093706 | A1 * | 4/2007 | Gevins et al. | 600/383 |
| 2007/0167850 | A1 | 7/2007 | Russell et al. | |
| 2009/0024017 | A1 * | 1/2009 | Ruffini et al. | 600/395 |
| 2009/0112077 | A1 * | 4/2009 | Nguyen et al. | 600/383 |
| 2010/0217103 | A1 * | 8/2010 | Abdul-Hafiz | A61B 5/14552 600/322 |
| 2011/0004089 | A1 * | 1/2011 | Chou | 600/383 |
| 2011/0015503 | A1 * | 1/2011 | Joffe et al. | 600/301 |
| 2011/0098593 | A1 * | 4/2011 | Low et al. | 600/544 |
| 2012/0143020 | A1 * | 6/2012 | Bordoley et al. | 600/301 |
| 2012/0253159 | A1 * | 10/2012 | Medina | A61B 5/14552 600/340 |
| 2013/0172721 | A1 * | 7/2013 | McPeck et al. | 600/383 |
| 2014/0276183 | A1 * | 9/2014 | Badower | A61B 5/0476 600/544 |

FOREIGN PATENT DOCUMENTS

| | | |
|---|---|---|
| JP | 52-093190 | 8/1977 |
| JP | HEI 3-16905 | 2/1991 |
| JP | HEI 5-261076 | 10/1993 |
| JP | 2001-340312 | 12/2001 |
| JP | 2002-301038 | 10/2002 |
| JP | 2005-152415 | 6/2005 |
| JP | 2006-006666 | 1/2006 |
| JP | 2006-094979 | 4/2006 |
| JP | 2009-078139 | 4/2009 |
| JP | 2010-051356 | 3/2010 |
| WO | 00/45701 | 8/2000 |
| WO | 2004/112604 | 12/2004 |
| WO | 2007/109745 A2 | 9/2007 |
| WO | 2008/098346 | 8/2008 |

OTHER PUBLICATIONS

Japanese Patent Office, Notification of Reason(s) for Refusal issued in connection with Japanese Patent Application No. 2010-140712, dated Apr. 1, 2014. (7 pages).

State Intellectual Property Office of PRC, Notification of the First Office Action issued in connection with PRC application No. 201080027985.7, dated Apr. 3, 2014. (13 pages).

State Intellectual Property Office of People's Republic of China, Notification of the First Office Action issued in connection with application No. 201080027987.6, dated Jul. 18, 2013. (14 pages).

* cited by examiner

FIG. 39
(C)
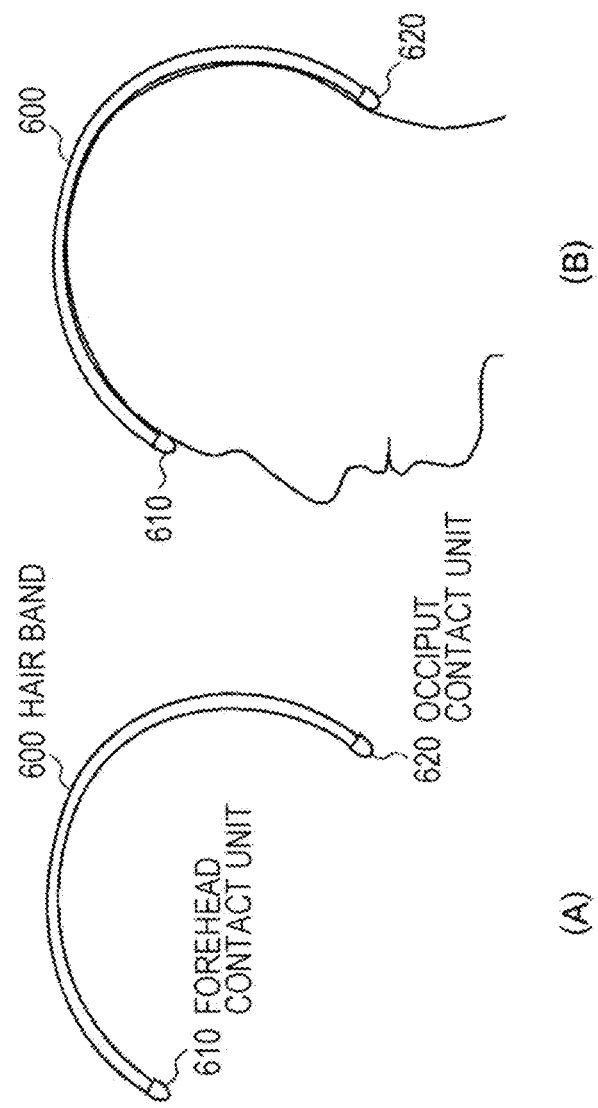
(B)
600 HAIR BAND
610 FOREHEAD CONTACT UNIT
620 OCCIPUT CONTACT UNIT
(A)

FIG. 45
(A) 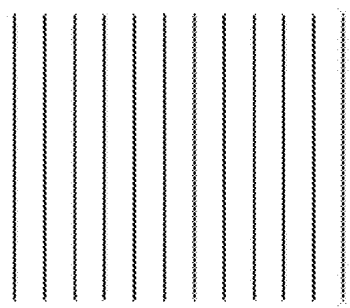
(B) 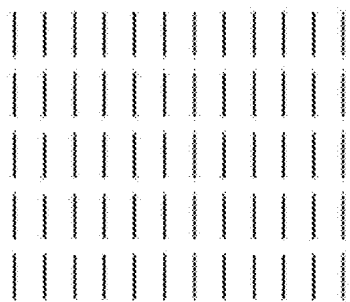
(C) 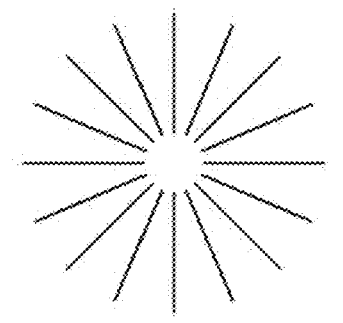

BIOLOGICAL SIGNAL MEASURING EQUIPMENT

CROSS REFERENCE TO RELATED APPLICATIONS

The present application is a National Stage of International Application No. PCT/JP2010/061361 filed on Jun. 28, 2010, which claims priority to Japanese Patent Application No. 2010-140712, filed in the Japanese Patent Office on Jun. 21, 2010; Japanese Patent Application No. 2009-153985, filed in the Japanese Patent Office on Jun. 29, 2009; and Japanese Patent Application No. 2009-244875, filed in the Japanese Patent Office on Oct. 23, 2009, the entire contents of which are being incorporated herein by reference

BACKGROUND

The present invention relates to biological signal measuring equipment and is suitable for a technical field that acquires a wave motion generated and transmitted in vivo as an electric signal or the like.

It is apparent that a decline in quality or amount (time) of a sleep increases a risk of various lifestyle diseases such as circulatory system diseases such as a myocardial infarction or a cerebral infarction, and endocrine diseases such as diabetes. Furthermore, an extension of REM (Rapid Eye Movement) sleep or a drop of density is strongly suspected as a cause of depression. In this manner, sleep relates to many diseases or social problems faced by modern man, and evaluating the quality of sleep is set to be further important in the future.

As a method of evaluating sleep, a sleep polygraph examination is known. However, in the sleep polygraph examination, a restriction period of a subject in an examination facility such as a hospital is long, and there are many attachments to a subject, and thus, there is a problem in that an excessive burden is imposed on a subject.

Meanwhile, a device is suggested which measures a sleep cycle from a heart beat or a parameter required for the evaluation of the quality of the sleep without taking brainwaves (for example, PTL 1). In the device, compared to the sleep polygraph examination, the burden on the subject is reduced, but the parameter required for the evaluation of the quality of the sleep is an indirect assumption consistently.

On the other hand, as the measurement of the brainwaves that are the direct parameter evaluating the quality of sleep, a headphone type (for example, PTL 2), a cap type (for example, PTL 3), and a headset type (for example, PTL 4) brainwave measuring device are suggested.

CITATION LIST

Patent Literature

PTL 1: Japanese Unexamined Patent Application Publication No. 2009-078139
PTL 2: Japanese Unexamined Patent Application Publication No. 2001-340312
PTL 3: Japanese Unexamined Patent Application Publication No. 2006-006666
PTL 4: Japanese Unexamined Patent Application Publication No. 2010-051356

SUMMARY

However, in the brainwave measuring devices of PTL 2 to PTL 4, a blood vessel, a lymph or the like can be tightly fastened. Thus, in the case of measuring the brainwave of a long period such as the brainwaves of the sleep state, the tightening itself is not only a burden on a subject, but a physiological phenomena due to the tightening also affects the brainwaves, whereby it is difficult to obtain a correct measurement value.

The present invention provides biological signal measuring equipment that can perform the measurement in the same manner as the case of measuring the wave motion of a short period, even in the case of measuring the wave motion of a long period generated in a head portion.

In order to solve the problem, according to the present invention, there is provided a biological signal measuring equipment used in the measurement of the biological signal in a head portion, which has a jaw contact portion that comes into contact with a forehead, an occiput contact portion that comes into contact with the occiput, and a supporter that is interposed in a front and rear direction of the head portion and is supported by the head portion by using the jaw contact portion and the occiput contact portion as ends.

On the head portion surface, near the median sagittal plane, nerves, a blood vessel system, a lymphatic system, and a muscular system are generally not interposed. In the present invention, since the supporter supported by a head portion can be interposed in the front and rear direction of the head portion by using the jaw contact portion and the occiput contact portion as ends, the oppression of the nerves, the blood vessel system, the lymphatic system, and the muscular system due to the self weight of the interposition or the supporter is greatly relieved compared to a head brace such as a headphone type or a cap type.

Thus, even in a case where a long period measurement is required, a variation (migraine, discomfort or the like) of the physiological phenomena due to the oppression (mounting) is suppressed.

In this manner, a biological signal measuring equipment is realized in which the measurement can be performed in the same manner as the case of measuring the wave motion of a short period, even in the case of measuring the wave motion of the long period generated in the head portion.

Additional features and advantages of the present invention are described herein, and will be apparent from, the following Detailed Description and Figures.

BRIEF DESCRIPTION OF THE FIGURES

FIGS. 39A to 39C are diagrams that schematically show a hair band and a mounting state thereof in another embodiment.

FIGS. 45A to 45C are diagrams that schematically show an arrangement of an electrode in another embodiment.

DETAILED DESCRIPTION

Hereinafter, embodiments for carrying out the present invention will be described. In addition, the description will be made in the sequence as below.

<1. First Embodiment>
[1-1. Configuration of Biological Signal Measuring Equipment]
[1-2. Mounting Sequence]
[1-3. Configuration of Measurement Portion]
<2. Second Embodiment>
[2-1. Configuration of Biological Signal Measuring Equipment]
[2-2. Mounting Sequence]
<3. Third Embodiment>
[3-1. Configuration of Biological Signal Measuring Equipment]
[3-2. Mounting Sequence]
[3-3. Configuration of Measurement Portion]
<4. Another Embodiment>

1. First Embodiment 1-1. Configuration of Biological Signal Measuring Equipment

Figure 1:
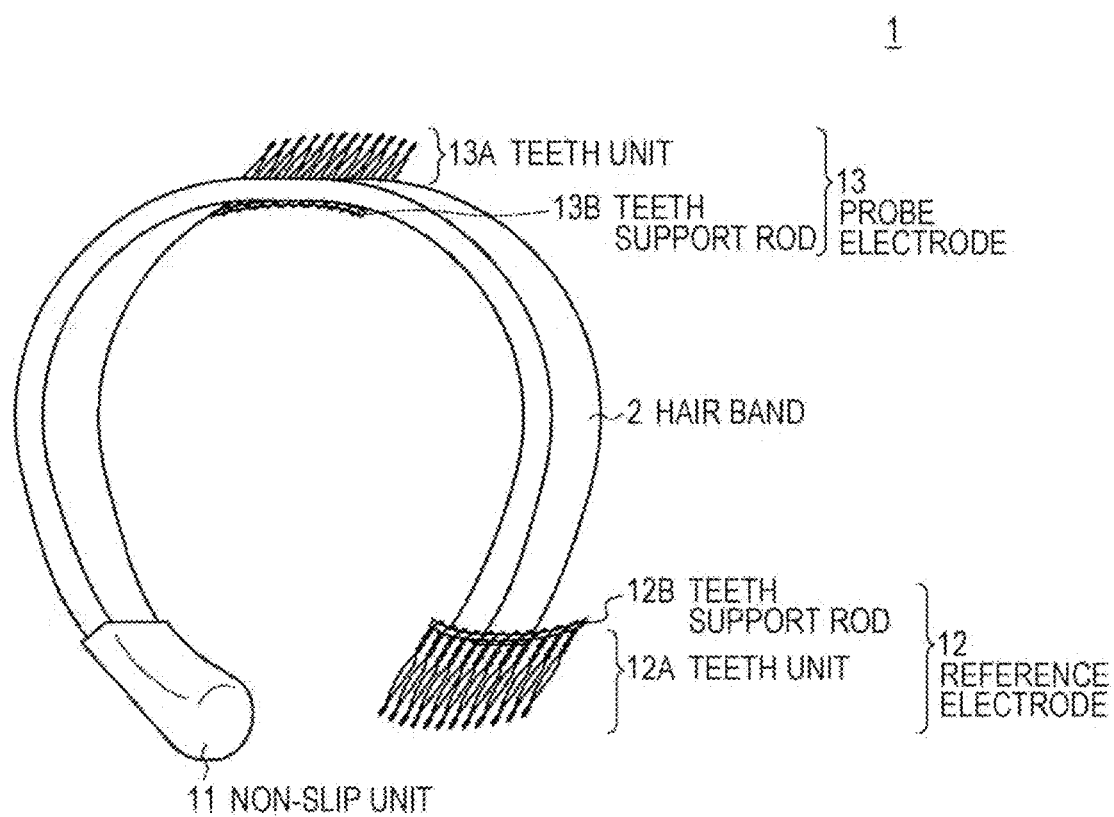
FIG. 1 is a diagram that schematically shows a configuration of biological signal measuring equipment in a first embodiment.

FIG. 1 shows a configuration of a biological signal measuring equipment 1. The biological signal measuring equipment 1 has a supporter (hereinafter, referred to as a hair band) 2 that can be supported on a hair portion. The hair band 2 is a plastic material or a metallic material of a plate shape having elasticity and is formed in a C shape.

One end of the hair band 2 is provided with a non-slip portion 11 formed of rubber or the like. The non-slip portion 11 has a curved shape at a tip thereof and is configured so that an inroad into the head portion can be prevented.

Figure 2:
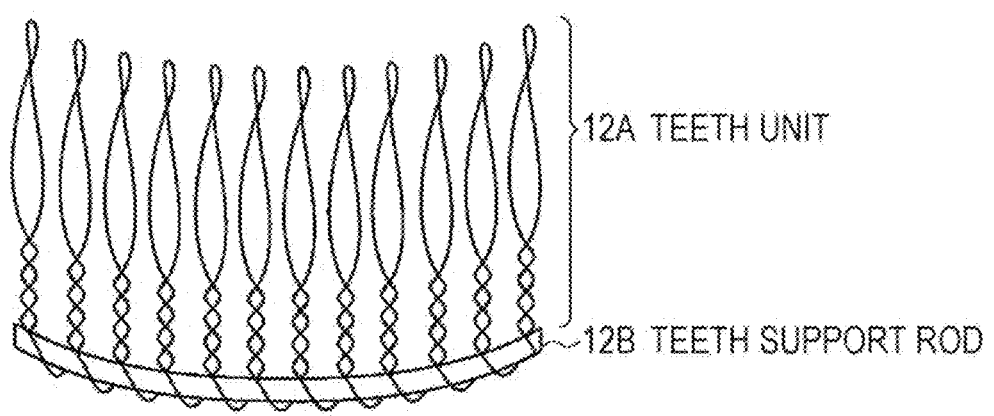
FIG. 2 is a diagram that schematically shows a configuration of a reference electrode.

Meanwhile, the other end of the hair band 2 is provided with a reference electrode 12. As shown in FIG. 2, the reference electrode 12 includes a portion (hereinafter, also referred to as a teeth portion) 12A in which a plurality of teeth formed of a conductor is aligned in a row, and a rod-like portion (hereinafter, also referred to as a teeth support rod) 12B that supports the teeth portion 12A.

The teeth of the teeth portion 12A is formed of a conductive line material, a teeth tip side is formed in a tubular shape from a predetermined position between the center thereof and the root thereof, the root sides are wound in a reverse direction in the state of contacting each other from the predetermined position, are formed in a rod shape, and are fixed to the teeth support rod 12B while maintaining equal distance with the adjacent teeth.

The teeth support rod 12B is formed of an inflexible conductor thicker than the line material of the teeth portion 12A and is attached so that each tooth tip of the teeth portion 12A faces in the same direction of facing from the center to the tip of the hair band 2. Furthermore, the teeth support rod 12B is curved to the non-slip portion 11 side of the hair band 2 so as to make the shape of the head side.

Meanwhile, the center of the hair band 2 is provided with a probe electrode 13. The probe electrode 13 includes a teeth portion 13A and a teeth support rod 13B having the same structures as the reference electrode 12. The teeth support rod 13B is attached such that each tooth tip of the teeth portion 13A faces in a direction perpendicular to the direction facing the center to the tip on the surface of the curved apex portion in the hair band 2 in the center portion of the hair band 2.

1-2. Mounting Sequence

Next, a mounting sequence of the biological signal measuring equipment 1 will be described. In a first step, a back surface of the hair band 2 is covered until coming into contact with a portion between the vertex and forehead. Since the hair band 2 is formed in a C shape having elasticity (see FIG. 1), the head portion can be interposed in the state in which a predetermined pressure is applied in a direction in which both ends approach each other. Thus, a position deviation of the hair band 2 itself to the head portion is reduced.

Meanwhile, the reference electrode 12 provided in the other end of the hair band 2 is attached such that each tooth tip of the teeth portion 12A faces in the same direction as the direction facing from the center to the tip of the hair band 2, and the teeth portion 12A has a structure in which a plurality of teeth is aligned in a row (see FIG. 1). For this reason, the hair band 2 can smoothly insert the teeth to the root of the hair when being covered on the head portion.

The teeth tip side is formed by the line material in a tubular shape from a predetermined position of the center and the root of the teeth in the teeth portion 12A (see FIG. 2). For this reason, each tooth in the hair band 2 is entangled in the hair root, whereby the adhesion of the teeth to the scalp is improved compared to the point contact and the position deviation can be reduced. In addition, the pain to a subject is relieved, and the mounting comfort can be improved.

In a second step, the hair band 2 in the state of coming into contact with a portion between the vertex and the forehead slides in a vertex position. The probe electrode 13 provided in the center of the hair band 2 is attached such that each tooth tip of the teeth portion 13A faces in a direction perpendicular to the direction facing from the center to the tip on the surface of the curved apex portion in the hair band 2 (see FIG. 1). For this reason, the hair band 2 can smoothly insert the teeth to the root of the hair when sliding to the vertex position.

Furthermore, the teeth tip side is formed by the line material in a tubular shape from a predetermined position between the center and the root of the teeth in the teeth portion 13A (see FIG. 2). For this reason, each tooth in the hair band 2 is entangled in the hair root, whereby the adhesion to the scalp is improved compared to the case of the point contact, and the position deviation can be reduced.

Figure 3:
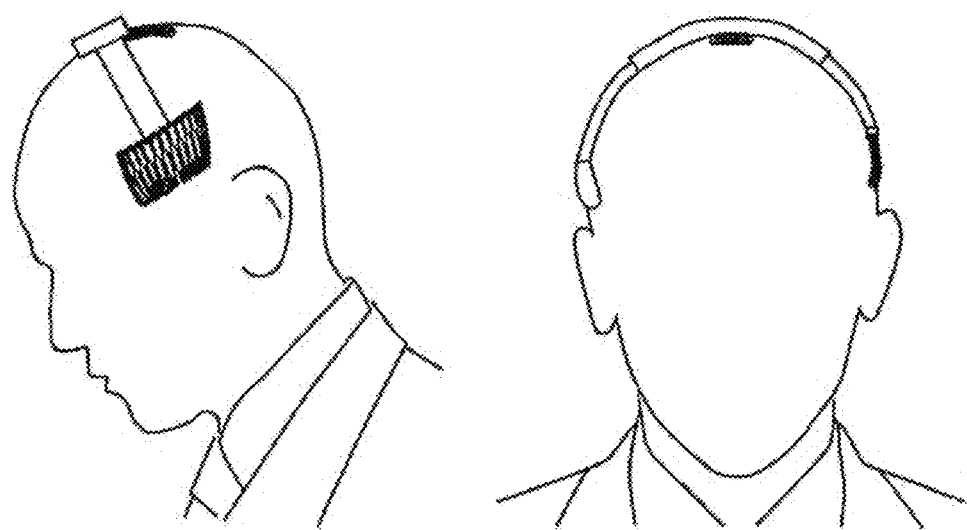
FIG. 3 is a diagram that schematically shows a mounting state of the biological signal measuring equipment.

By going though the mounting sequence as mentioned above, for example, as shown in FIG. 3, the biological signal measuring equipment 1 is mounted on the head portion, and the reference electrode 12 and the probe electrode 13 are fixed to the scalp.

The reference electrode 12 is an electrode in which a plurality of teeth having a line shape is arranged in a row, and thus the thickness thereof is extremely thin. Thus, even when situated between the pillow, it is possible to reduce the discomfort due to the presence of the reference electrode 12. Meanwhile, since the vertex, where the probe electrode 13 is situated is a part in which the contact with the pillow is nearly avoided even when rolling over during normal sleep, it is possible to reduce the discomfort due to the presence of the probe electrode 13.

Furthermore, among the teeth portions 12A and 13A in the reference electrode 12 and the probe electrode 13, the root side is wound in the reverse direction in the state coming into contact with each other from a predetermined position between the center and the root and is fixed to the teeth support rod 12B as a rod shape (see FIG. 2). That is, since each tooth of line shape is fixed to the teeth support rod 12B at one point, each tooth can equally be moved around the fixing point, respectively. For this reason, even if force is applied from any direction due to turning over or the like, it is possible to flexibly respond to the force, and when the force is dissipated, an original state can rapidly be returned to.

Thus, the biological signal measuring equipment 1 can greatly reduce the sleep inhibition on a subject. Furthermore, compared to the sleep polygraph examination in which a plurality of mounts spreads over the subject, it is possible to relieve the burden on a subject without losing the mounting on a subject.

In addition, the electrode 12 and 13 in the biological signal measuring equipment 1 are supported by the hair band 2. Thus, the biological signal measuring equipment 1 can prevent that the electrode is dropped during attachment and detachment and can put the wiring to be connected to the electrodes 12 and 13 into the hair band 2. As a result, the biological signal measuring equipment 1 can avoid missing electrodes during attachment and detachment or the entanglement in to cord, whereby the usability can be improved.

In addition, the sequence of the mounting mentioned above is merely an example but not limited to the sequence of the mounting.

1-3. Configuration of Measurement Portion

Figure 4:
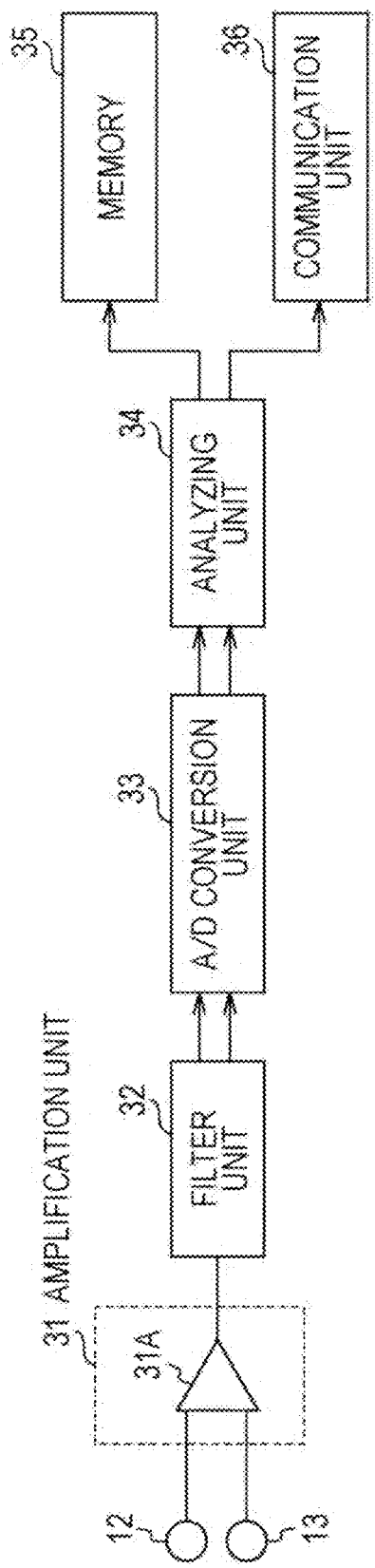
FIG. 4 is a diagram that schematically shows a circuit configuration of a measurement portion.

FIG. 4 shows a configuration of a measurement portion that measures the biological signal to be sensed by the reference electrode 12 and the probe electrode 13. A circuit substrate or the like in the measurement portion is, for example, provided on the surface or the inner portion of the hair band 2.

The measurement portion 30 has a configuration that includes an amplification portion 31, a filter portion 32, A (Analog)/D (Digital) conversion portion 33, an analyzing portion 34, a memory 35, and a communication portion 36.

The measurement portion 30 supplies a power source voltage of a battery or the like to the respective portions 31 to 36, for example, when receiving the measurement start command from an operation portion provided on the surface of the hair band 2, and shuts off the supply of the power source when receiving a measurement stop command from the operation portion.

The amplification portion 31 has a differential amp 31A. The differential amp 31A amplifies a potential difference between the reference electrode 12 and the probe electrode 13 as a signal (hereinafter, also referred to as a biological wave form signal), and outputs the amplified biological signal to a filter portion 32. Since the probe electrode 13 is an electrode provided in a vertex position, the biological wave form signal to be output from the differential amp 31A is mainly a signal in which brainwaves are reflected.

As mentioned above, since the reference electrode 12 and the probe electrode 13 have the structure in which the position deviation is reduced while the adhesion of the teeth portions 12A and 13A to the scalp is improved, even if the electrode is not bonded to the scalp by the paste, the amplification portion 13 can accurately amplify the potential difference, and as a result, the sensitivity in the measurement portion is improved.

In addition, a head side position, where the reference electrode 12 is situated and a vertex position, where the probe electrode 13 is situated, are a position on a skull. Thus, a muscle potential component is reduced in the biological wave form signal obtained from the reference electrode 12 and the probe electrode 13, whereby the sensitivity to brainwaves is improved.

A frequency band corresponding to the brainwaves is set in the filter portion 32. The filter portion 32 removes the signal components other than the set frequency band from the biological wave form signal, and gives the A/D conversion portion 33 the removed biological wave form signal.

In addition, the brainwaves include a delta wave (1 to 3 (Hz)), a theta wave (4 to 7 (Hz)), an alpha wave (8 to 13 (Hz)), a beta wave (14 to 30 (Hz)), a gamma wave (31 to 64 (Hz)), an omega wave (65 to 128 (Hz)), a rho wave (129 to 512 (Hz)), and a sigma wave (513 to 1024 (Hz)), but a part or all of them are set so as to be changeable by a predetermined operation portion as the frequency band corresponding to the brainwaves.

The A/D conversion portion 33 converts the biological wave form signal into digital data (hereinafter, also referred to as biological wave form data) and gives the analyzing portion 34 the biological wave form data.

The analyzing portion 34 has a configuration that includes a CPU, a ROM, and a RAM as a work memory of the CPU, a speaker, and a clock (a time piece portion). In the ROM, a program for executing the analyzing treatment, a data indicating a level (hereinafter, referred to as a non-contact level threshold value) at which the electrode does not come into contact with the human body surface or the like is memorized.

The analyzing portion 34 develops the program stored in the ROM to the RAM when receiving the measurement start command, and executes the treatment (hereinafter, also referred to as an electrode contact detection treatment) that analyzes the presence or the absence of the contact of the electrode and the wave form analyzing treatment according to the program.

An example of the specific treatment content of the electrode contact analyzing treatment will be described. The analyzing portion 34 compares an average of the level in the biological wave form data for each regulation period with the non-contact level threshold value to be set to the average.

When the level average is lower than the non-contact level threshold value, the analyzing portion 34 decides that the electrode has not come into contact with the human body surface, stops the treatment, and notifies that the electrode needs to be remounted via a speaker.

On the other hand, when the level average exceeds the non-contact level threshold value, the analyzing portion 34 decides that the electrode comes into contact with the human body surface, and memorizes the biological wave form data in the regulation period in the memory 35.

In this manner, the electrode contact analyzing treatment is executed. However, the treatment content is an example to the last.

Next, an example of a specific treatment content of the wave form analyzing treatment will be described. That is, the analyzing portion 34 recognizes each component of the brainwave wave form, the eye potential, and the muscle potential wave form from the biological waveform data as a first step.

As mentioned above, since the head side position, where the reference electrode 12 is situated, and the vertex position, where the probe electrode 13 is situated, are a position on the skull, the muscle potential component is reduced in the biological wave form signal. Furthermore, in general, when electrode is not bonded to the scalp using paste, the wave form level of the biological wave form signal is decreased. However, in the spectrum of the biological wave form data, it is confirmed that the respective components of the brainwave wave form, the eye potential wave, and the muscle potential wave form can be obtained.

The analyzing portion 34 determines a sleep onset time using the brainwave wave form and the eye potential wave form as a second step. Specifically, a point of time satisfying a condition, in which an α wave is dissipated and SEM (Slow Eye Movement) occurs, is considered as the sleep onset time.

The analyzing portion 34 performs various determinations concerning the sleep by the use of the brainwave wave form, the eye potential wave, and the muscle potential wave form as a third step. In the present embodiment, determinations of depth and quality of a non-REM sleep, and determinations of starting time, ending time and quality of the REM sleep are performed.

The determinations of the depth and the quality of the non-REM sleep are performed by the use of the number of occurrences (density of occurrences) of δ waves per unit time and an amplitude value of the δ wave.

Meanwhile, the determination of the starting time of the REM time is a point of time satisfying a condition in which the δ waves are dissipated, REM occurs, and the muscle potential is dissipated, and the determination of the ending time of the REM sleep is a point of time satisfying a condition in which the REM is dissipated and the muscle potential occurs.

On the other hand, the determination of the quality of the REM sleep is performed by the use of the number of occurrences (the occurrence density) of the REM per unit time from the starting time to the ending time of the REM sleep.

The analyzing portion 34 determines a waking time by the use of the brainwave wave form and the muscle potential wave form as a fourth step. Specifically, a point of time satisfying a condition, in which the β wave occurs and the muscle potential occurs, is the waking time.

The analyzing portion 34 determines the cycle pattern by the use of the number of occurrence of the non-REM sleep and the REM sleep, a ratio thereof, an occurrence cycle or the like as a fifth step.

The analyzing portion 34 creates the determination results in each step and the parameters (determination elements) used in the determination as data (hereinafter, also referred to as determination result data) as a sixth step, and memorizes the same in the memory 35 in association with the biological wave form data.

In this manner, the wave form analyzing treatment is executed. However, the treatment content is merely an example.

The memory 35 is configured so as to execute the writing or the reading according to the command given from the analyzing portion 34 or the communication portion 36. In addition, the memory 35 an apply a removable memory such as a USB memory, a SD card memory or a CF card memory without being limited to the built-in the measurement portion 3.

When a transmission command is given from the operation portion, the communication portion 36 transmits various data memorized in the memory 35 to a predetermined external device, for example, a radio communication.

2. Second Embodiment

2-1. Configuration of Biological Signal Measuring Equipment

Figure 5:
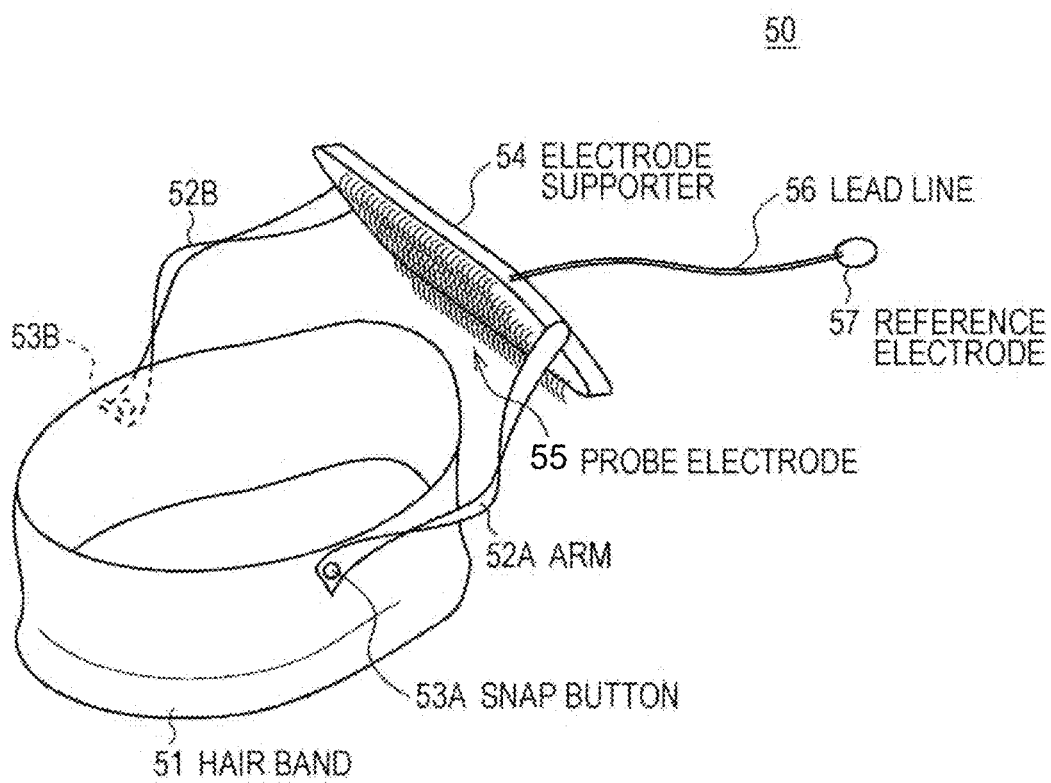
FIG. 5 is a diagram that schematically shows a configuration of the biological signal measuring equipment in a second embodiment.

In FIG. 5, a configuration of the biological signal measuring equipment 50 is shown. The biological signal measuring equipment 50 has a supporter (hereinafter, also referred to as a hair band) 51 that can be supported on a head portion. The hair band 51 is formed in a cloth material or a rubber material and is formed in a band shape or a ring shape.

At the opposite position of the hair band 51, a plate-shaped or a line-shaped arm 52 (52A and 52B) formed of a material having flexibility such as a rubber is attached to a connection member that can be freely detached from the arm 52. A plate-shaped electrode supporter 54 is connected to the tip of the arm 52.

In the present embodiment, for example, snap buttons 53 (53A and 53B) are applied to the connection member. The length of the arm 52 is shorter than a straight line distance between the position of the snap button 53 in the position where the hair band 51 needs to be mounted and the position where the electrode supporter 54 needs to be mounted.

A probe electrode 55 is provided on one surface of the electrode supporter 54. Furthermore, a lead line 56 is drawn from the inner portion of the electrode supporter 54 in a predetermined position of the surface in the electrode supporter 54, and a reference electrode 57 is provided at the tip of the lead line 56.

Figure 6:
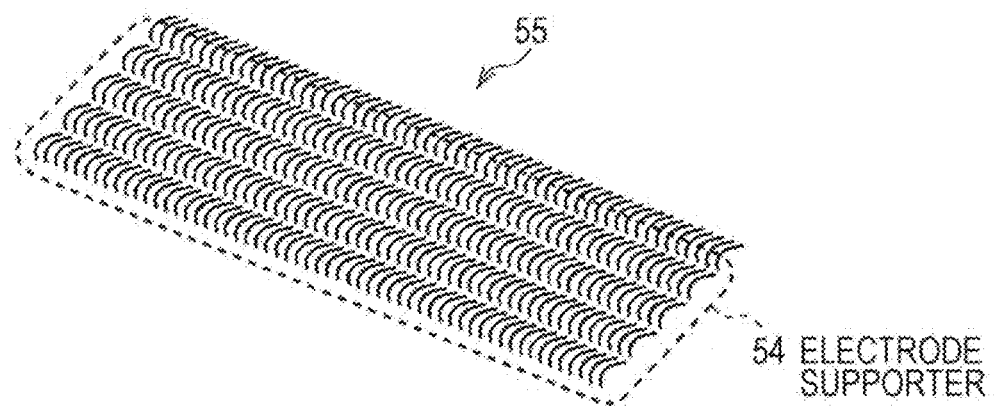
FIG. 6 is a diagram that schematically shows a configuration of a probe electrode.

As shown in FIG. 6, the probe electrode 55 has a structure in which a plurality of teeth formed of a conductive line material is disposed in a line direction and a row direction at equal distances. The teeth are bent at a predetermined position between the root and the tip, and the tip has a rounded shape. A bending angle is an angle in which some [°] is added to 90[°] such that the teeth portion from a tooth tip to a bending position are tilted to the teeth portion from a tooth root to a bending position.

Figure 7:
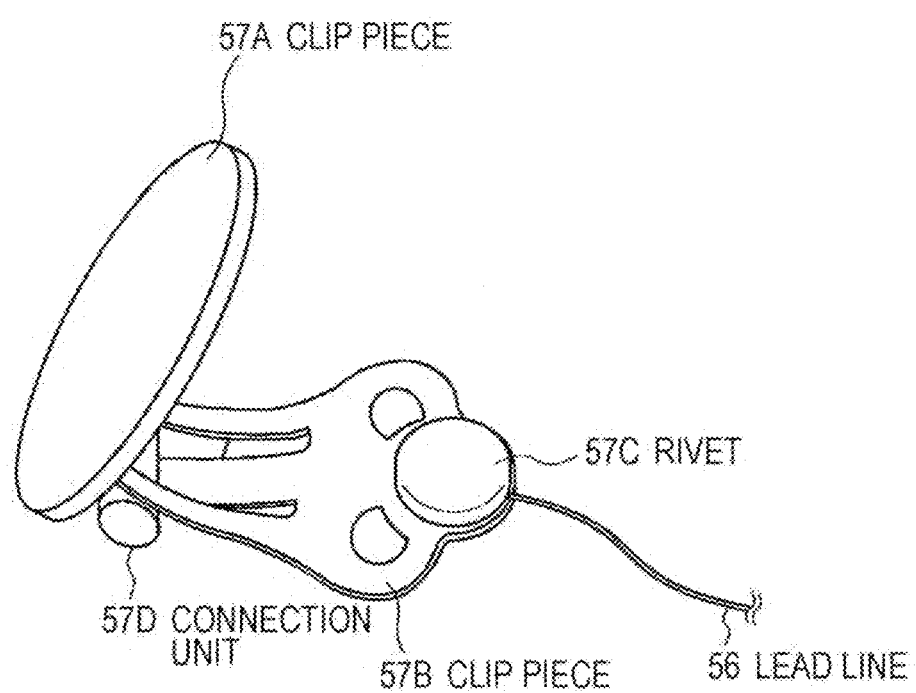
FIG. 7 is a diagram that schematically shows a configuration of a reference electrode.

As shown in FIG. 7, the reference electrode 57 includes a clip piece 57A of a coin shape that has approximately the same surface area as an earlobe, a clip piece 57B that is connected to the clip piece 57A, and a rivet 57C that is provided on a surface of the clip piece 57B facing the clip piece 57A.

A connection portion 57D of the clip piece 57A and the clip piece 57B is connected such that the clip piece 57A and the clip piece 57B can be moved in a separating direction or an approaching direction using the connection portion 57D as a fulcrum. A tip of the lead line 56 is electrically and mechanically fixed between the rivet 57C and the clip piece 57B.

2-2. Mounting Sequence

Next, a mounting sequence of the biological signal measuring equipment 50 will be described. In a first step, the hair band 51 is mounted around the head portion.

In a second step, the electrode supporter 54 to be connected to the hair band 51 via the arm 52 is mounted on a vertex. Specifically, the electrode supporter 54 is placed in the vertex position in the state in which the surface having the probe electrode 55 faces the head portion, and then slides in the same direction of the tooth tip direction in the probe electrode 55.

The arm 52 is formed of a material having flexibility such as rubber, and the length of the arm is shorter than a straight line distance between the position of the snap button 53 where the hair band 51 needs to be mounted and the position where the electrode supporter 54 needs to be mounted. Thus, when the electrode supporter 54 is mounted on the vertex, force by which the arm 52 tends to return to the original length of the arm is applied to the electrode supporter 54 as the force pressed down on the vertex, and the probe electrode 55 provided in the electrode supporter 54 comes into close contact with the scalp.

Furthermore, a plurality of teeth constituting the probe electrode 55 is bent in a predetermined position between the base and the tip, and the tip has a rounded shape (see FIG. 6). Thus, when causing the electrode supporter 54 to slide, the teeth can smoothly be inserted to the root of the hair such that each tooth does not damage the scalp. In addition, each tooth of the probe electrode 55 is entangled in the hair root due to the sliding of the electrode supporter 54. For this reason, the probe electrode 55 can improve the adhesion to the scalp and reduce the position deviation compared to the case of adopting non-bending teeth.

Meanwhile, the vertex, where the probe electrode 55 is situated, is a part in which the contact with the pillow is nearly avoided even when rolling over during normal sleep. Thus, it is possible to reduce the discomfort due to the presence of the probe electrode 55 and avoid the position deviation of the probe electrode 55 due to rolling over.

Thus, the biological signal measuring equipment 50 can greatly reduce sleep hindrance to a subject. Furthermore, it is possible to reduce the burden on the subject without damaging the feeling of mounting to the subject, compared to the sleep polygraph examination in which a plurality of mountings cover the subject.

In a third step, the reference electrode 57 is mounted on an earlobe. Specifically, the earlobe is interposed by a coin-shaped clip piece 57A and a rivet 57C (see FIG. 7) provided in the rivet piece 57B. Since the earlobe is interposed by the clip piece 57A, the rivet 57C, and the rounded portion, pain to the subject is relieved, and as a result, sleep hindrance to the subject can greatly be reduced.

Figure 8:
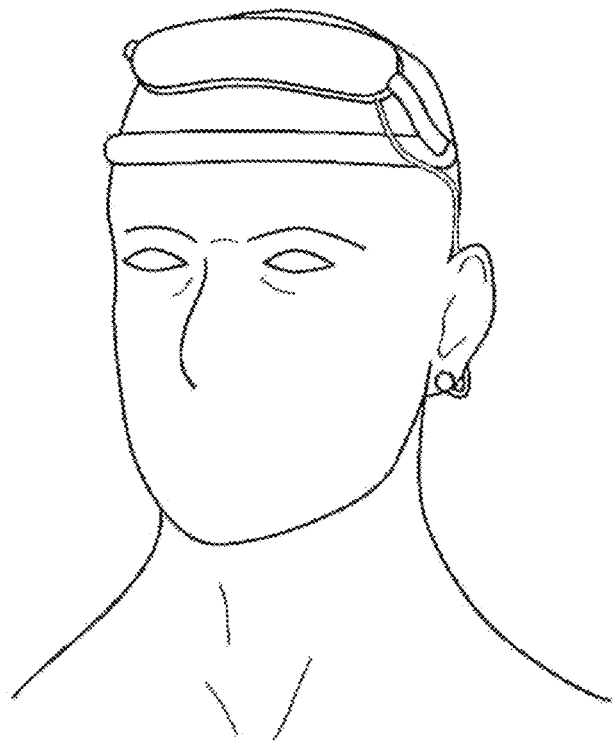
FIG. 8 is a diagram that schematically shows a mounting state of the biological signal measuring equipment.

By going through the mounting sequence mentioned above, for example, as shown in FIG. 8, the biological signal measuring equipment 50 is mounted on the head portion, the probe electrode 55 is fixed to the scalp, and the reference electrode 57 is fixed to the earlobe, respectively. However, the sequence of the mounting is merely an example and is not limited to the sequence of the mounting mentioned above.

The mounting portion in the biological signal measuring equipment 50 is provided, for example, on the surface or in the inner portion of the electrode supporter 54. The configuration of the measuring portion is the same as that of the measuring portion of the biological signal measuring equipment 1 and thus will be omitted herein.

In addition, as mentioned above, since the probe electrode 55 has a structure in which the position deviation is reduced while the adhesion of the teeth to the scalp is improved, even if the electrode is not bonded to the scalp by paste, the measuring portion can accurately amplify the potential difference in vivo, and as a result, the sensitivity in the measuring portion is improved.

Furthermore, the vertex position, where the probe electrode 55 is situated, is a position on the skull. Meanwhile, the vertex position is the earlobe having no muscle where the reference electrode 57 is situated. Thus, the muscle potential component is reduced in the potential difference obtained from the probe electrode 55 and the reference electrode 57, whereby the sensitivity to the brainwave is improved.

In addition, the earlobe, where the reference electrode 57 is situated, is in a position that is relatively far from the head portion. Thus, it is possible to directly understand the behavior of the brain between the position and the vertex position, where the probe electrode 55 is situated, as the potential difference between the probe electrode 55 and the reference electrode 57.

In addition, the probe electrode 55 and the reference electrode 57 are supported on the hair band 51 via the arm 52 and the electrode 54. Thus, the biological signal measuring equipment 50 can prevent the electrode from being dropped during attachment and detachment, and can put the wiring connected to the respective electrodes 55 and 56 in the inner portion of the hair band 51 or the electrode supporter 54. As a result, the biological signal measuring equipment 50 can avoid missing the electrode or entanglement in the cord during attachment or detachment, whereby the usability can be improved.

Furthermore, the arm 52 and the electrode supporter 54 can be detached via the snap button 53. Thus, the biological signal measuring equipment 50 can clean the hair band 51 and can also merely be used as a hair clamp or a cold protection tool.

3. Third Embodiment

3-1. Configuration of Biological Signal Measuring Equipment

A biological signal measuring equipment in a third embodiment is constituted by the head brace 300 (FIGS. 9 to 16) and the jaw brace 500 (FIGS. 19 to 22).

The head brace 300 has a supporter (a hair band) 310 that can be supported on the head portion. The hair band 310 is formed of a plate material having the flexibility and the rigidity such as plastic or metal and is formed in the shape of C. Thus, the hair band is flexibly fitted regardless of the difference in shapes of the head portion, and that state can be held.

In the hair band 310, one end (hereinafter, also referred to as a front end portion) is formed as a higher position than the other end portion (hereinafter, referred to as a rear end portion) so that one end can be visible as a forehead side and the other end portion can be visible as an occiput side (see FIGS. 10 and 11).

That is, a cross-section of the hair band 310 is asymmetric in the front and back as a boundary of a vertical line passing through the center in the hair band 310 in a longitudinal direction and a width direction, and the length of the hair band 310 from the center to the front end portion is shorter than the length of the hair band 310 from the center to the rear end portion.

Furthermore, the width of the hair band 310 is a value that is smaller than a distance between the straight line connecting "F3" with "P3" and the straight line connection "F4" with "P4" in an international 10-20 system. Specifically, it is desirable that the width be equal to or less than 25 [mm]. Thus, the hair band 310 can be flexibly fit to an outline portion passing through a medial sagittal plane while opening a side portion of a head.

Figure 9:
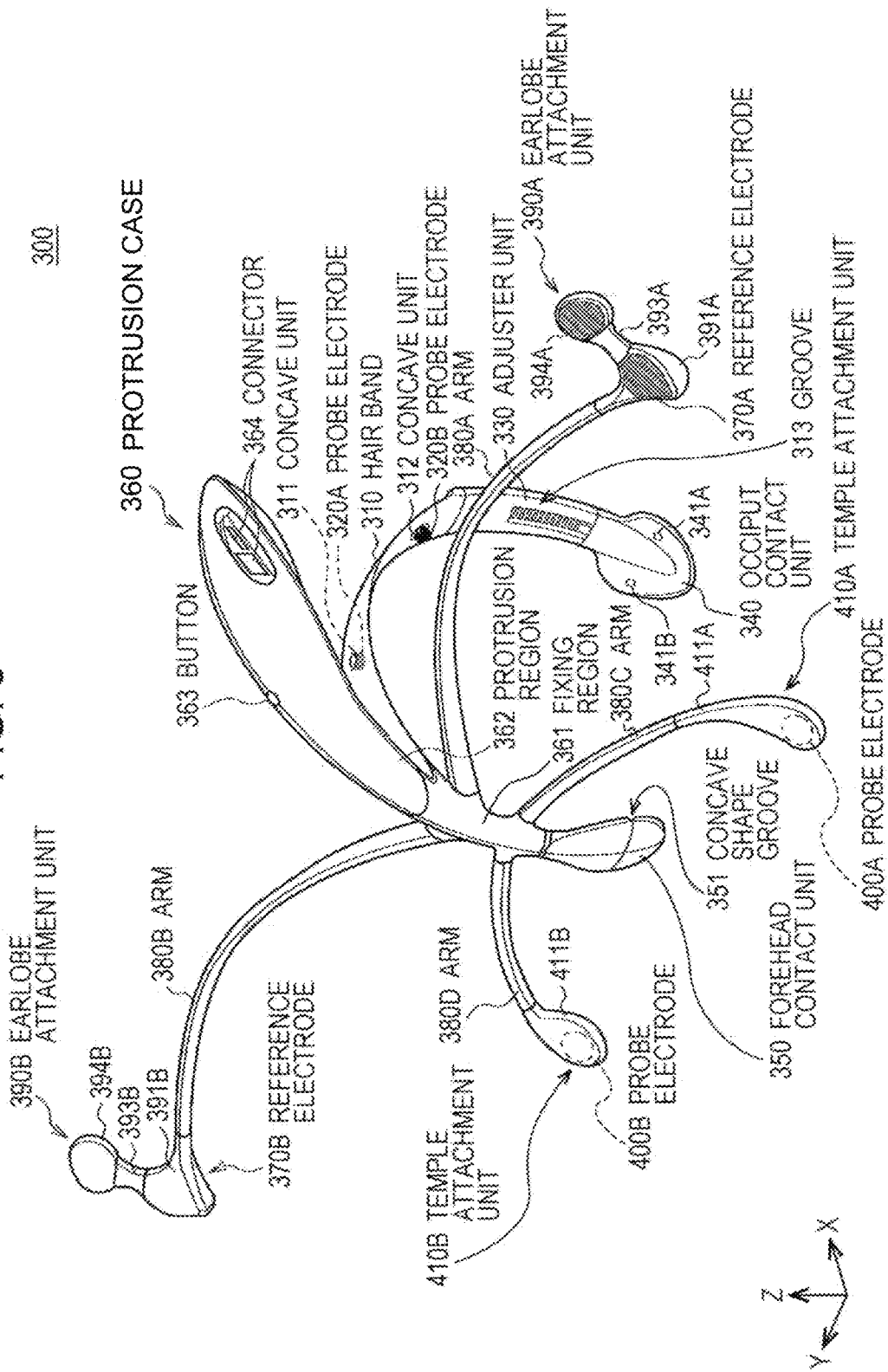
FIG. 9 is a diagram that schematically shows a head brace (perspective).

On an inner surface of the hair band 310, concave portions (hollows) 311 and 312 are provided in the center position of the hair band 310 at a predetermined gap (see FIG. 9). The gap is an average between a medial center portion (Cz in the international 10-20 system) and a medial parietal portion (Pz in the international 10-20 system), and the front end portion is a standard.

Figure 10:
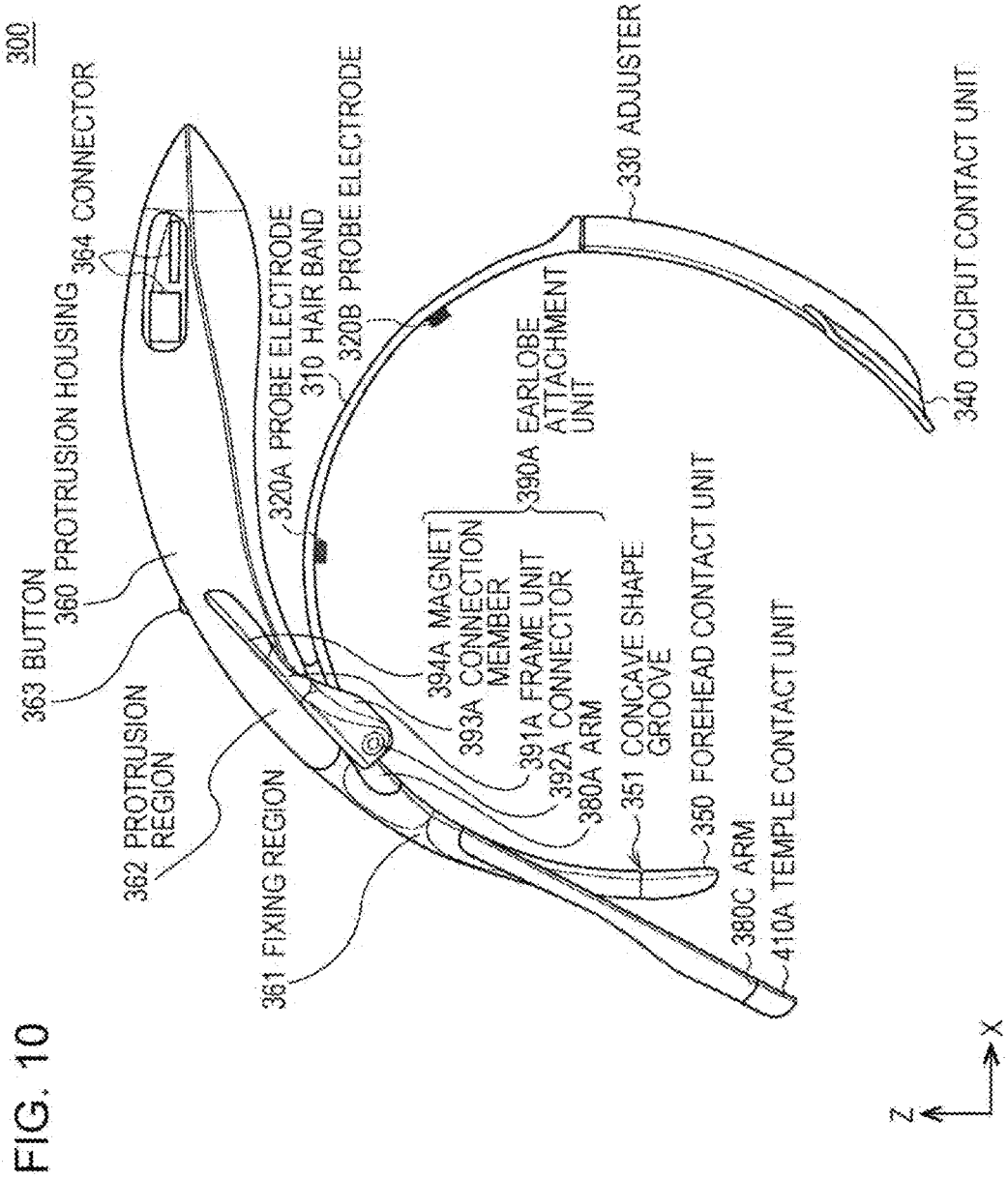
FIG. 10 is a diagram that schematically shows the head brace (left side surface).
Figure 11:
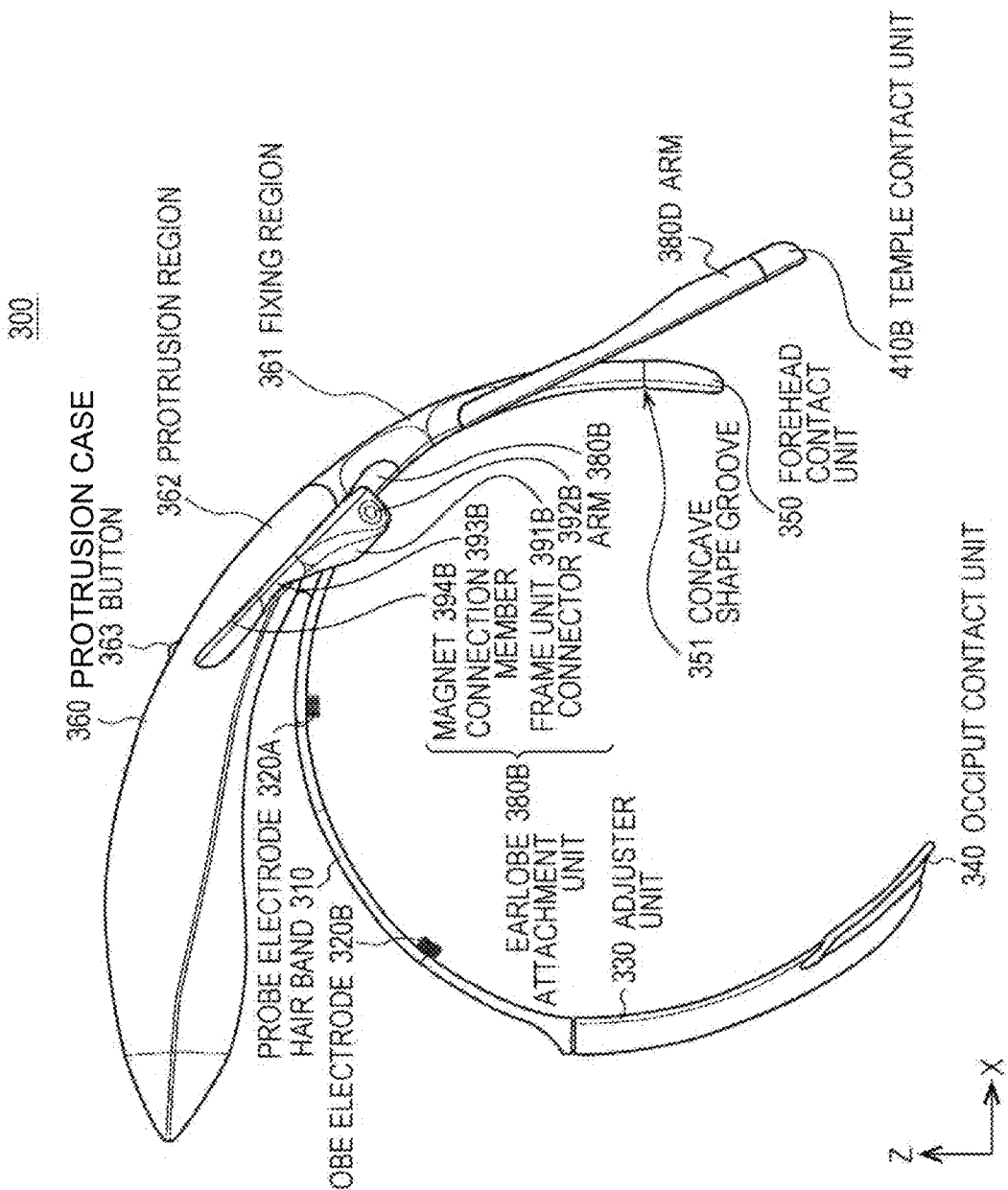
FIG. 11 is a diagram that schematically shows the head brace (right side surface).
Figure 12:
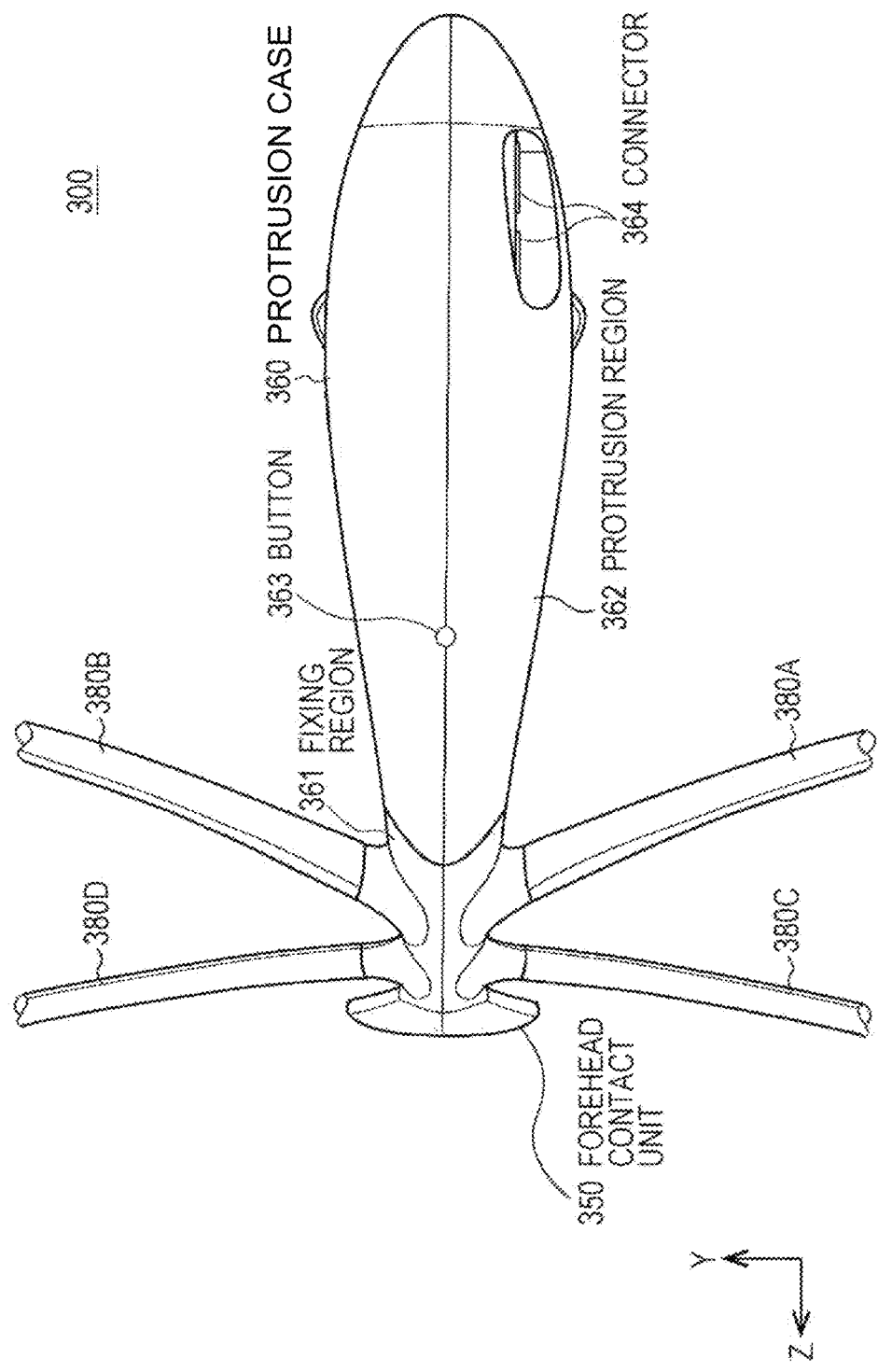
FIG. 12 is a diagram that schematically shows the head brace (upper surface).
Figure 13:
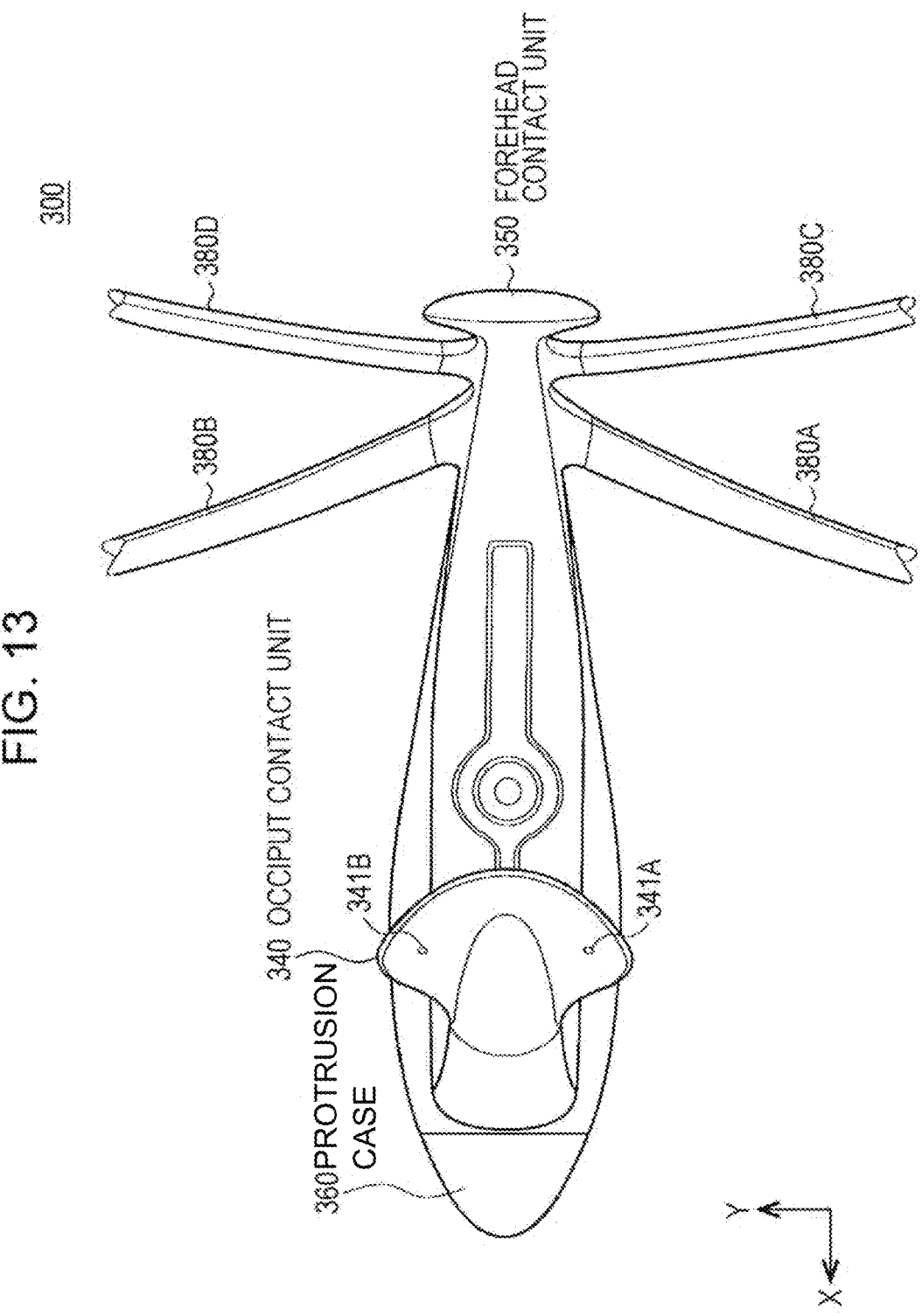
FIG. 13 is a diagram that schematically shows the head brace (lower surface).
Figure 14:
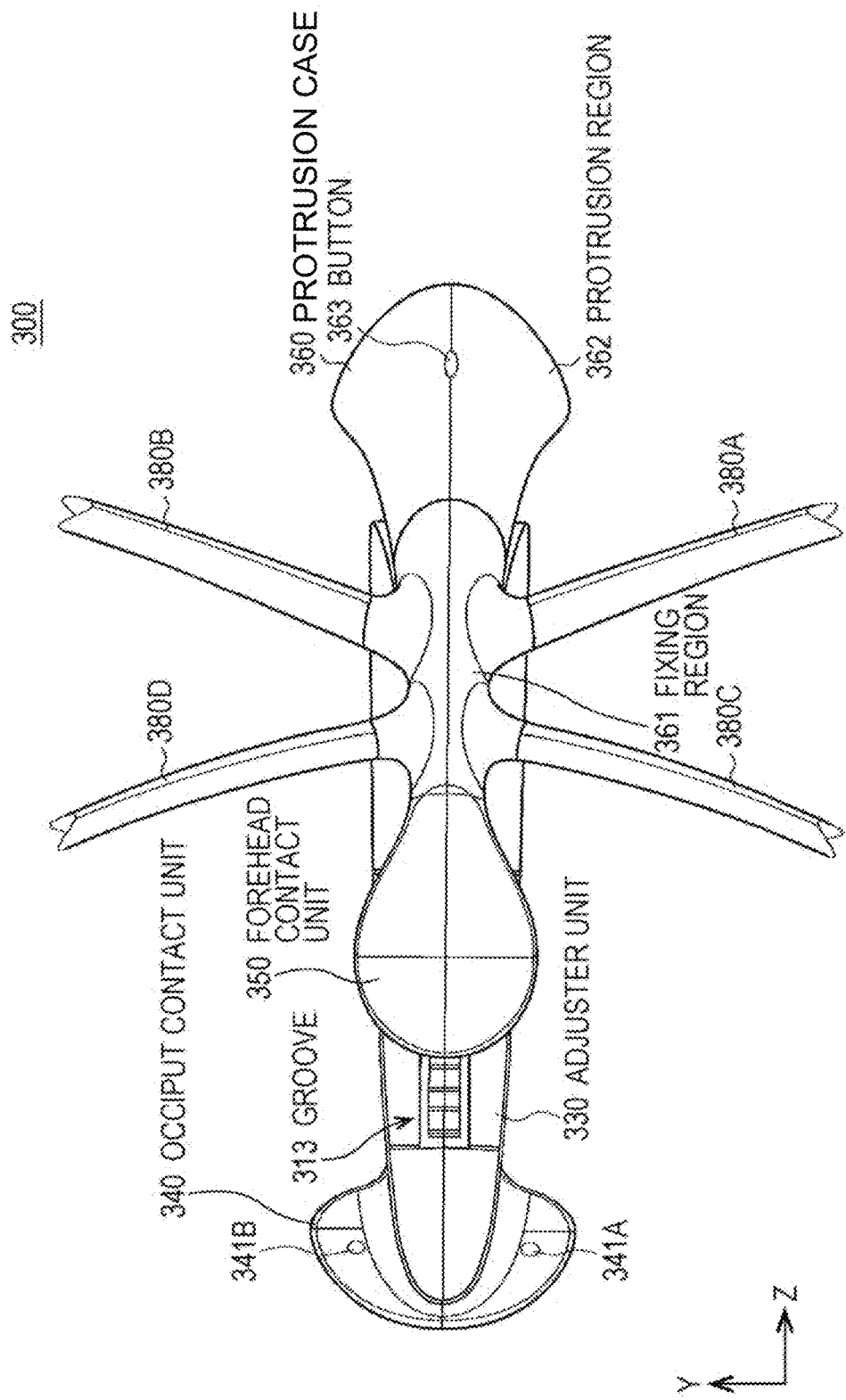
FIG. 14 is a diagram that schematically shows the head brace (front).
Figure 15:
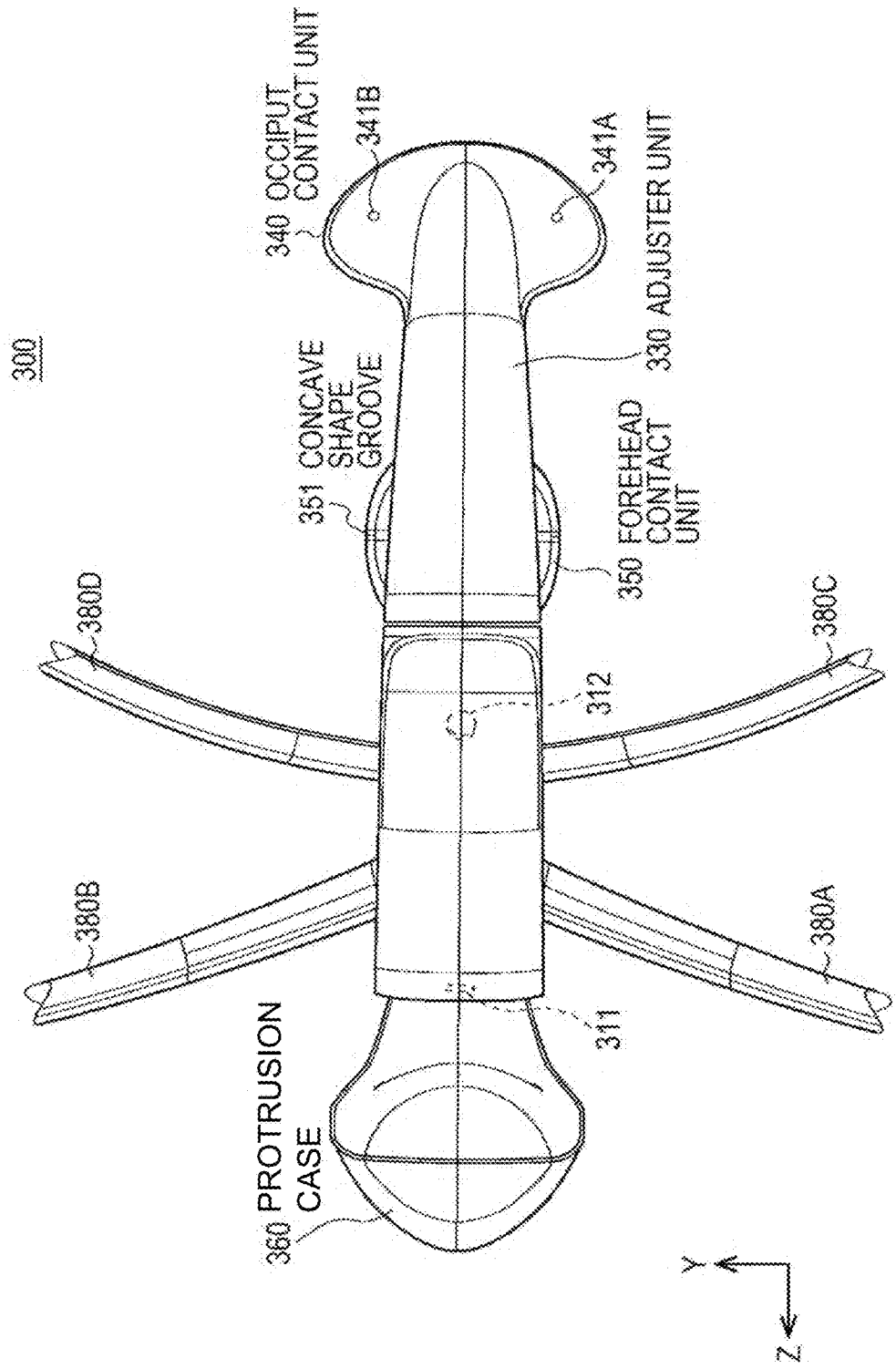
FIG. 15 is a diagram that schematically shows the head brace (rear).
Figure 16:
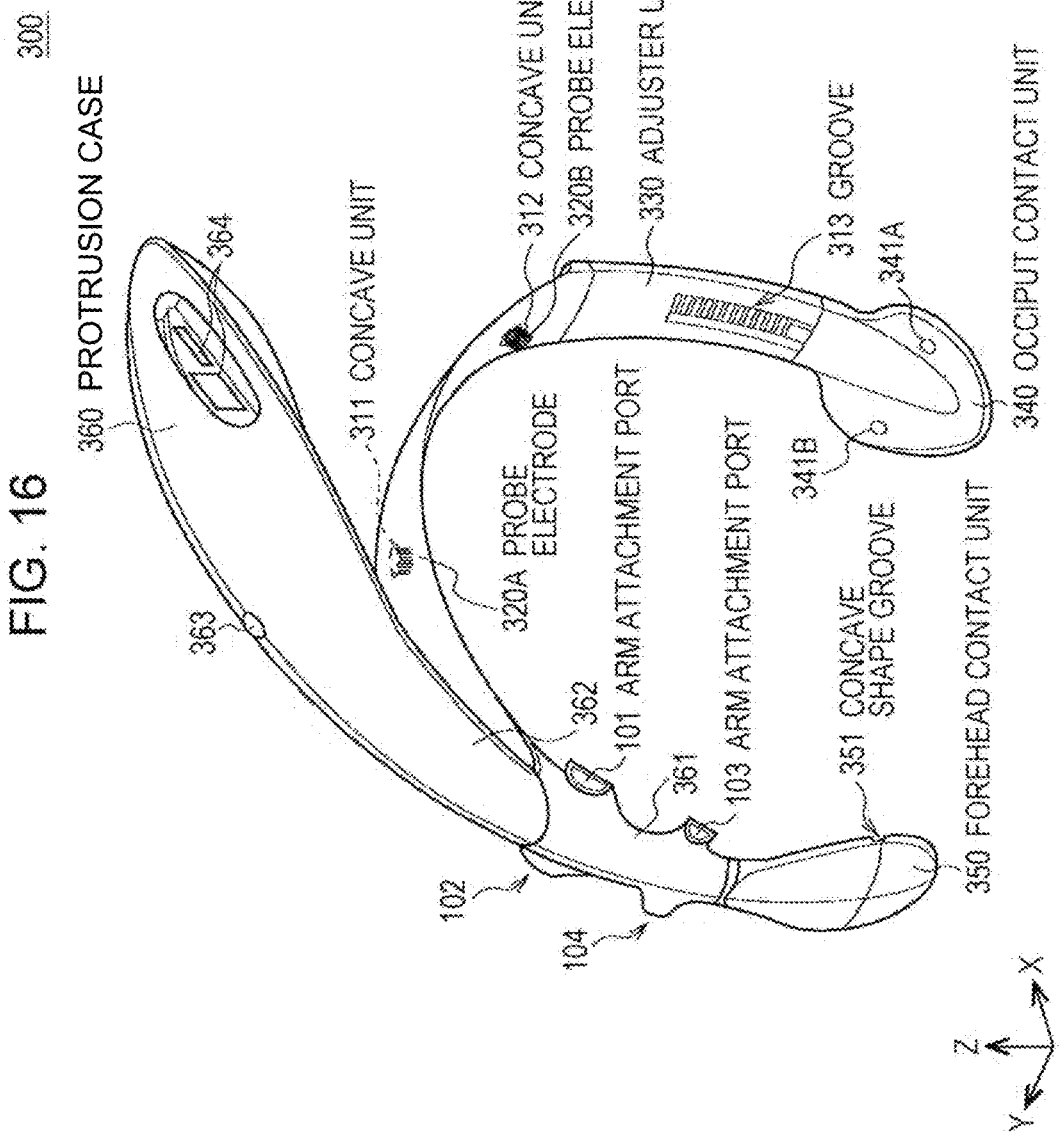
FIG. 16 is a diagram that schematically shows the head brace of an arm separation state.
Figure 17:
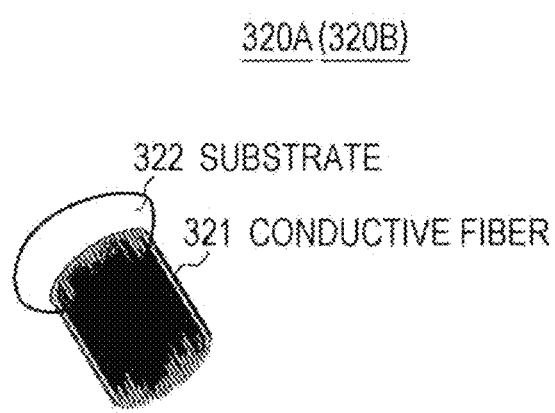
FIG. 17 is a diagram that schematically shows a configuration of a probe electrode.

Probe electrodes 320A and 320B are provided in the concave portions 311 and 312 (see FIGS. 9 to 11). As shown in FIG. 17, the probe electrodes 320A and 320B have a brush structure in which a plurality of conductive fibers 321 is planted in the substrate 322 in a horizontal direction and a vertical direction for each gap.

The material of the conductive fiber 321 is, for example, carbon, amorphous, stainless steel, Thunderon® (copper sulfide chemically bonded to acrylic fibers and nylon fibers) or the like. The thickness (the fiber thickness) or the length of the conductive fiber 321 has a flexible rigidity that does not generate pain in the subject. In the present embodiment, the thickness of the conductive fiber 321 is 25 [μm], and the length of the conductive fiber 321 is 10 [mm].

The substrate 322 is fixed to bottom surfaces of the concave portions 311 and 312. In addition, a planting area of the conductive fiber 321 and the surface areas of the concave portions 311 and 312 are set, respectively in such a manner that the mobility of the conductive fiber 321 is not damaged. Furthermore, the length of the conductive fiber 321 and the depths of the concave portions 311 and 312 are set, respectively such that the tip of the conductive fiber 321 is protruded from the inner surface of the hair band 310 so as not to damage the fit property of the hair band 310 to the head portion.

Among the concave portion 312 and the rear end portion of the hair band 310, a plurality of grooves 313 is formed in the longitudinal direction of the hair band 310 for each predetermined gap (see FIG. 9). In the portion formed with the grooves 313, an adjuster portion 330 is provided which can slide in the longitudinal direction of the hair band 310 using the portion as a core (see FIGS. 9 to 11 and 14 to 16).

In the portion facing the groove 313 of the hair band 310 of the inner surface of the adjuster portion 330, a claw (not shown) capable of being fitted to the groove 313 is provided, and the whole length of the hair band 310 can be adjusted in a step manner. Thus, it is possible to increase the mounting property of the hair band 310 to meet the size or the shape of a head.

A difference, between the whole length of the hair band 310 when the claw is fitted to the groove 313A (FIG. 18) closest to the front end portion of the groove 313 and the whole length of the hair band 310 when the claw is fitted to the farthest groove 313B (FIG. 18), is 30 [mm] in the present embodiment.

Furthermore, in the present embodiment, the groove 313C (FIG. 18) becoming the middle of each groove 313 is the standard, and the length of the adjuster portion 330 to the middle groove 313C is a length in which the opening end of the adjuster portion 330 when the claw is fitted to the middle groove 313C is immediately above the occiput center portion (Oz in the international 10-20 system).

Thus, since the opening end of the adjuster portion 330 can be placed so as to avoid the contact of the tip portion of the adjuster portion 330 to the protrusion portion of the head portion, the pain to the subject during sleep is relieved, and as a result, the sleep hindrance to the subject is greatly reduced.

In addition, a width of the portion from the position separated from the concave portion 312 to the rear end portion side at a predetermined gap to the rear end portion is narrower than the width from the position to the front end portion (see FIG. 18), and the step portion in the portion becomes a stopper to the adjuster portion 330. Thus, the number of the components is suppressed compared to the case of separately providing the stopper, and the size can be reduced accordingly.

A portion 340 (hereinafter, also referred to as an occiput contact portion) coming into contact with the occiput is attached to the rear end (the opening end of the adjuster portion 330) of the hair band 310 (see FIGS. 9 to 11 and 13 to 16). The occiput contact portion 340 has a pointed fillet shape or a spade shape in which the width is narrow in the connection portion, gradually spreads, and becomes narrower as it approaches from the middle to the tip, and has an area wider than a portion (a jaw contact portion 350 described later) which is set to come into contact with the jaw and is attached to the front end of the hair band 310. Thus, the stability to the head portion can be enhanced.

Figure 18:
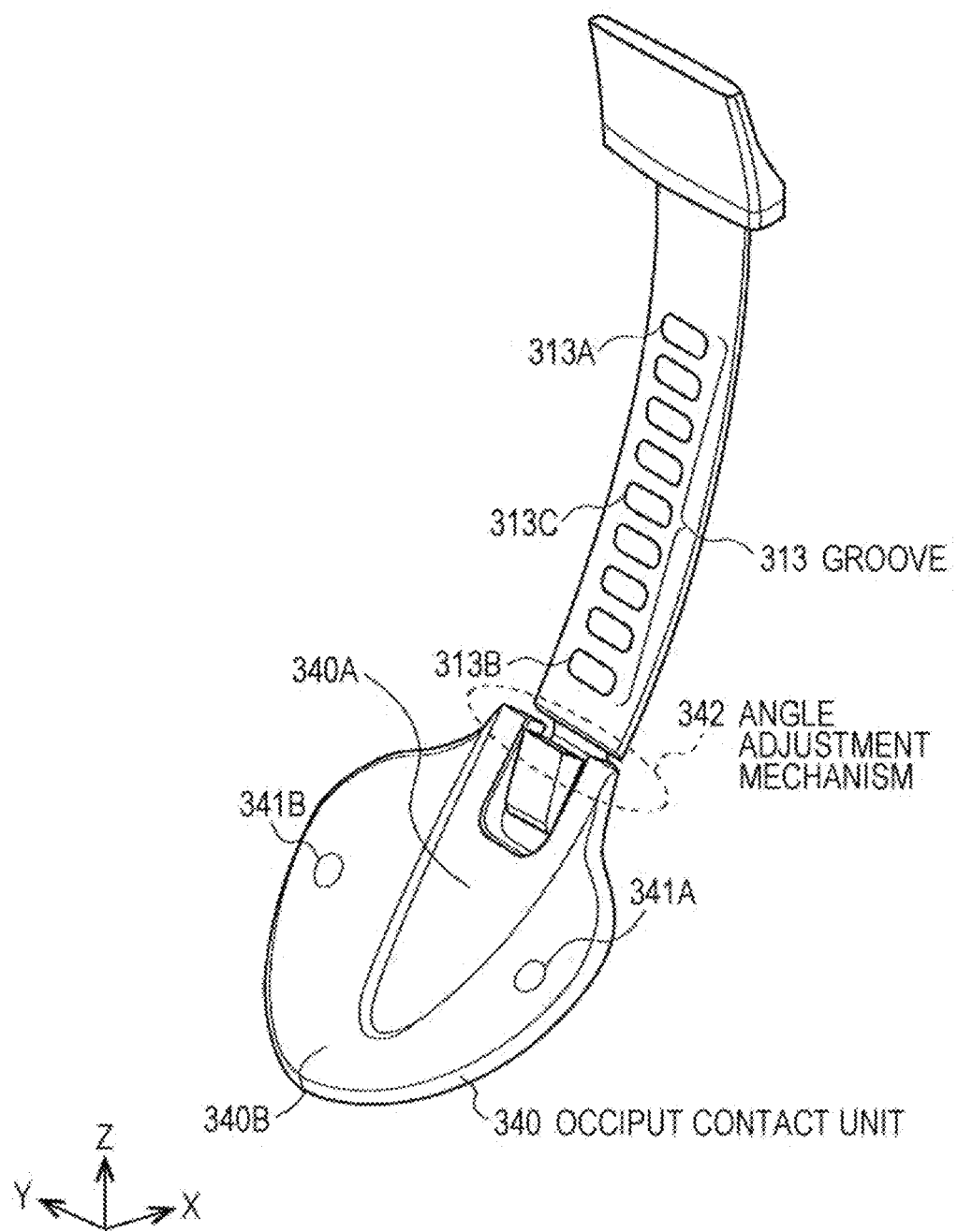
FIG. 18 is a diagram that shows details of a rear end portion of a hair band.
Figure 19:
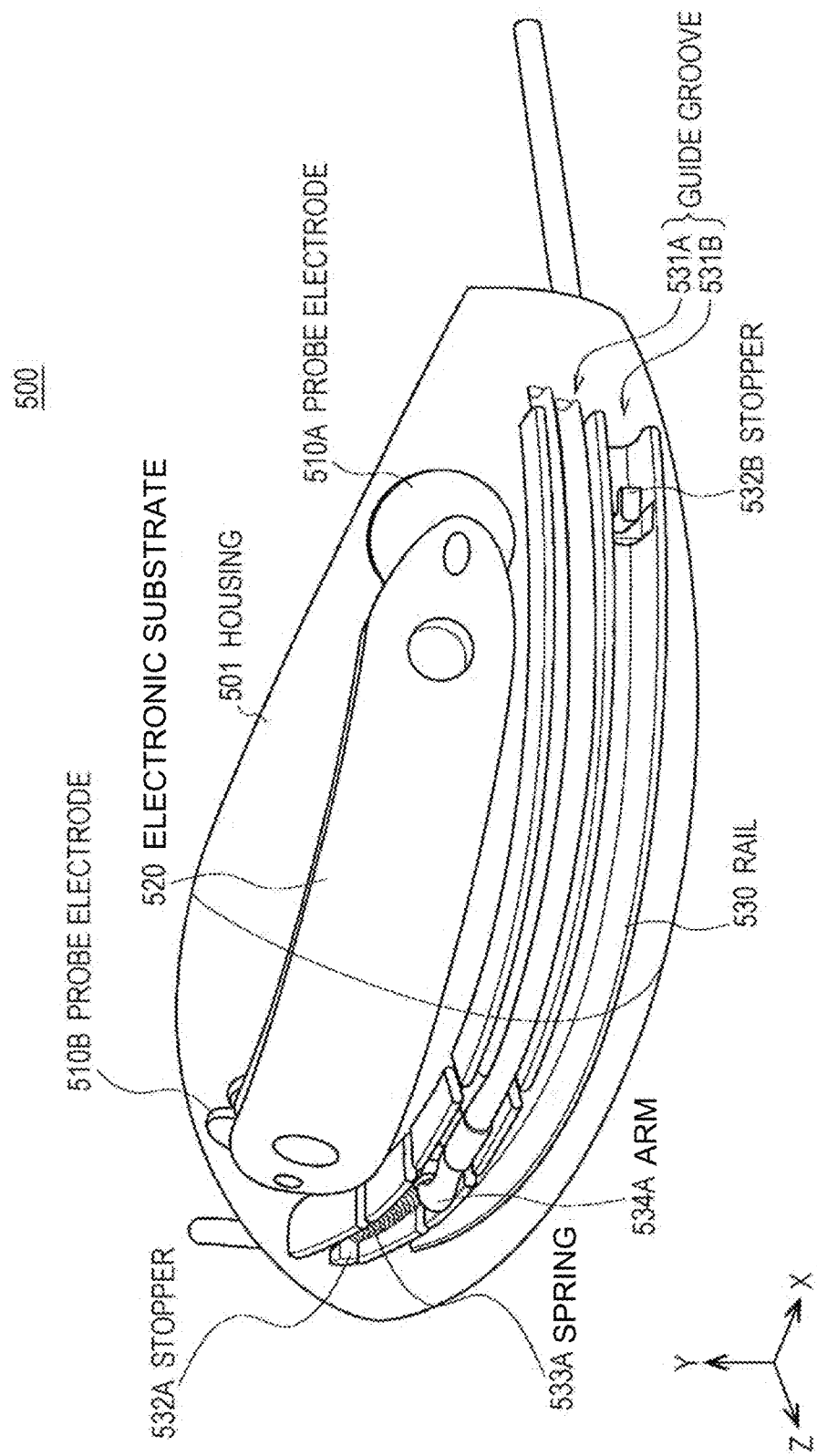
FIG. 19 is a diagram that schematically shows a jaw brace (perspective).
Figure 20:
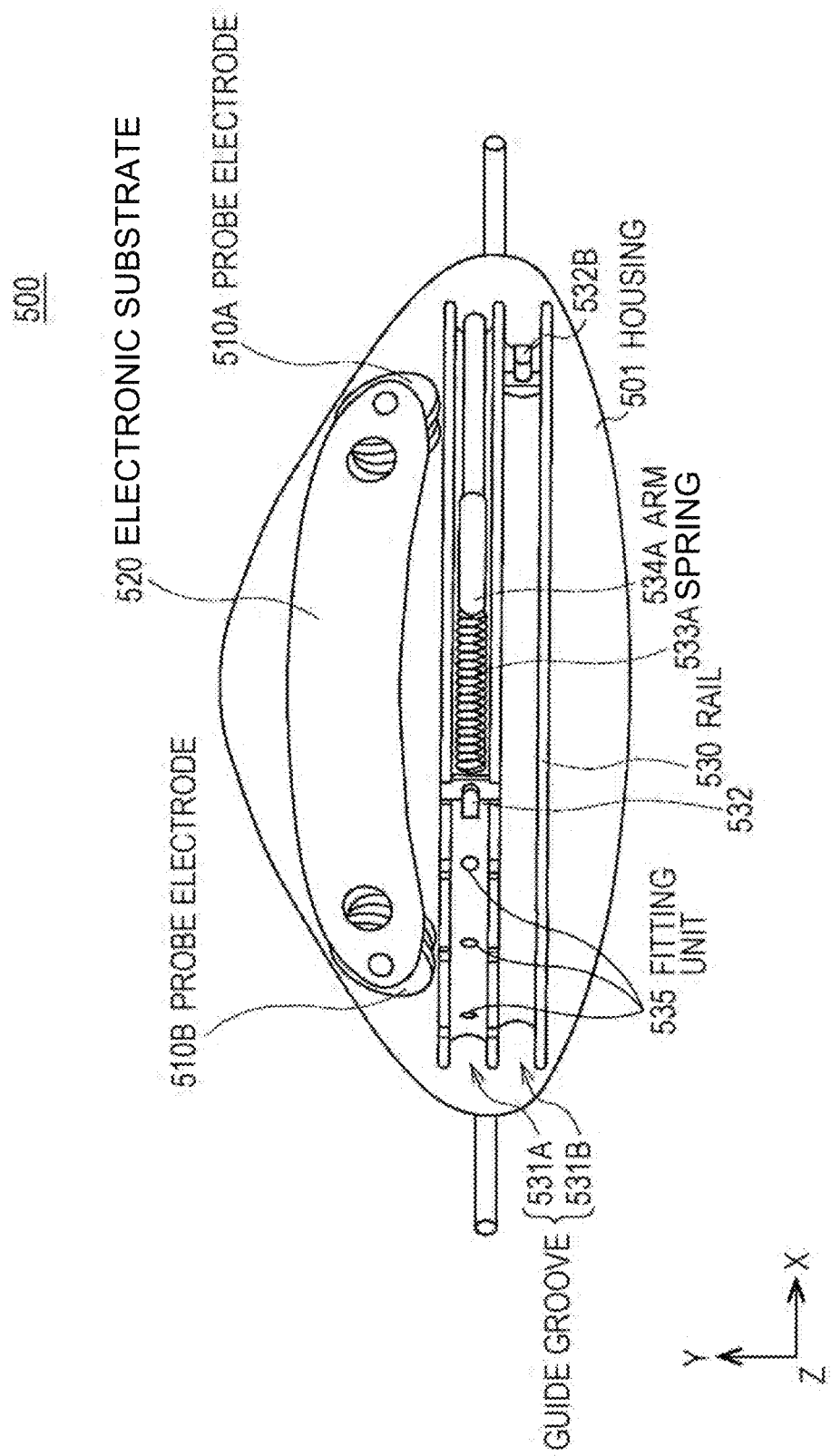
FIG. 20 is a diagram that schematically shows the jaw brace (front).
Figure 21:
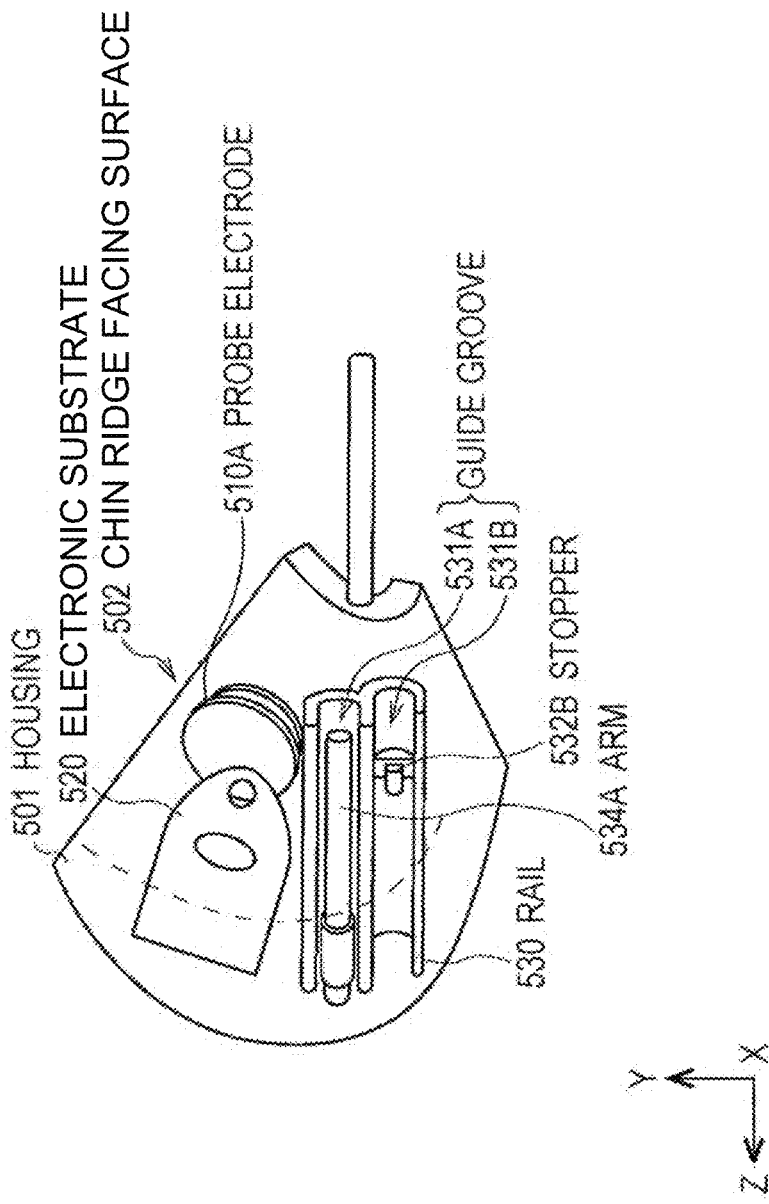
FIG. 21 is a diagram that schematically shows the jaw brace (side).
Figure 22:
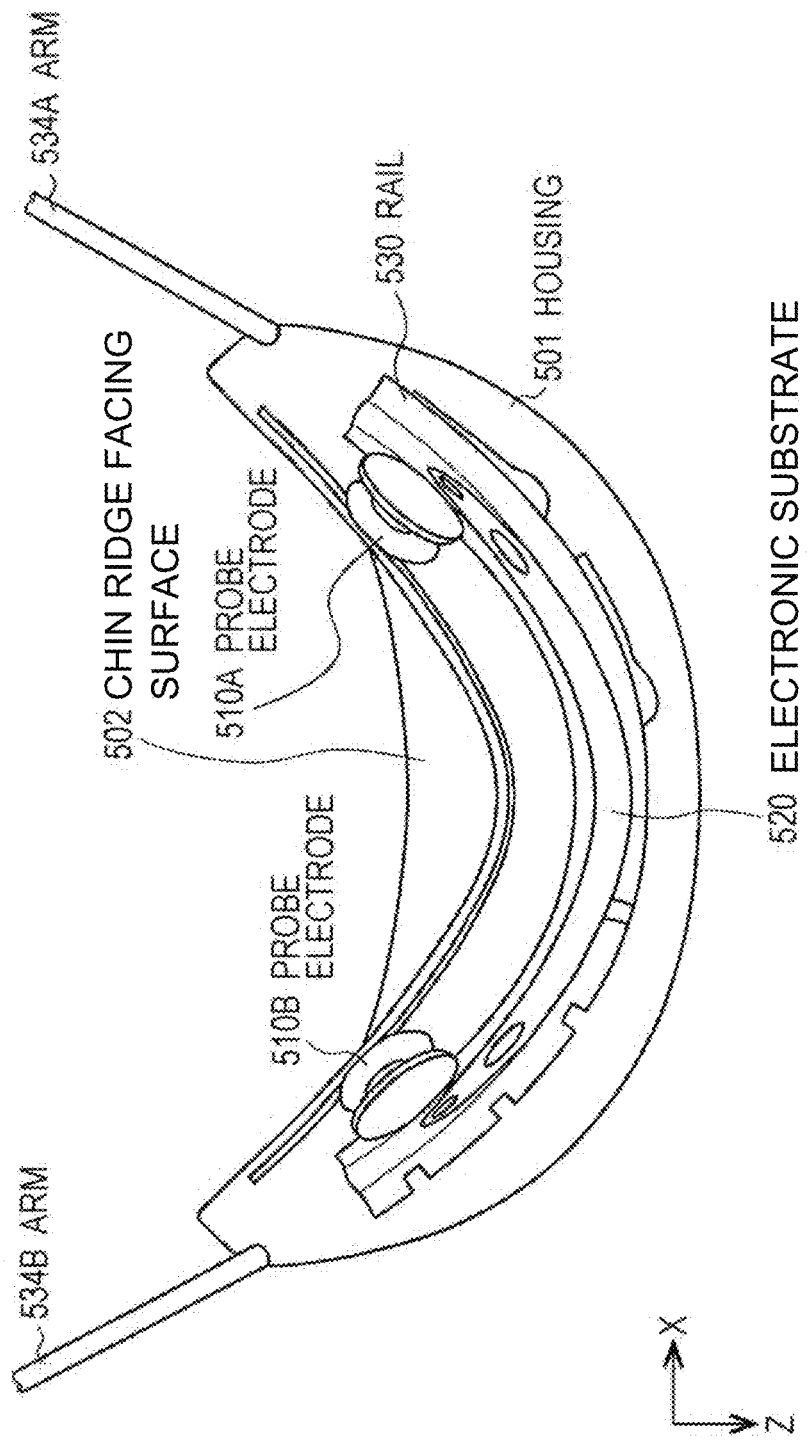
FIG. 22 is a diagram that schematically shows the jaw brace (upper surface).

The center of the occiput contact portion 340 and the core region 340A in the vicinity thereof are formed of a rigid material, and a peripheral region other than the core region 340A is formed of a soft material such as silicon or urethane (see FIG. 18). Thus, the adhesion to the head portion can be enhanced, and the inroad to the head portion is suppressed.

A hair clip (not shown) or a sucker (not shown) is attached to the inner surface side of the core region 340A via drilled holes 341A and 341B in a freely attachable and detachable manner. Thus, it is possible to further increase the stability to the head portion regardless of the presence or the absence of the hair.

Furthermore, the core region 340A is in the state of being recessed by the height of the hair clip or the sucker compared to the peripheral region 340B. Thus, the state, in which the occiput contact portion 340 floats from the head portion due to the attachment of the hair clip or the sucker, is avoided in advance.

The connection portion between the core region 340A and the adjuster portion 330 is provided with an angle adjusting mechanism 342 that varies the angle of the inner surface of the occiput contact portion 340 to the inner surface of the hair band 310. Thus, the angle of the inner surface of the occiput contact portion 340 to the contact portion of the head portion can be adjusted, and as a result, the stability to the head portion can be further enhanced.

A portion (hereinafter, also referred to as a jaw contact portion) 350 coming into contact with the jaw is attached to the front end portion of the hair band 310 (see FIGS. 9 to 16). The jaw contact portion 350 is formed in a teardrop shape and is formed of a soft material such as silicon or urethane. Thus, the adhesion to the jaw can be enhanced and the inroad to the jaw is suppressed.

The inner surface in the jaw contact portion 350 is formed with a concave shape groove 351 that divides the inner surface into an upper region and a lower region (see FIGS. 9 to 11 and 15 to 16). The flexibility of the jaw contact portion 350 is improved by the concave shape groove 351, and, as a result, the adherence of the jaw contact portion 350 to the jaw can be further enhanced.

An outer surface of the hair band 310 is provided with a protrusion-shaped case (hereinafter, also referred to as a protrusion case) 360 accommodating an electronic device (see FIGS. 9 to 16). The protrusion case 360 includes a fixing region 361 and a protrusion region 362 (see FIGS. 9 to 12 and 14 to 16). The fixing region 361 is fixed to the outer surface of the hair band 310 immediately over the jaw contact portion 350. An upper stage and a lower stage of the fixing region 361 are provided with a pair of arm attachment openings 101, 102, 103, and 104, respectively (see FIG. 16).

The protrusion region 362 is separated from the hair band 310, is separated from the apex portion outer surface of the hair band 310 by a predetermined distance, and is protruded outward. That is, the hair band 310 can be smoothly mounted without hindering the change in curved state when mounting the hair band 310.

The shape of the protrusion region 362 is a flat shape in which the degree of bending is gentler than the hair band 310. Thus, compared to the case where the electronic device is accommodated in the hair band 310, the selection width of the circuit board can be widened, and the affect due to the bending of the hair band 310 is avoided.

On the upper surface of the protrusion region 362, a long-press button 363 is provided which turns the power source on or off by the push operation for some seconds (see FIGS. 9, 10, 12, and 16). Thus, it is suppressed that the surrounding objects are touched during sleep or standing to erroneously turn the power source on or off.

On the side surface of the protrusion region 362, a plurality of kinds of connectors 364 (see FIGS. 9 to 12, 14, and 16) to a removable such as, for example, an SD (Secure Digital) card or an USB (Universal Serial Bus) memory is provided.

Arms 380A and 380B supporting a pair of reference electrodes 370A and 370B is attached to the arm attachment openings 101 and 102 of the upper stages in a freely attachable and detachable manner (see FIGS. 9 to 11). The arms 380A and 380B have the length reaching the earlobe along the head portion surface via behind an ear, and the tips thereof are provided with portions (hereinafter, also referred to as earlobe attachment portions) 390A and 390B which attach the reference electrodes 370A and 370B to the earlobe (see FIGS. 9 to 11).

Arms 380C and 380D supporting a pair of probe electrodes 400A and 400B are attached to the arm attachment openings 101 and 102 of the lower stage in a freely attachable and detachable manner (see FIGS. 9 to 11). The arms 380C and 380D have the lengths reaching a hollow (hereinafter, also referred to as a temple) surrounded by a frontal bone, a zygomatic arch, a zygomatic orbital protrusion, and the tips thereof are provided with portions 410A and 410B (hereinafter, also referred to as temple attachment portions) which attach the probe electrodes 400A and 400B to the temple (see FIGS. 9 to 11).

Each arm 380 is formed of a soft material such as silicon, PBT or PP and is formed in a cylindrical shape. Line-shaped members (not shown) having the rigidity such as a piano line or a wire are added to the inner portions of each arm 380. Thus, the shape of the arm 380 can flexibly be adjusted, and the state after the adjustment can be held.

The earlobe attachment portions 390A and 390B (FIGS. 9 to 11) have frames 391A and 391B connected to the tips of the arms 380A and 380B, and jack type connectors 392A and 392B are provided in the lower ends of the frames 391A and 391B.

The frames 391A and 391B have structures in which the magnetic reference electrodes 370A and 370B are exposed to the central region excluding the whole plane regions of the frames 391A and 391B or margins. Furthermore, disk-shaped magnets 394A and 394B are attached to the frames 391A and 391B via the plate-shaped connection members 393A and 393B having flexibility.

Thus, the earlobe attachment portions 390A and 390B bend the connection members 393A and 393B, the earlobe is interposed between the magnets 394A and 394B and the reference electrodes 370A and 370B, and the reference electrodes 370A and 370B can be fixed to the earlobe by magnetic force.

The temple attachment portions 410A and 410B (FIG. 9) have frames 411A and 411B connected to the tips of the arms 380A and 380B and have the structures in which the probe electrodes 400A and 400B are exposed to the central region excluding the whole plane regions or the margins of the frames 411A and 411B. A sheet having stickiness to the skin such as a solid gel is attached to the frames 411A and 411B. Thus, the stability and the adhesion of the probe electrodes 400A and 400B to the temple are ensured.

In addition, the respective different shapes can be allocated to the frames 391A, 391B, 411A and 411B such that "upper right", "upper left", "lower right", and "lower left" are visible.

Lead lines (not shown) are connected to the respective reference electrodes 370 and the respective probe electrodes 400, and the lead lines are drawn to the inner portion of the fixing region 361 in the protrusion case 360 along the line-shaped member (not shown) disposed in the inner space of the corresponding arm 380. Furthermore, lead lines (not shown) are also connected to the respective probe electrodes 320 attached to the hair band 310, and the lead lines are drawn to the inner portion of the fixing region 361 of the protrusion case 360 via the inner portion of the hair band 310.

The inner portion of the fixing region 361 is connected to an amp (not shown) allocated to the respective electrodes 320, 370, and 400, and the ground lines of the amp are connected to one ground line, respectively. This is a grounding method called a star type earth.

The position, where the fixing region 361 is disposed, is a position where each of the electrodes 320, 370, and 400 are the shortest distance to the position. For this reason, the disturbance noise overlapping the lead lines to the electrodes 320, 370, and 400 is greatly reduced. Furthermore, the ground line of the amp allocated to the respective electrodes 320, 370, and 400 is concentrated in one point in the fixing region 361, and thus, the loop due to the ground point is reduced.

In addition, in the fixing region 361, in addition to the amp, an analog-based electronic element having a high degree of the influence of the noise is predominantly provided, and in the protrusion region 362, a digital-based electronic element having a small degree of the influence of noise is predominantly provided.

The jaw brace 500 has a case 501 that is formed by combining a flexible material with a rigid material, and the case 501 is formed with a surface (hereinafter, also referred to as a chin ridge facing surface) 502 corresponding to the shape of the chin ridge in the lower jaw. A sheet having the stickiness such as a solid gel is attached to the chin ridge facing surface 502.

Thus, the chin ridge can be easily fitted according to the shape of the chin ridge facing surface 502 by touch without seeing a mirror or the like, and the stability of the fitted state can be promoted.

The probe electrodes 501A and 510B, the electronic substrate 520, and the rail 530 are mounted in the inner portion of the case 501.

The probe electrodes 510A and 510B are formed in the disk shape, and are disposed in a position on the vertical line of the chin node.

The electronic substrate 520 is a substrate having flexibility and is disposed between one probe electrode 510A and the other probe electrode 510B in the state of the curve line along the chin ridge facing surface 502. In the electronic substrate 520, an amp (not shown) for amplifying the biological signal to be sensed by the probe electrodes 510A and 510B is disposed.

The rail 530 is formed of a material having a high sliding property such as POM and is disposed horizontally in the state of the curve along the chin ridge facing surface 502. The rail 530 is formed with an upper stage guide groove 531A and a lower stage guide groove 531B.

A pile-shaped stopper 532A is fixed to one end of the upper stage guide groove 531A, and one end of the spring 533A expanded and contracted along an orbit of the upper stage guide groove 531A in each stopper 532A. One end of the arm 534A inserted into the upper stage guide groove 531A is fixed to the other end of the spring 533A. The other end of the arm 534A is provided with a pin type connector (not shown) corresponding to the connector 392 of the earlobe attachment portion 390A, and is attached to and detached from the connector 392.

A pile-shaped stopper 532B is fixed to one end of the lower stage guide groove 531B. The one end is an end that is situated at a side opposite to the one end provided with the upper stage guide groove 531A and the stopper 532A.

Like the case of the upper stage guide groove 531A, one end of a spring (not shown) is fixed to the stopper 532B and one end of an arm (not shown) is fixed to the other end of the spring (not shown). The other end of the arm is provided with a connector (not shown) of a pin type corresponding to the connector 392 of the earlobe attachment portion 390B, and the connector is attached to and detached from the connector 392.

Thus, springs 533A and 533B adjust the arms 534A and 534B to the length depending on the distance between the jaw brace 500 and the earlobe attachment portion 390A, give the mutually contradictory pressure, and can prevent the position deviation of the jaw brace 500.

In addition, arms 534A and 534B are formed of a soft material such as silicon, PBT or PP, and are formed in the cylindrical shape. The inner portions of the arms 534A and 534B are added with line-shaped members (not shown) having rigidity such as a piano line or a wire line. Thus, the arms 534A and 534B can be disposed along a surface on a lower jaw angle portion, and the state after the adjustment can be held.

Furthermore, the stoppers 532A and 532B can adjust the fixing positions thereof by changing the fitting part to a plurality of fitting portions 535 (see FIG. 20) formed in the orbital direction of the upper stage guide grooves 531A and 531B for each predetermined gap.

3-2. Mounting Sequence

Next, the mounting sequence of the biological signal measuring equipment will be described. In a first step, firstly, the hair band 310 is covered in the front and rear direction of the head portion.

Since the front end portion of the hair band 310 is formed as a position higher than the rear end portion (see FIGS. 10 and 11), it is possible to intuitively grasp the front and rear direction of the head brace 300 to a subject. Furthermore, the hair band 310 is formed of a plate material having flexibility and rigidity such as plastic or metal, and the width thereof has a value smaller than the distance the straight line connecting "F3" and "P3" and the straight line connecting "F4" and "P4" in the international 10-20 system.

For this reason, the hair band 310 is flexibly fitted to the outline portion passing through the median sagittal plane while opening the side portion of the head, and, as a result, a migraine or discomfort due to the subject lying down is greatly relieved.

Furthermore, the hair band 310 has a structure with the front and rear direction of the head portion interposed therebetween via the outline portion passing through the median sagittal plane, and thus, the weight of the hair band 310 itself presses the outline portion passing through the median sagittal plane.

Figure 23:
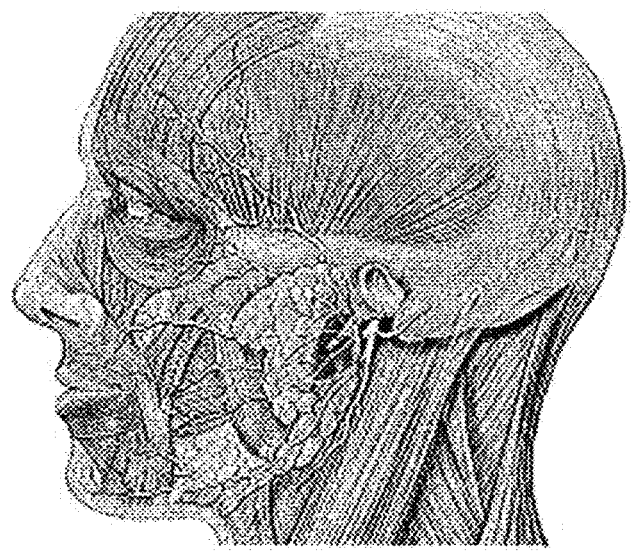
FIG. 23 is a diagram that shows a nervous system from a face to a head portion.
Figure 24:
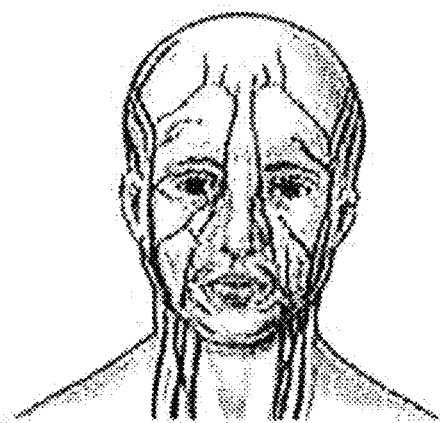
FIG. 24 is a diagram that shows a blood vessel system from the face to the head portion.
Figure 25:
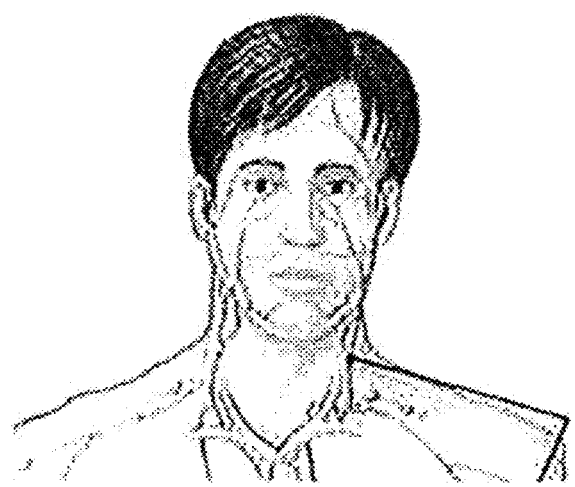
FIG. 25 is a diagram that shows a lymph system from the face to the head portion.
Figure 26:
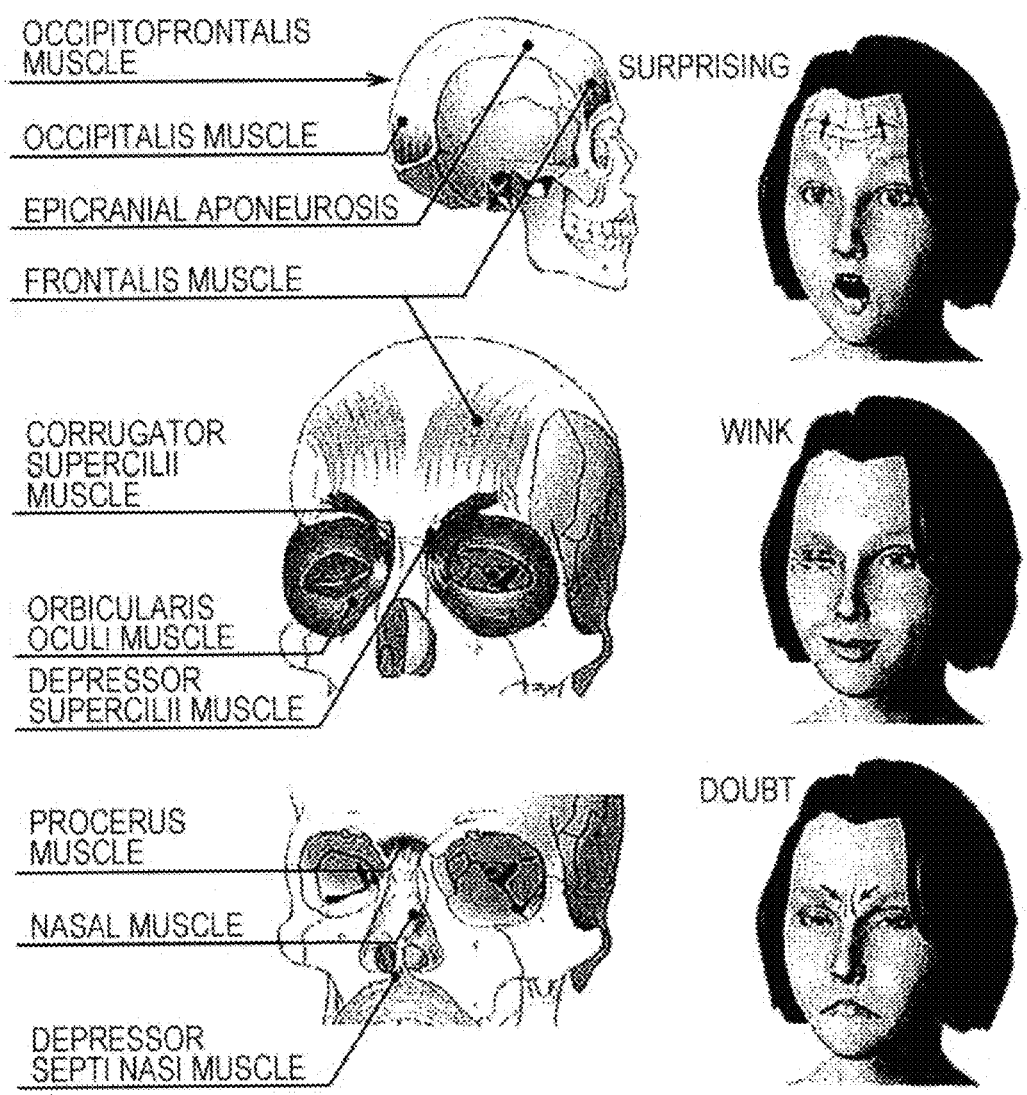
FIG. 26 is a diagram that shows a relationship between a muscle and an expression from the face to the head portion.
Figure 27:
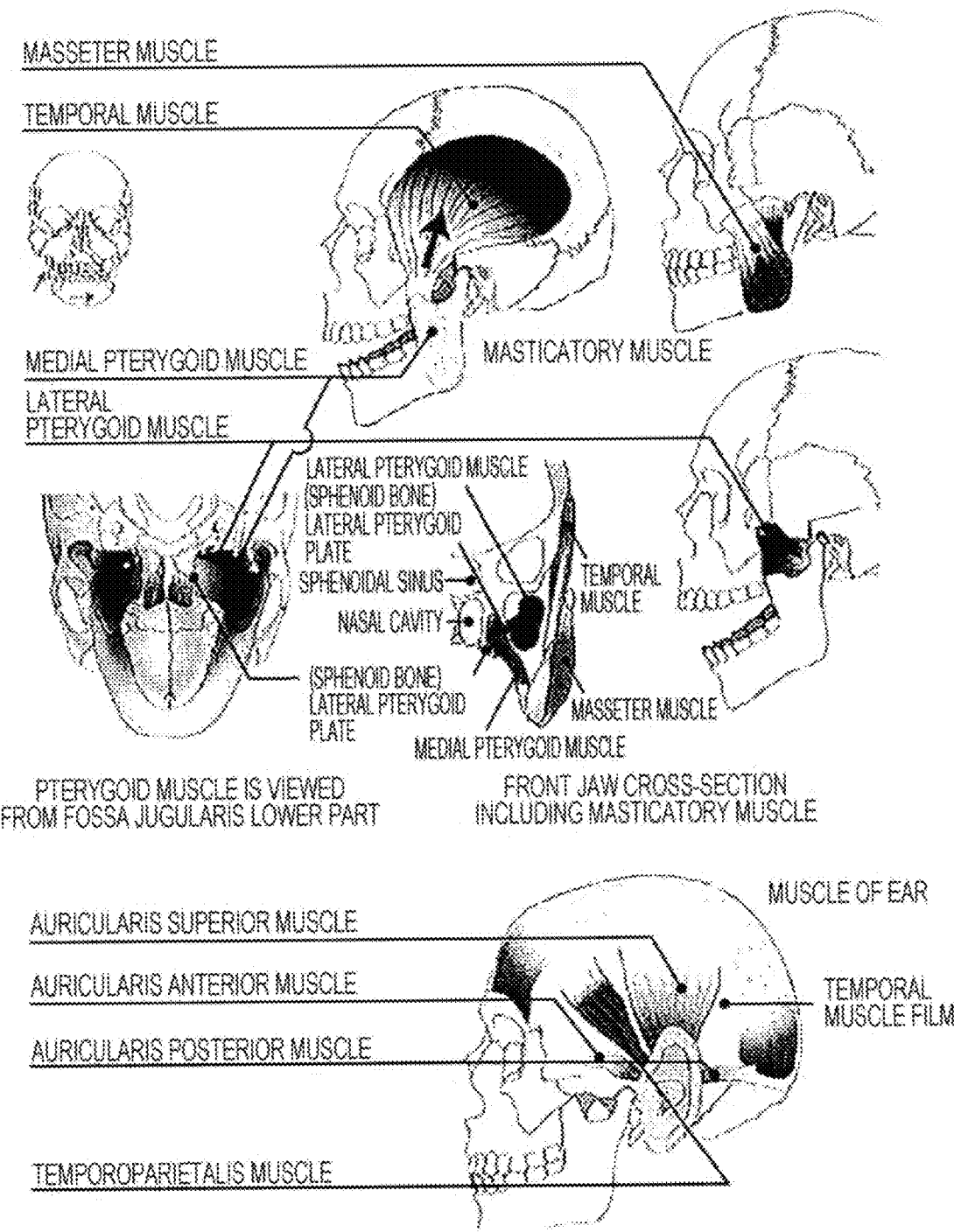
FIG. 27 is a diagram that shows muscles of a masticatory muscle, eyes, teeth, and ear.

However, as shown in FIGS. 23 to 25, a nerve group, a blood vessel group, and a lymph group from the head portion to the head portion are not interposed in a portion (the outline portion passing through the median sagittal plane) with which the inner surface of the hair band 310 comes into contact. Furthermore, as shown in FIGS. 26 and 27, the muscle from the face to the head portion is also not interposed in the portion (the outline portion passing through the median sagittal plane) with which the inner surface of the hair band 310 comes into contact.

Thus, for example, like the first embodiment, compared to the structure in which the head portion is interposed without going through the outline portion passing through the median sagittal plane, the amount of pressing of the hair band 310 to the nerve, the blood vessel system, the lymph system, and the muscle system is suppressed to the minimum. As a result, a migraine or discomfort due to the mounting is greatly relieved.

In addition, FIG. 23 is described in [online] "face nerve" free encyclopedia Wikipedia, [May 27, 2010 search]. Meanwhile, FIGS. 24 and 25 are described in "Color Anatomical Chart" written by F. H. Martini, Nishimura Bookshop, published in 2003, page 8. Meanwhile, FIGS. 26 and 27 are described in "Single Wall" edited by Yoshinori Kawai, NTS publication, $26^{th}$ edition published on Jun. 8, 2007, pages 7 to 8

Meanwhile, the tips of the probe electrodes 320A and 320B (the conductive fiber 321) are protruded to the inner surface of the hair band 310 so as not hinder the fit property of the hair band 310 to the head portion, and thus, a degree of adhesion of the conductive fiber 321 to the head portion is improved.

In general, since the scalp has more sebum secretion and faster metabolism compared skin having a relatively small amount of hair such as the face, a keratinous layer is easily generated. Thus, the cleaning of the scalp is necessary before the mounting of the electrode in the brainwave measurement of the related art.

However, the probe electrodes 320A and 320B have the structure in which a plurality of conductive fibers 321 is implanted to the substrate 322 in an erected state, respectively, and thus, all or a part of the conductive fiber 321 avoids the hair and passes through the sebum and the horny layer, thereby coming into contact with the scalp. Thus, even if the cleaning of the scalp of the electrode is omitted, the brainwave can be measured, and as a result, the burden on the subject is relieved without hindering the substantial measurement accuracy, whereby the brainwave measurement is possible over a long time.

Furthermore, upon mounting the electrode in the brainwave measurement of the related art, there is a necessity for the application of paste so as to hold the contact of the electrode to the scalp.

However, in the probe electrodes 320A and 320B, since the respective conductive fibers 321 are fixed to the substrate 322 in one point, the respective conductive fibers 321 can be moved in the surrounding direction around the fixing point.

For this reason, even if the application of the paste is omitted, the contact of the conductive fiber 321 to the scalp is maintained regardless of the shape of the head. In addition, even if force is applied in any direction due to turning over, the contact of the conductive fiber 321 is maintained while responding to the force, and if the force is dissipated, the original state is rapidly returned to, and the contact of the conductive fiber 321 is maintained.

Figure 28:
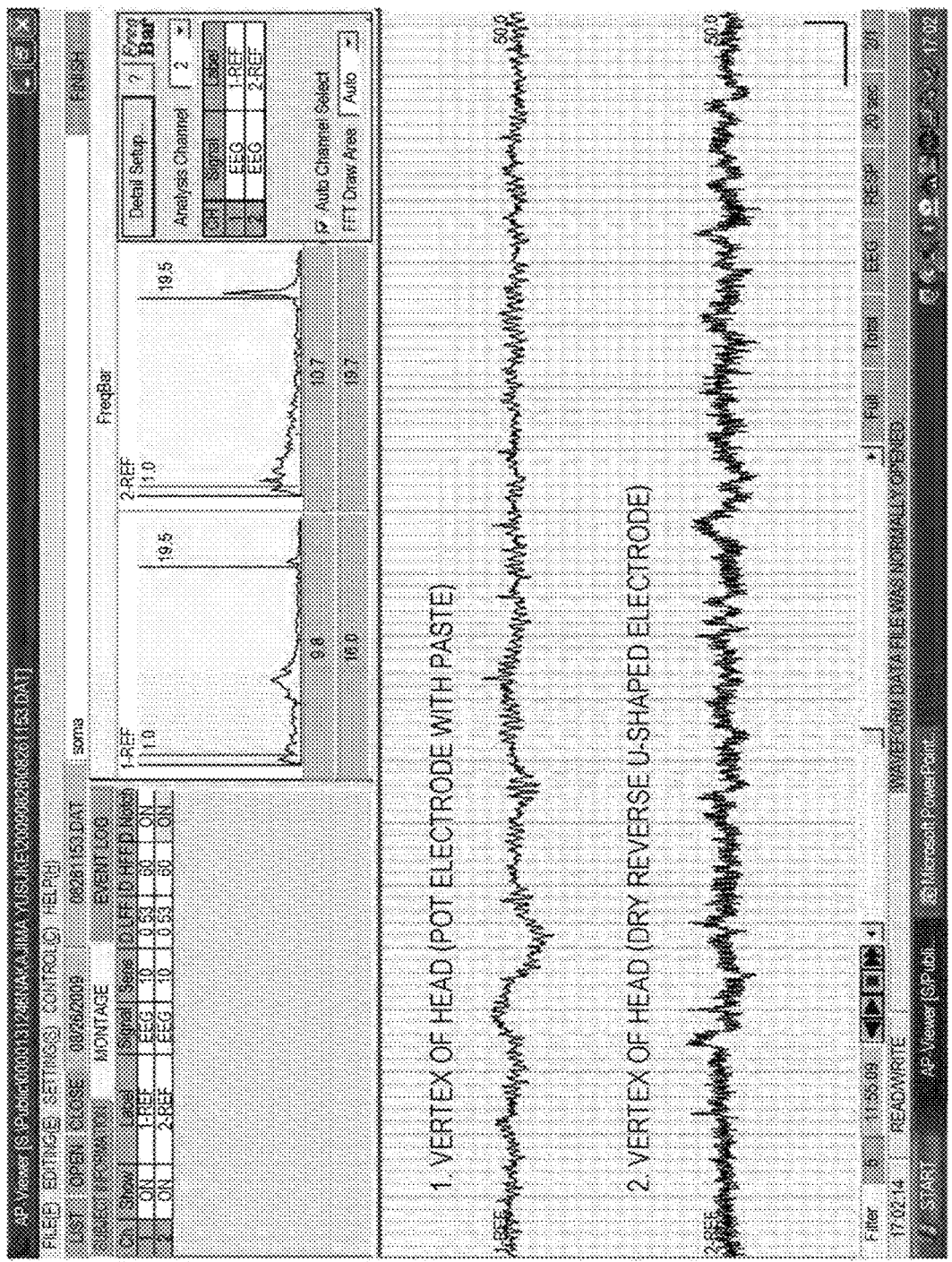
FIG. 28 is a graph that shows a test result.
Figure 29:
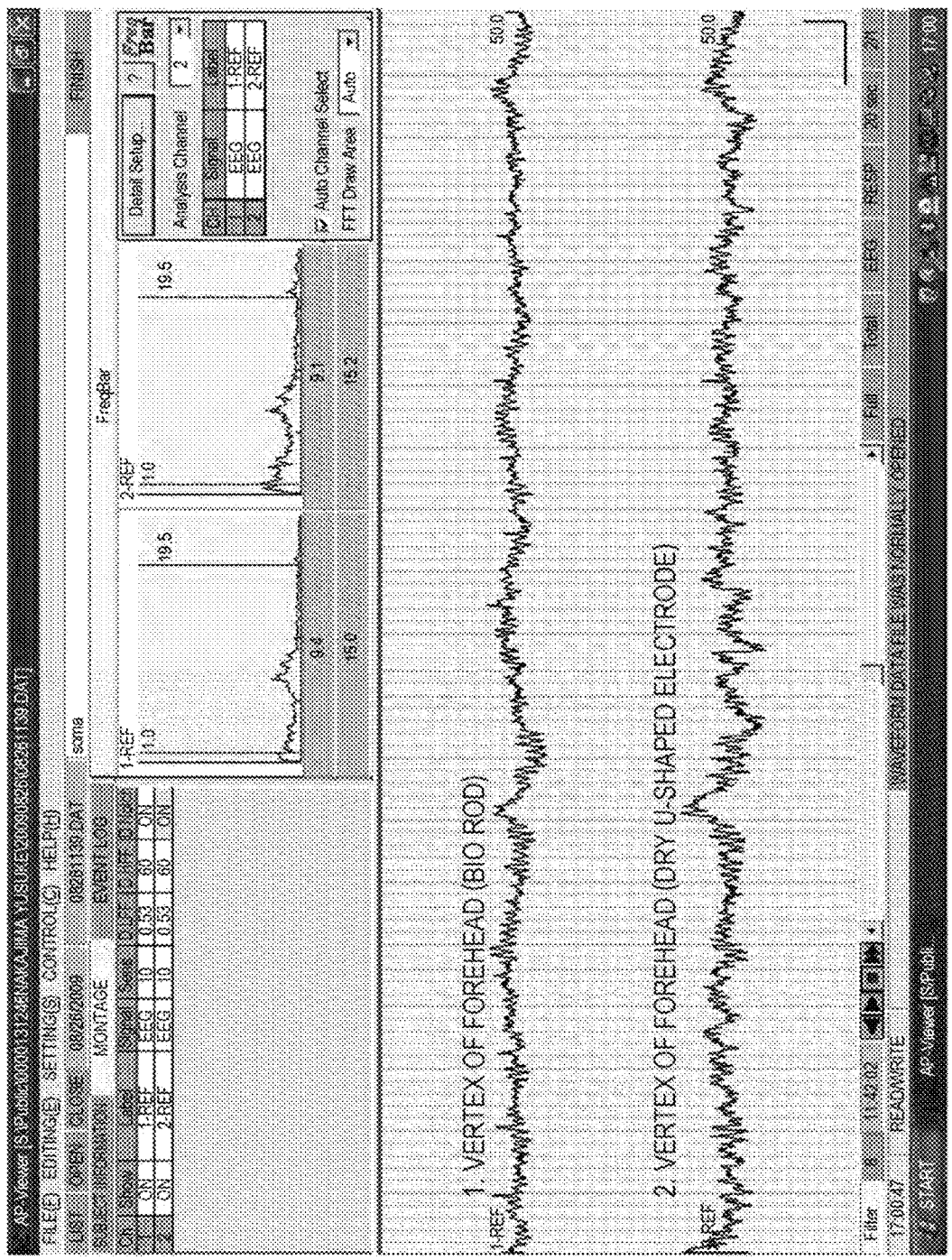
FIG. 29 is a graph that shows the test result.
Figure 30:
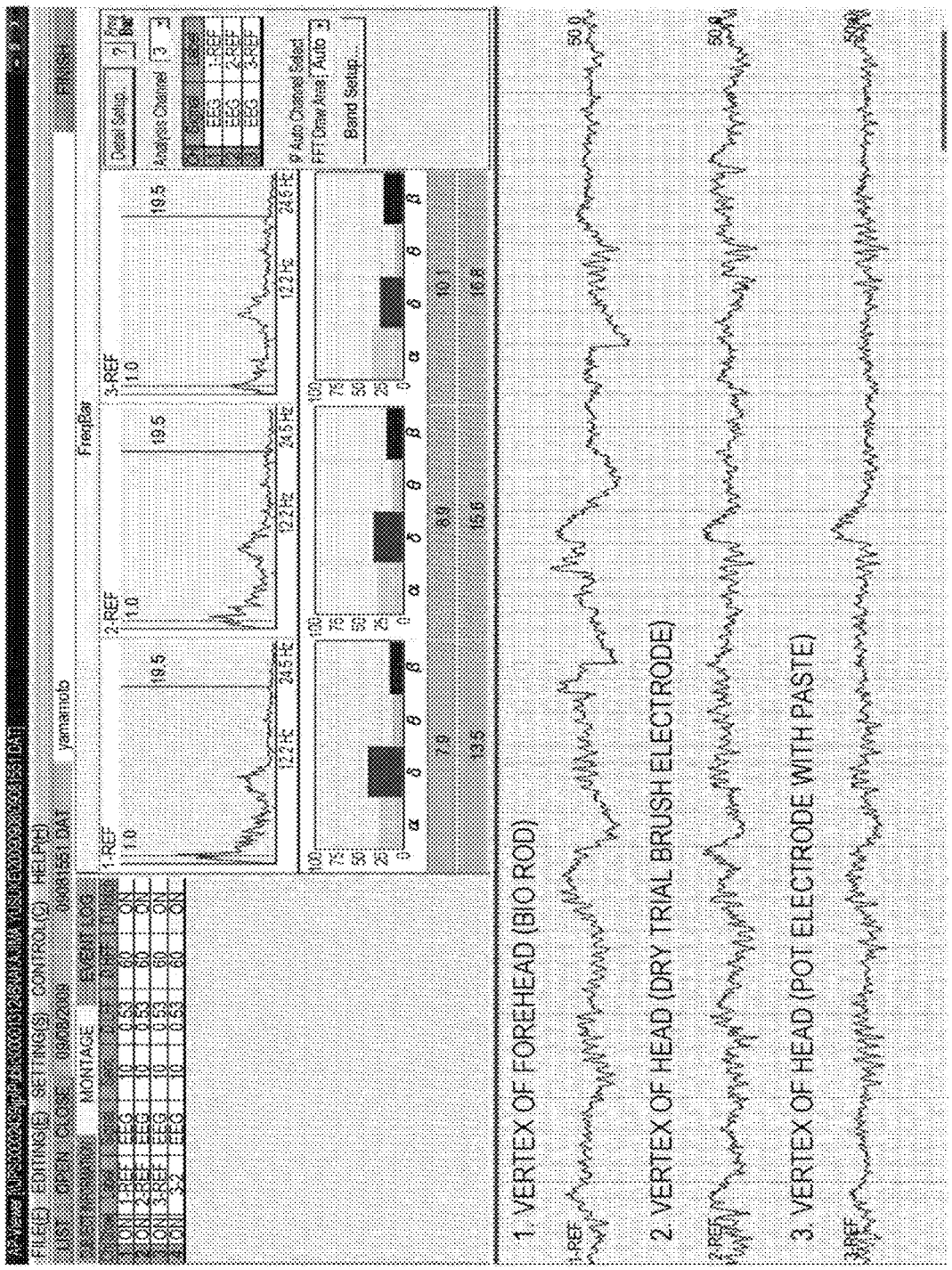
FIG. 30 is a graph that shows the test result.

Herein, the test results are shown in FIGS. 28 to 30. FIG. 28 shows a sensing result of the biological signal in a case where paste is added to the head apex (the median center portion) and a dish-like electrode is added, and a case where a counter U-shaped electrode is added without adding the paste.

FIG. 29 shows a sensing result of the biological signal in a case where a bio rod is disposed and a case where a counter U-shaped electrode is disposed without adding the paste. FIG. 30 shows a sensing result of the biological signal in a case where a bio rod is disposed to the head apex (the median center portion), a case where an electrode (a started probe electrode 320) having a brush structure is disposed without adding the paste, and a case where a counter U-shaped electrode is disposed without adding the paste.

As is apparent from the test results, the electrode having the brush structure (the started probe electrode 320) can obtain the same result as the related art in which the sensing is performed by the disk electrode applied with the paste of the related art, even when the application of the paste is omitted.

In a second step, the position of the occiput contact portion 340 to the head portion is minutely adjusted. That is, the length of the hair band 310 is adjusted by the adjuster portion 330 such that the occiput contact portion 340 is situated immediately above the occiput center portion (Oz in the international 10-20 system). Since the occiput contact portion 340 is disposed so as to avoid contact to the protrusion portion of the head portion, pain to the subject during sleeping is relieved, and, as a result, sleeping hindrance to the subject is greatly reduced.

Furthermore, the angle of the occiput contact portion 340 is adjusted by the angle adjustment mechanism 342 (FIG. 18) such that the inner surface of the occiput contact portion 340 is approximately parallel to the contact surface of the head portion. Thus, the stability to the head portion can be enhanced.

In a third step, a hair clip (not shown) or a sucker (not shown), which is attached to the occiput contact portion 340 in a freely attachable and detachable manner, is mounted to the hair or the scalp. Thus, the stability to the hair portion is further enhanced regardless of the presence or the absence of the hair.

In a fourth step, the shapes of the arms 380A and 380B are suitably changed so that the tips thereof are situated in the earlobe along the head portion via the ear back, and the shapes of the arms 380C and 380D are suitably changed such that the tips thereof are situated in the temple along the face.

Since the respective arms 380 are formed in the cylindrical shape by a soft material and an inner portion thereof is added with a rigid line-shaped member (not shown), the shape of the arm 380 can be flexibly adjusted to the subject, and the state after the adjustment can be held.

In a fifth step, the earlobe attachment portions 390A and 390B provided at the tips of the arms 380A and 380B are attached to the earlobe, and the temple attachment portions 401A and 410B provided at the tips of the arms C and 380D are attached to the temple.

The earlobe attachment portions 390A and 390B have the structure in which the earlobe is interposed between the magnets 394A and 394B and the reference electrodes 370A and 370B, and thus, the stability and the adhesion between the reference electrodes 370A and 370B to the earlobe can be ensured. Furthermore, it is possible to rapidly fix the reference electrodes 370A and 370B to the subject.

The temple attachment portions 410A and 410B have a sheet having stickiness to the skin attached to the margins of the frames 411A and 411B, and thus, the stability and the adhesion of the probe electrodes 400A and 400B to the temple can be ensured. Furthermore, it is possible to rapidly fix the reference electrodes 370A and 370B to the subject.

In a sixth step, the jaw can be covered with the case 501. The case 501 is formed with a surface (the chin ridge facing surface) 502 corresponding to the shape of the chin ridge in a lower jaw. For this reason, the chin ridge can be easily fitted to the subject by the shape of the chin ridge facing surface 502 by touch without seeing a mirror or the like, and the stability of the fitted state can be promoted.

In a seventh step, the arms 534A and 534B are stretched, and the shapes of the arms 380A and 380B are suitably changed so as to follow the face on the lower jaw angle portion. The arms 534A and 534B are formed in the cylindrical shape by a soft material and the inner portions thereof are added with a rigid line-shaped member (not shown), it is possible to flexibly adjust the shape of the arm 534 to the subject and the state after the adjustment can be held.

In an eighth step, pin-like connectors of the tips of the arms 534A and 534B are inserted into a jack-like connector of the arm earlobe attachment portion 390A. The arm 534 is connected to the stopper 532, which is fixed near the opposite side of the left and the right of the arm 534 of the guide groove 531 of the rail 530, via the spring 533.

Thus, the arm 534 is adjusted to the length corresponding to the distance between the jaw brace 500 and the earlobe attachment portion 390A by the spring 533, and the position deviation of the jaw brace 500 is prevented by the mutually contradictory pressure of the spring 533 and is stabilized.

Figure 31:
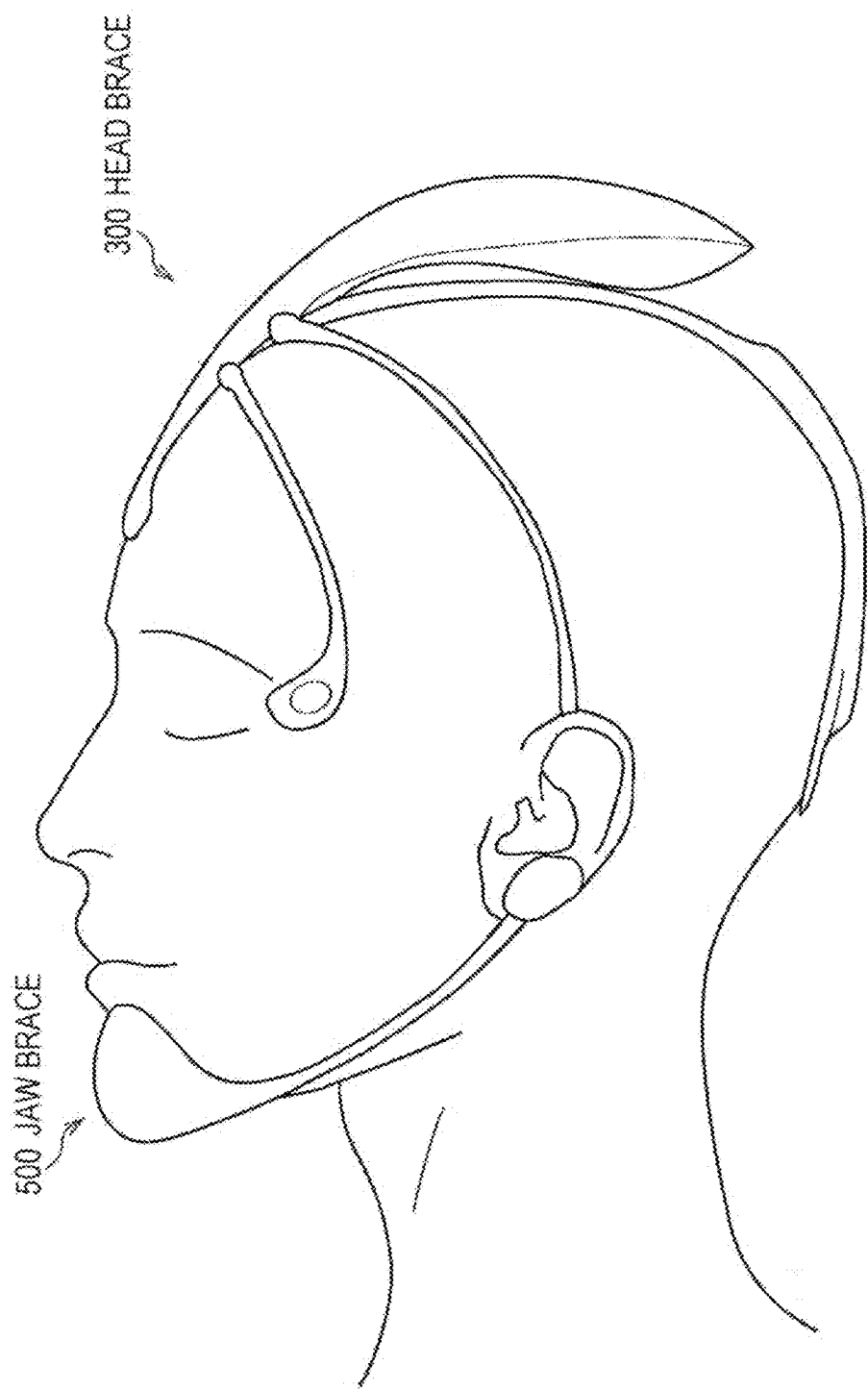
FIG. 31 is a diagram that schematically shows a mounting state of the biological signal measuring equipment.

By going through the mounting sequence mentioned above, for example, as shown in FIG. 31, the head brace 300 and the jaw brace 500 are mounted on the head portion and the jaw. As a result, the probe electrodes 320A and 320B are fixed to the scalp, the probe electrodes 400A and 400B are fixed to the temple, the reference electrodes 370A and 370B are fixed to the earlobe, and the probe electrodes 510A and 510B are fixed to the chin ridge, respectively. However, the mounting sequence mentioned above is merely an example, and the mounting sequence is not limited to the above mounting sequence.

3-3. Configuration of Measurement Portion

Figure 32:
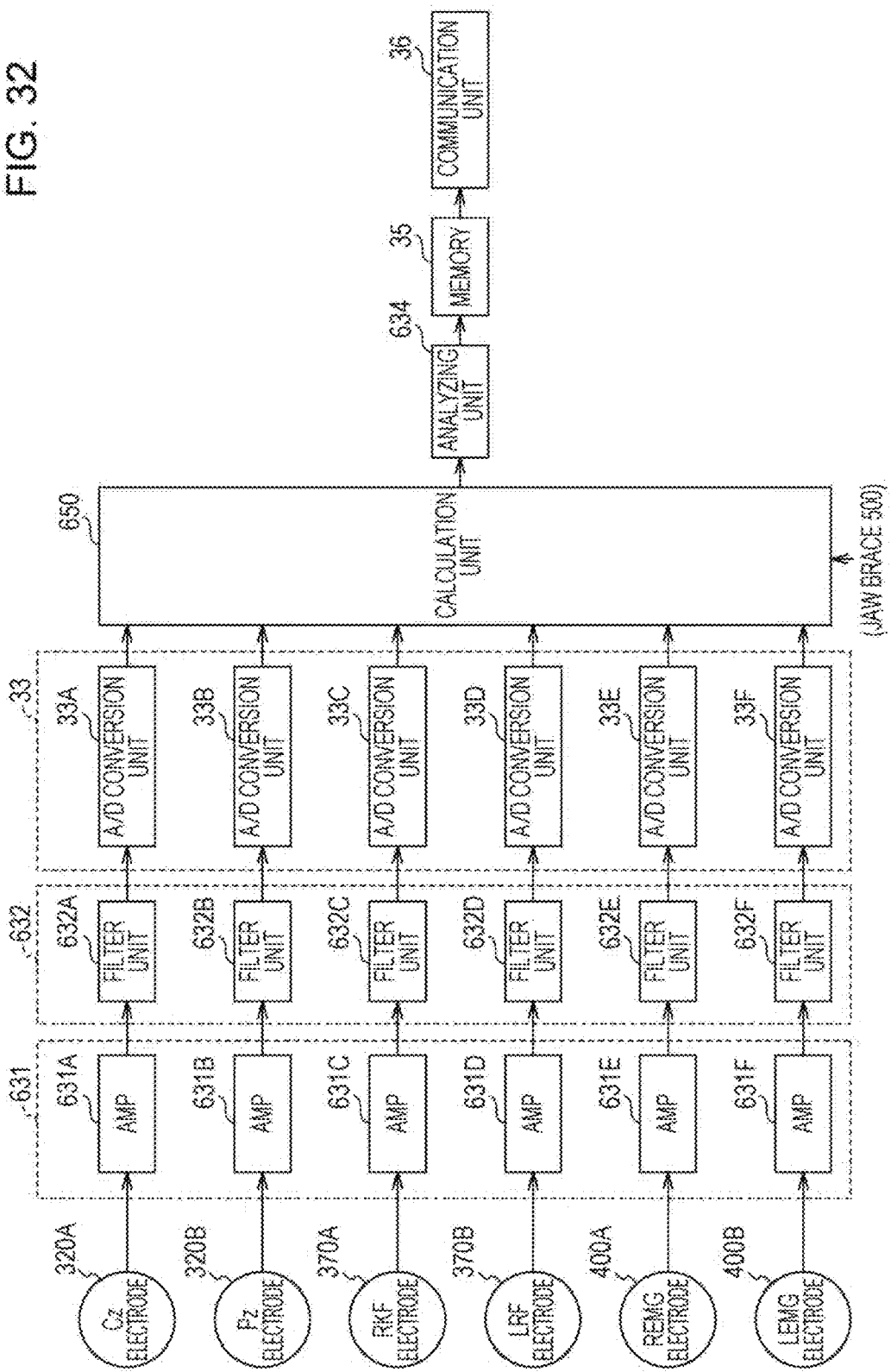
FIG. 32 is a diagram that schematically shows a circuit configuration of a measurement portion.

In FIG. 32 in which the corresponding portions of FIG. 4 are denoted by the same reference numerals, a configuration of the measurement portion 600 is shown. The measurement portion 600 has a configuration that includes an amplification portion 631, an A/D conversion portion 33, a filter portion 632, a calculation portion 650, an analyzing portion 634, a memory 35, and a communication portion 36.

The amplification portion 631 has amplifiers 631A to 631F allocated to the respective electrodes 320, 370, and 400 and amplifies the difference between the electrodes 320, 370, and 400 and the reference potential (the ground point).

The filter portion 632 is a digital filter and thus is not different from the filter portion 32 that is an analog filter. The filter portion 632 has filter portions 632A to 632F allocated to the respective electrodes 320, 370, and 400. Thus, the filter portion 632 can obtain the conversion result in the A/D conversion portions 33A to 33F after removing the signal component other than the set frequency band.

Specifically, a band pass filter which selects the frequency band of the brainwave, a notch filter which removes the AC noise, the combination thereof or the like are preferable.

However, since the measurement equipment is disposed in a room different from the mechanism to be attached to a subject in the sleeping polygraph examination, the distance between the mechanism and the measurement device is necessarily enlarged. Thus, in the sleeping polygraph examination of the related art, a shield room is essential so as to avoid influence such as a disturbance noise overlapped with the connection line between the mechanism and the measurement device.

However, the position where, the fixing region 361 in the protrusion case 360 is disposed, is a position where each of the electrodes 320, 370, and 400 are in the shortest distance relationship to the position, and the ground lines of the amp allocated to the electrodes 320, 370, and 400 are concentrated in one point in the fixing region 361. For this reason, the influence of the noise is greatly reduced even when there is no shield room, and, as a result, the brainwave measurement becomes possible even in an ordinary house.

When the brainwave measurement becomes possible in an ordinary house, various disturbance noises are present. Typically, there is a noise generated from a receptacle. For example, since the frequency band of the noise generated from the receptacle is different from each region, for example, Tokyo, Kansai or the like, the frequency bands necessary to be removed by the filter portion 632 are different from each other.

However, in the analog filter shown in FIG. 4, since it is difficult to switch over the frequency band necessary to be removed by one filter, there is a necessity for the filter of the number of the frequency band necessary to be removed. On the other hand, the filter portion 632 in the measurement portion 600 is a digital filter, and thus the filter portion 632 can be included in the calculation portion 650, and the switch-over of the frequency band necessary to be removed can be executed by the programming by the use of one DSP capable of being subjected to the pipeline treatment.

Thus, even if the brainwave measurement is possible in an ordinary house, the filter portion 632 can correctly remove the frequency band becoming the disturbance noise by a minimum solid number, and, as a result, the measurement accuracy can be improved.

Figure 33:
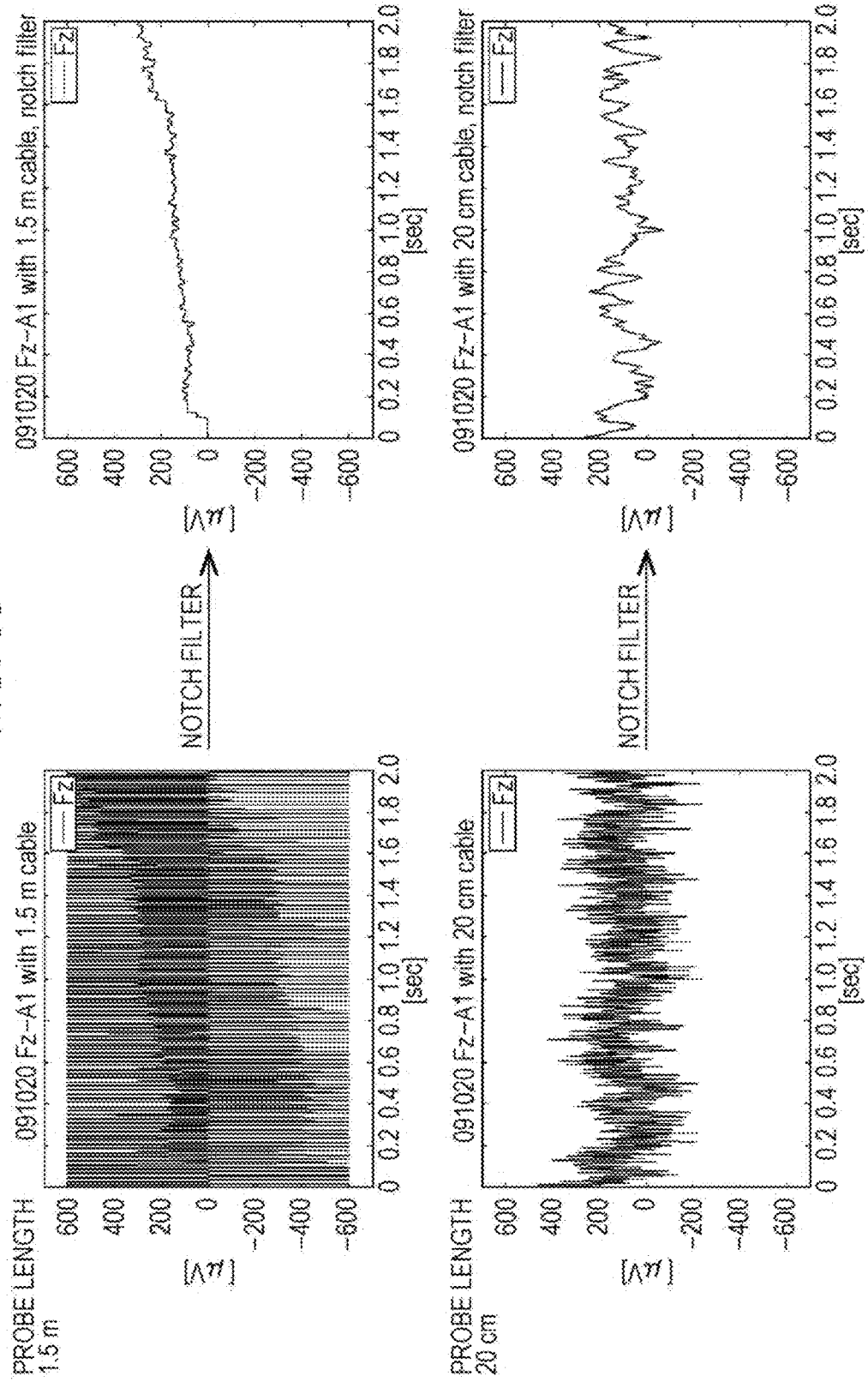
FIG. 33 is a graph that shows a test result.

Herein, the test result is shown in FIG. 33. An upper stage of FIG. 33 is the case of the measurement other than the shield room by the use of the cord having the same cable length (1.5 [m]) as that in the brainwave of the related art. In this case, the biological signal is saturated by AC noise, and the biological signal is embedded in the noise even if a notch filter is provided.

Meanwhile, a lower stage of FIG. 33 is the case of the measurement using the cord having the same cable length (0.2 [m]) as that in the head brace 300. In this case, the AC noise has the same amplitude as the biological signal, and the biological signal appears by applying the notch filter.

In addition, since the distance between the probe electrodes 510A and 510B and the fixing region 361 in the jaw brace 500 is longer than other electrodes 320, 370, and 400, the probe electrodes are connected to the amp in the jaw brace 500 separately from the fixing region 361. Thus, the influence of the noise to the biological signal sensed by the probe electrodes 510A and 510B does not substantially become a problem.

The calculation portion 650 takes the difference between the outputs of the filter portions 632A and 632B allocated to the probe electrode 320 and the output of the filter portion 632A or 632B allocated to the reference electrode 370, and outputs the result to the rear stage.

Furthermore, the calculation portion 650 takes the difference between the outputs of the filter portions 632E and 632F allocated to the probe electrode 400 and the output of the filter portions 632A and 632B allocated to the reference electrode 370, and outputs the result to the rear stage.

In addition, the result, in which the difference between the probe electrodes 510A and 510B and the reference potential (ground point) in the electronic circuit 520 to be disposed in the case 501 of the jaw brace 500 is amplified and the filter treatment is performed, is input to the calculation portion 650 via the arms 534A and 534B and the connectors 392A and 392B, respectively.

The calculation portion 650 takes the difference between the output from the connectors 392A and 392B corresponding to the probe electrodes 510A and 510B and the output of the filter portions 632A and 632B allocated to the reference electrode 370, and outputs the result to the rear stage.

In this manner, the calculation portion 650 takes the difference between the output corresponding to the probe electrodes 320, 400, and 510 and the output corresponding to the reference electrode 370. This is because the amplification portion 631 does not amplify the potential difference between the reference electrode and the probe electrode but amplifies the difference between the respective electrodes 320, 370, and 400 and the standard point to be common.

The analyzing portion 634 determines the starting time, the ending time, and the quality of the REM sleep by the use of the muscle potential of the jaw that is sensed by the probe electrodes 510A and 510B, in addition to the muscle potential of the eye that is sensed by the probe electrodes 400A and 400B.

In general, during REM sleep, the muscle strength of the jaw is relatively weakened compared to the time other than the REM sleep. Thus, the determination accuracy is further improved compared to the analyzing portion 34 which determines the starting time, the ending time, and the quality of the REM sleep only by the muscle potential of the eye to be sensed by the probe electrodes 400A and 400B.

4. Another Embodiment

In the first embodiment mentioned above, the hair band 2 was mounted so as to interpose the left and right side portions of the head. However, the mounting method is not limited thereto. For example, it is also possible to mount the hair band 2 so as to interpose the front and rear side portions of the head.

In the first embodiment mentioned above, as the components of the biological signal measuring equipment 1, the hair band 2, the reference electrode 12, and the probe electrode 13 were applied. However, the components of the biological signal measuring equipment 1 are not limited to the shapes, the structures or the like shown in the embodiment mentioned above.

Figure 34:
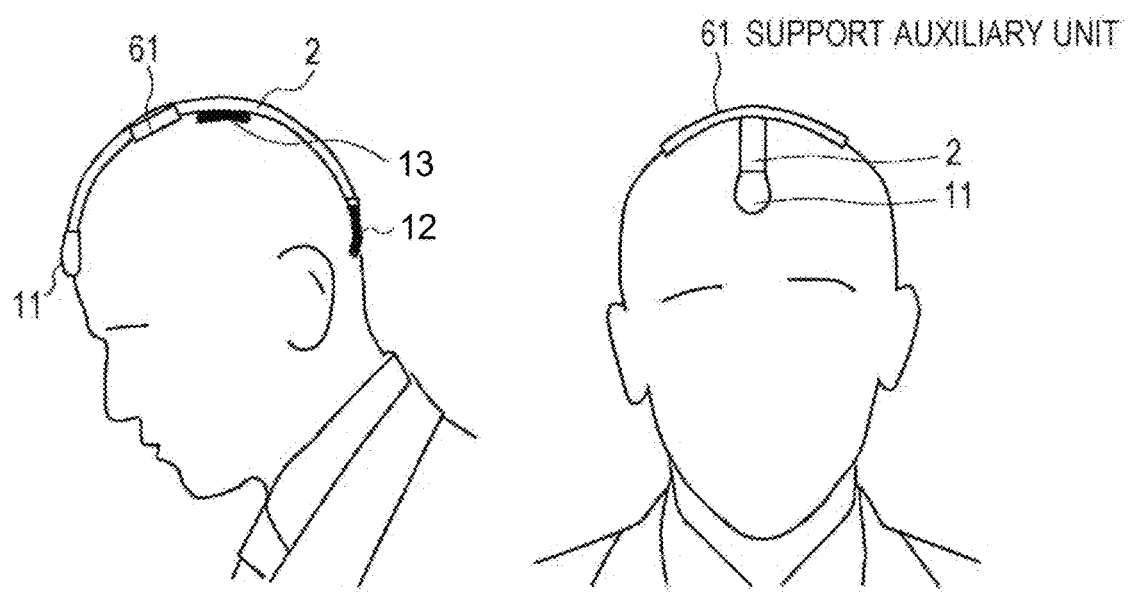
FIG. 34 is a diagram that schematically shows a mounting state of a biological signal measuring equipment in another embodiment.

For example, as shown in FIG. 34, it is possible to apply a biological signal measuring equipment 60 in which a support auxiliary portion 61, which has a gradual curvature further than the hair band 2 and has a length shorter than the whole length of the hair band 2, is connected to the curved apex portion of the hair band 2 in a direction perpendicular to the hair band 2.

Since the hair band 2 of the biological signal measuring equipment 60 interposes the front and rear side portions of the head like the hair band 310 of the head brace 300, the structure thereof is similar to the hair band 2 of the biological signal measuring equipment 1 which interposes the left and right side portions of the head, but has a different shape.

Specifically, the hair band 2 of the biological signal measuring equipment 1 is symmetrical (left and right symmetry) based on the position having the greatest curvature to be brought into contact with the vertex, and the length from the position to each end portion is about the same. Furthermore, the height position of both end of the hair band during mounting is approximately the same.

On the other hand, like the hair band 310 of the hair portion equipment 300, the hair band 2 of the biological signal measuring equipment 60 is asymmetrical (front and rear asymmetry) based on the position having the greatest curvature to be brought into contact with the vertex, and the length to the front end portion in this position is shorter than the length to the rear end portion in this position. Furthermore, the height positions of both ends of the hair band 2 during mounting is a positional relationship in which the reference electrode 12 as the occiput contact portion is lower than the non-slip portion 11 as the forehead contact portion.

The length of the support auxiliary portion 61 is a length in which the end portion of the support auxiliary portion 61 is situated in "C3" and "C4" parts in the international 10-20 system.

When applying the biological signal measuring equipment 60, the front and rear direction of the head portion is interposed by four points of two points of the jaw and the occiput portion in the head portion and two points of "C3" and "C4" in the international 10-20 system, and the head portion can be supported. Thus, compared to the biological signal measuring equipment 1, the position deviation of the electrodes 12 and 13 to the scalp can be reduced.

Furthermore, the width of the hair band 2 of the biological signal measuring equipment 60 has the length smaller than the distance between "C3" and "C4" in the international 10-20 system, and the length of the support auxiliary portion 61 is about the same as the distance. Thus, in the biological signal measuring equipment 60, a migraine or discomfort due to a subject lying down is greatly relieved, the pressing amount to the nerve, the blood vessel system, the lymph system, and the muscle system is suppressed to the minimum, and the migraine or discomfort due to the mounting is greatly relieved.

In addition, the shapes of the hair band 2 and the support auxiliary portion 61 of the biological signal measuring equipment 60 are not limited to the plate shape, and for example, the shapes may be a tubular shape having a circular or elliptical cross-section of a hollow or a solid, and other shapes may be adopted.

Additionally, in the case of adopting the tubular shape having the elliptical cross-section, the surface of the long diameter direction is a surface to be brought into contact with the head portion surface from the viewpoint of relieving the migraine or the discomfort or the like. Furthermore, the probe electrode 13 may be provided in one end or both ends of the support auxiliary portion 61.

Figure 35:
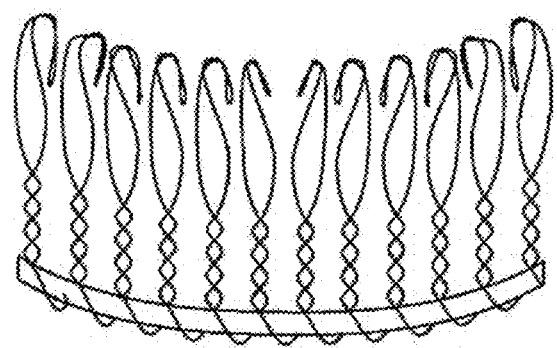
FIG. 35 is a diagram that schematically shows a configuration of an electrode in another embodiment.

As another example, instead of the reference electrode 12 or the probe electrode 13, as shown in FIG. 35, a reference electrode or a probe electrode can be applied in which a tooth tip is folded back. In the case of applying the electrode, compared to the reference electrode 12 or the probe electrode 13, a degree, by which each tooth is entangled in the hair root, is increased, and thus, the position deviation can further be reduced while further improving the adhesion of the teeth to the scalp.

As another example, the teeth support rods 12B and 13B in the reference electrode 12 and the probe electrode 13 are omitted, and the teeth portions 12A and 13A in the probe electrode 13 and each reference electrode 12 may be directly fixed to the inner surface of the hair band 2.

In addition to the examples mentioned above, the components of the biological signal measuring equipment 1 are not limited to the shapes, the structures or the like shown in the embodiments mentioned above, and can be changed within the scope not departing from the object of the present invention.

In the second embodiment mentioned above, the reference electrode 57 was mounted on the earlobe. However, the mounting position of the reference electrode 57 is not limited to the present embodiment. For example, the auricle upper part or the temple position can be the mounting position.

In the second embodiment mentioned above, as the components of the biological signal measuring equipment 50, the hair band 51, the arm 52, the snap button 53, the electrode supporter 54, the reference electrode 55, and the probe electrode 57 were applied. However, the components of the biological signal measuring equipment 50 are not limited to the shapes, the structures or the like shown in the embodiments mentioned above.

Figure 36:
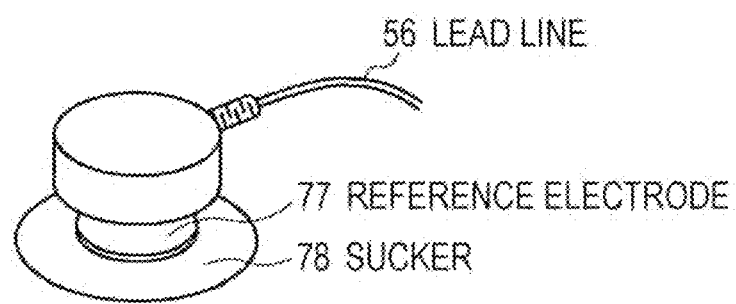
FIG. 36 is a diagram that schematically shows an electrode structure in another embodiment.

For example, instead of the reference electrode 57, as shown in FIG. 36, it is also possible to adapt an electrode structure in which the reference electrode 77 is formed as the concave portion and the sucker 78 surrounding the same. In addition, like an electrode used in the electrocardiogram, it is also possible to adopt an electrode structure in which the tube is attached to a bay-like electrode. Of course, an electrode structure other than the sucker may be adopted.

As another example, a form may be adopted in which one of the arms 52A and 52B and the snap buttons 53A and 53B is deleted.

In addition to the examples mentioned above, the components of the biological signal measuring equipment 50 are not limited to the shapes, the structures or the like shown in the embodiments mentioned above and can be changed in the range not departing from the object of the present invention.

In addition, a form may be applied in which the components of the biological signal measuring equipment 1 in the first embodiment are suitably combined with the biological signal measuring equipment 50 in the second embodiment.

Figure 37:
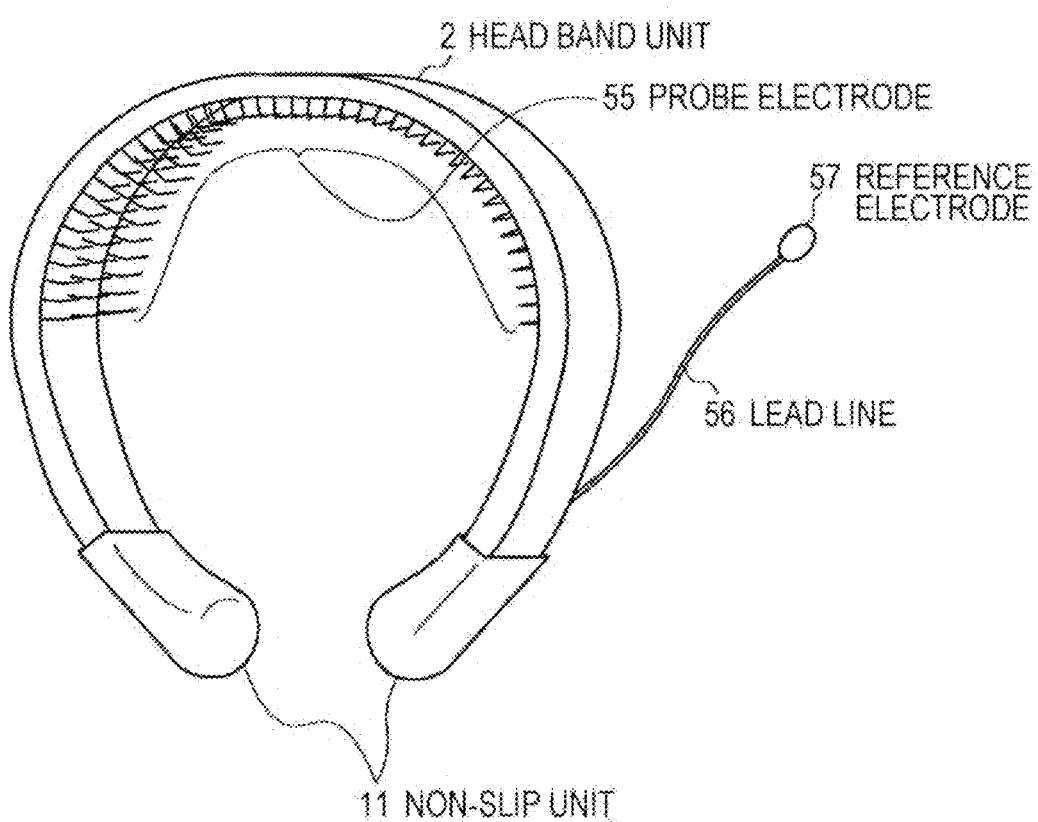
FIG. 37 is a diagram that schematically shows a configuration of a biological signal measuring equipment in another embodiment.

For example, a biological signal measuring equipment 80 shown in FIG. 37 can be applied in which the portions corresponding to FIG. 1 or 5 are denoted by the same reference numerals. In the biological signal measuring equipment 80, the reference electrode 12 provided in the other end of the hair band 2 is changed to the non-slip portion 11, and the reference electrode 57 is provided at the tip of the lead line 56 drawn from the inner portion of the hair band 2. Furthermore, in the hair band 2, the probe electrode 55 is provided instead of the probe electrode 13.

Figure 38:
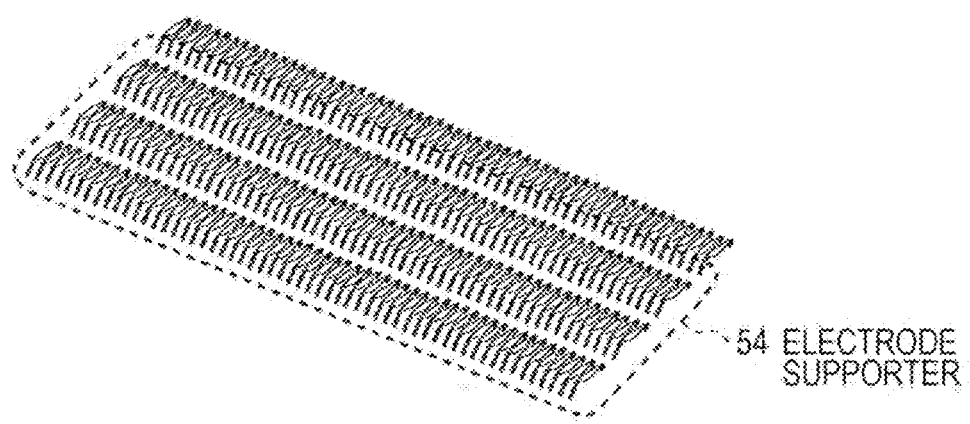
FIG. 38 is a diagram that schematically shows a configuration of an electrode in another embodiment.
Figure 40:
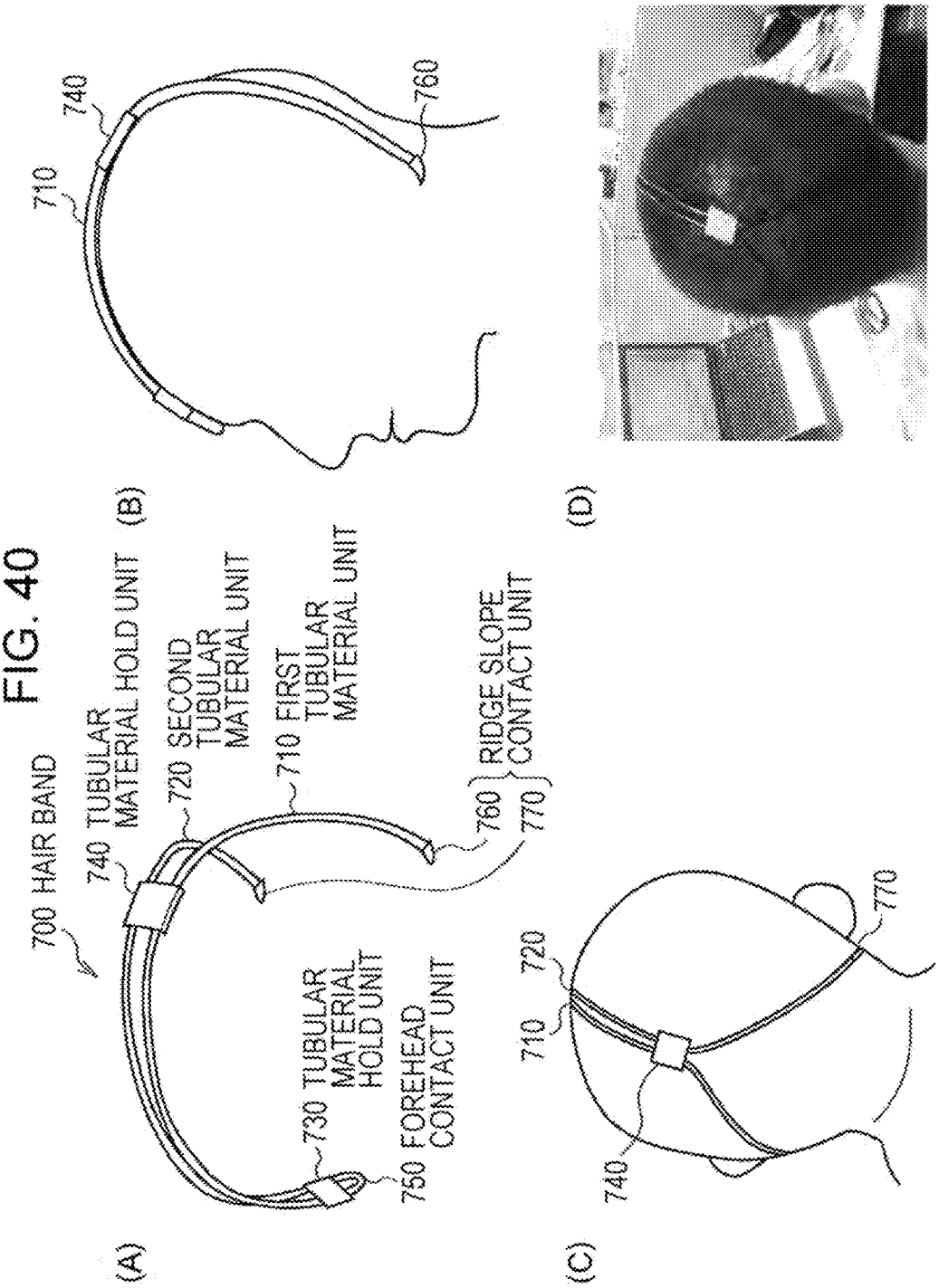
FIGS. 40A to 40D are diagrams that schematically show a hair band and a mounting state thereof in another embodiment.
Figure 41:
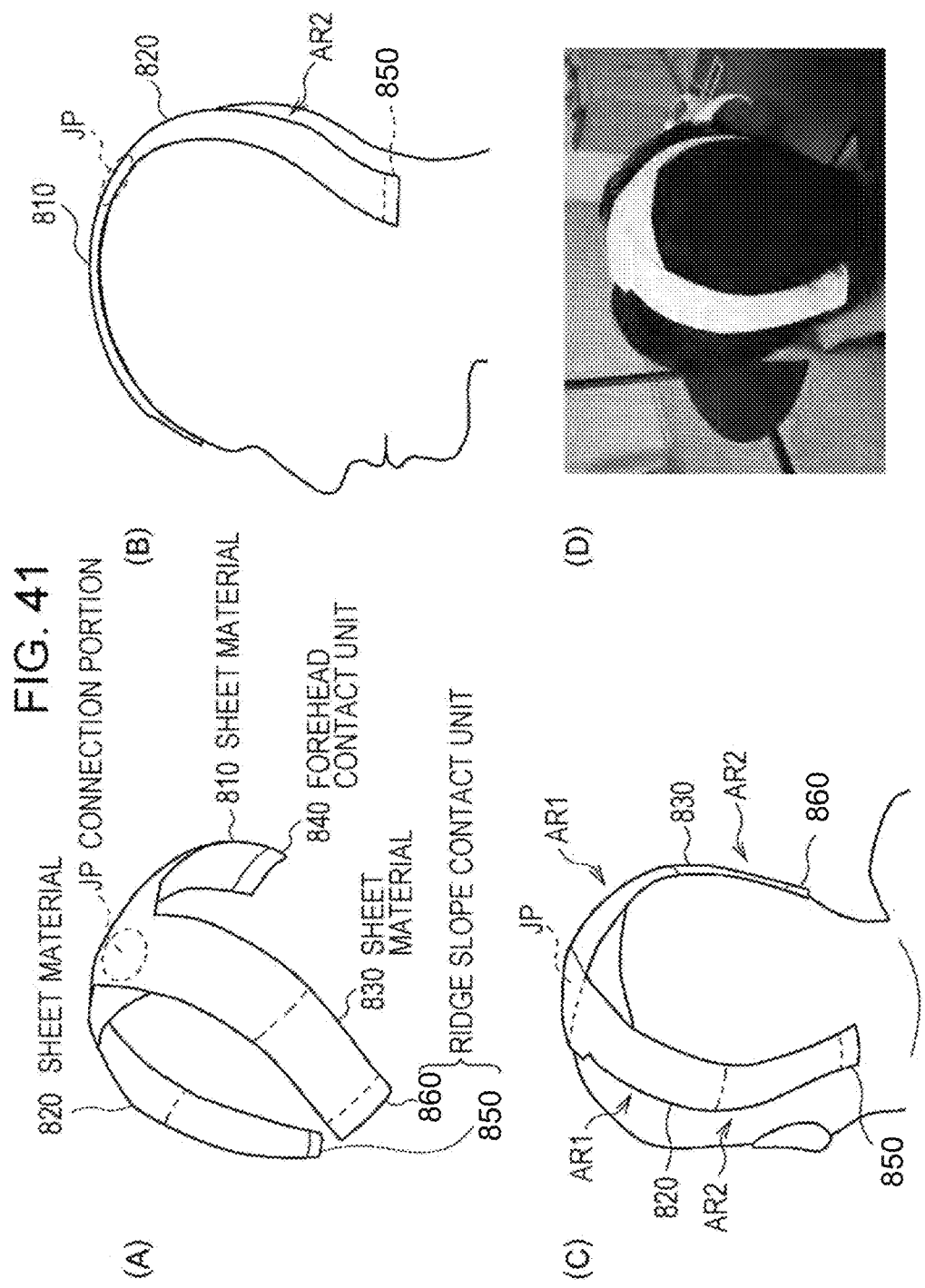
FIGS. 41A to 41D are diagrams that schematically show a hair band and a mounting state thereof in another embodiment.

As another example, each tooth of the probe electrode 55 shown in FIG. 5 may be applied as each tooth of the probe electrode 13 shown in FIG. 1. In this case, as shown in FIG. 38, in regard to a portion (a twisted portion (see FIG. 2)) formed as a rod shape among the teeth in the probe electrode 13, the root is fixed in the state of being diagonally facing the surface of the electrode supporter 54, and, a portion (see FIG. 2) formed as a ring shape faces the surface in parallel. In this case, the contact surface to the scalp can be increased. Furthermore, when the electrode supporter 54 is mounted on the vertex, force, by which the arm 52 tends to return to the original arm length, acts on the surface facing the head portion of the electrode supporter 54, as force to be pressed to the vertex. Further, force, by which the ring shape portion of the probe electrode shown in FIG. 38 tends to return to the original state, acts as force to be pressed to the vertex. Thus, the adhesion of the scalp can be further enhanced. In addition, the structure, which presses the surface facing the head portion against the head portion, can also be applied to a structure other than the structure shown in FIG. 5.

The biological signal measuring equipment 80 shown in FIG. 37 is merely an example of the combined form and can also be applied to another combined form.

In the third embodiment mentioned above, the probe electrodes 320A and 320B had the brush structure. However, the structure of the brush electrode is not limited to the embodiment. For example, the structures shown in FIG. 2, 6 or 35 can be applied.

In the third embodiment mentioned above, the adjuster portion 330 was provided between the concave portion 312 and the rear end portion of the hair band 310. However, the installation place of the adjuster portion 330 in the hair band 310 is not limited to the embodiment. For example, the adjuster portion 330 can be provided between the concave portion 311 and the concave portion 312, or between the concave portion 311 and the fixing region 361 in the protrusion case 360. However, from the viewpoint that the tip position is disposed at a position immediately above the O point, the embodiment mentioned above is preferable. In addition, the adjuster portion 330 may be omitted from the hair band 310.

In the third embodiment mentioned above, the sliding type adjuster portion 330 was provided. Instead of this, the hair band 310 itself is formed of a material having elasticity, and the side of the hair band 310 is provided with a rim having rigidity, whereby the hair band 310 itself can adjust the length of the longitudinal direction.

In the third embodiment mentioned above, the button 363 is provided on the upper surface of the protrusion region 362, and the connector 364 was provided on the side of the protrusion region 362. The installation places of the button 363 and the connector 364 are not limited to the present embodiment, and various places can be applied.

In the third embodiment mentioned above, the button 363 of the type was adopted in which the power source is turned on or off by the push operation for some seconds. However, the type of turning the power source on or off is not limited to the present embodiment.

For example, a slide type can be adopted. As another example, the button type of turning the power source on or off by the push operation may be provided in a concave state compared to the upper surface of the protrusion region 362. In brief, a type may be adopted in which the power source is prevented from being erroneously turned on or off during sleep or waking in advance.

In the third embodiment mentioned above, the lengths of the arms 380 and 534 were fixed. However, like the hair band 310 mentioned above, the slide type adjuster may be provided, and the arms 380 and 534 themselves may adjust the length of the longitudinal length.

In the third embodiment mentioned above, the amplification portion 631 was adopted which amplifies the respective electrodes 320, 370, and 400 and the ground point common to the amplification portion 631. However, an amplification portion may be adopted which amplifies the difference between the probe electrodes 320A and 320B and the reference electrodes 370A or 370B, the difference between the probe electrode 400A and the reference electrode 370A, and the difference between the probe electrode 400B and the reference electrode 370B. Furthermore, the reference electrodes 370A and 370B of the ear may be used as the reference of the whole measurement portion. Even in this case, it is confirmed that the measurement sensitivity is obtained to the extent that substantially the measurement is difficult.

In addition to the embodiment mentioned above, the components of the head brace 300 and the jaw brace 500 are not limited to the shapes, the structure or the like shown in the third embodiment mentioned above, and can be changed in the scope not departing from the object of the present invention.

In the first to third embodiments mentioned above, the electrode is directly pressed to the human body surface, but a contact medium such as water, alcohol, oil or glycerin for effectively transferring the wave motion may be applied to the electrode. In addition, a configuration may be adopted which is provided with a mechanism allowing the contact medium to flow in the electrode.

For example, it is possible to adopt a configuration in which a container is provided which accumulates the contact medium in the hair band 2, the electrode supporter 54, and the protrusion region 362, a needle-like tube member allowing the contact medium to flow in the electrode is connected to the valve provided in the container, and the tip of the tube member is disposed in one end portion of the electrode.

In the first to third embodiments mentioned above, the measurement target was the brainwave, but the body temperature or the pulse may be applied. In this case, for example, an optical type body temperature sensor or pulse sensor is provided in the pieces of biological signal measuring equipment 1 and 50, the head brace 300 or the jaw brace 500, and the signals given from the sensors are given to the analyzing portion 34 via the A/D conversion portion 33. The analyzing portion 34 memorizes the body temperature data or the pulse data in the memory 35 in association with the brainwave data. The association can be used as an index that specifies sleep disorders and illness.

The supporter (the hair band), which is interposed in the front and rear direction of the head portion by using the portion to be brought into contact with the jaw and the portion to be brought into contact with the occiput as the ends and is supported by the head portion, is not limited to the hair band 2 of the biological signal measuring equipment 60 and the hair band 310 of the head brace 300. For example, the hair band 600 shown in FIGS. 39A to 39C can be applied.

Stoppers of resin such as rubber are fitted to both ends of the hair band 600, and formed as the occiput contact portion 620 and the jaw contact portion 610. The hair band 600 is formed of a tube line-shaped plastic material or a metallic material (hereinafter, also referred to as a wire-shaped tube member) of a circle or an ellipse having a hollow or solid cross-section, and is formed in the shape of C.

Specifically, there is asymmetry (the front and rear asymmetry) based on the position having the greatest curvature to be brought into contact with the vertex, and the length from the position to the front end portion is shorter than the length from the position to the rear end portion. Furthermore, the height positions of both ends of the hair band 600 during mounting is in a positional relationship in which the occiput contact portion 620 of the rear side is lower than the jaw contact portion 610 of the front side.

Thus, the hair band 600 is flexibly fitted regardless of the shape of the head portion, and that state can be held.

Furthermore, the width of the hair band 600 has a value smaller than the distance between the straight line connecting "F3" and "P3" and the straight line connecting "F4" and "P4" in the international 10-20 system, and, preferably, is equal to or less than 25 mm.

For this reason, in the hair band 600, a migraine or discomfort due to a subject lying down is greatly relieved, the pressing amount to the nerve, the blood vessel system, the lymph system, and the muscle system is suppressed to the minimum, and the migraine or discomfort due to the mounting is greatly relieved.

As another example, the hair band 700 shown in FIGS. 40A to 40D can be applied. The hair band 700 is configured so that the center of one wire-shaped tube member portion is bent, and includes a tube member portion (hereinafter, also referred to as a first tube member portion) 710 from the bent end to one open end, and a tube member portion (hereinafter, also referred to as a second tube member portion) 720 from the bed end to the other open end.

The first tube member portion 710 and the second tube member portion 720 are formed in the same C shape, respectively, and in the middle position having the same distance from the respective open ends, members (hereinafter, also referred as tube member holding portions) 730 and 740 are mounted which hold one tube member in a parallel relationship.

The first tube member portion 710 and the second tube member portion 720 are formed as rims (jaw contact portions 750) coming into contact with the jaw from the bent end to the first middle portion near the bent end by the tube member holding portion 730. Furthermore, due to the tube member holding portion 740, the rim is parallel like a rail from the first middle position to the second middle position and is divided in a direction separated from each other using the second middle position as the division position.

The division position (the second middle position) is adjacent to the rear (the occiput side) further than the position corresponding to the center ("Cz" position of the international 10-20 system) of the head among the first tube member portion 710 and the second tube member portion

720. When the division position is adjacent to the front (the jaw side) further than the center of the head, the curvature of the skull is different from the curvature of the parietal bone, between the first tube member portion 710 and the second tube member portion 720, a portion from the division position to the open end floats from the surface of the occiput portion. Thus, by making the division position adjacent to the rear (the open end) further than the central position of the head, compared to the case where the division position is adjacent to the front (the bent end) further than the central position of the head, between the first tube member portion 710 and the second tube member portion 720, the fit amount to the occiput portion from the division position to the open end is improved.

In the open ends of the first tube member portion 710 and the second tube member portion 720, portions (hereinafter, also referred to as ridge slope contact portions) 760 and 770 are formed which come into contact with the head side slope portion of the external occiput ridge. The ridge slope contact portions 760 and 770 slope inward from the first tube member portion 710 and the second tube member portion 720 near the ridge slope contact portions 760 and 770. Thus, during mounting, the ridge slope contact portions 760 and 770 are caught in the head side slope portion of the external occiput ridge, and interposition state with the jaw contact portion 750 is held.

As a result, compared to a case where the ridge slope contact portions 760 and 770 are not bent inward from the first tube member portion 710 and the second tube member portion 720, the support to the head portion is strengthened.

Furthermore, stoppers of resin such as a rubber are fitted to the ridge slope contact portions 760 and 770. For this reason, the support to the head portion is further strengthened.

In the case of applying the hair band 700, the front and rear direction of the head portion can be interposed by three points of one point of the jaw in the head portion and two point of the head side slope portion of the external occiput ridge, and the head portion can be supported. Thus, the position deviation of the electrode to the scalp compared to the head band 600 can be reduced.

Furthermore, between the first tube member portion 710 and the second tube member portion 720, the width of the portion aligned from the first middle position to the second middle position in parallel to each other is smaller than the distance between "C3" and "C4" in the international 10-20 system. Moreover, the width from the division position to the head side slope portion of the external occiput ridge is narrow. Thus, in the hair band 700, a migraine or discomfort due to a subject lying down is greatly relieved, the pressing amount to the nerve, the blood vessel system, the lymph system, and the muscle system is suppressed to the minimum, and the migraine or the discomfort due to the mounting is also greatly relieved.

As another example, a hair band 800 shown in FIGS. 41A to 41D can be applied. The hair band 800 is configured such that three sheets materials 810, 820, and 830 formed of water curable resin having a predetermined width are connected in the bent state based on the portion to be brought into contact with the position adjacent to the occiput further than the central position of the head. A jaw contact portion 840 is attached to the tip of the sheet material 810, a ridge slope contact portion 850 is attached to the tip of the sheet material 820, and a ridge slope contact portion 860 is attached to the tip of the sheet material 830, respectively.

The connection portion JP of three sheet materials 810, 820, and 830 becoming the standard the hair band 800 is a portion to be brought into contact with the position adjacent to the occiput but not the position adjacent to the jaw from the central position of the head. Thus, like the case of the hair band 800, compared to the case of making the connection portion adjacent to the jaw further than the central position of the head, the fit amount from the connection portion JP to the ridge slope contact portions 850 and 860 is improved.

Furthermore, in the sheet materials 820 and 830 on which the ridge slope contact portions 850 and 860 are mounted, a region AR2 from the center vicinity to the ridge slope contact portions 850 and 860 enters the inside further than a region AR1 from the center vicinity of the longitudinal direction of the sheet materials 820 and 830 to the connection portion JP. Thus, during mounting, the ridge slope contact portions 850 and 860 are caught in the head side slope portion of the external occiput ridge, and the interposition state with the jaw contact portion 840 is held. As a result, the hair and is fitted compared to the case where the region AR2 from the center vicinity to the ridge slope contact portions 850 and 860 does not enter the inside further than the region AR1 from the center vicinity to the connection portion JP, whereby the support to the head portion is strengthened.

In the case of applying the hair band 800, like the case of applying the hair band 700, since the front and rear direction of the head portion is interposed by three points of one point of the jaw in the head portion and two points of the head side slope portion of the external occiput ridge and the head portion can be supported, the position deviation of the electrode to the scalp is reduced.

Furthermore, the width of the sheet material is smaller than the distance between "C3" and "C4" in the international 10-20 system. Thus, in the hair band 800, like the hair band 700, a migraine or discomfort due to a subject lying down is greatly relieved, the pressing amount to the nerve, the blood vessel system, the lymph system, and the muscle system is suppressed to the minimum, and the migraine or discomfort due to the mounting is greatly relieved.

Furthermore, since the hair band 800 is formed of water curable resin, the hair band can be disposable, and is desirable in view of the low cost or ease of handling.

Figure 42:
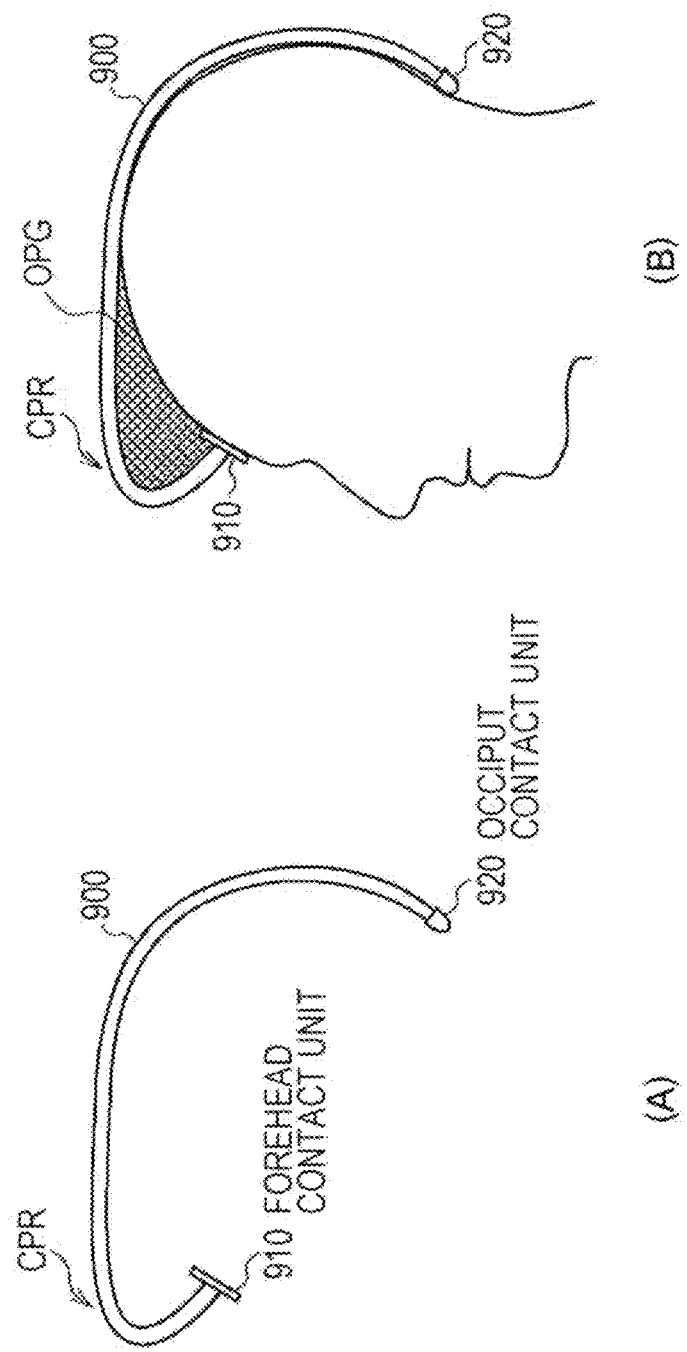
FIGS. 42A and 42B are diagrams that schematically show a hair band and a mounting state thereof in another embodiment.

As another example, a hair band 900 shown in FIGS. 42A and 42B can be applied. Stoppers of resin such as a rubber are fitted to both ends of the hair band 900 and are formed as a jaw contact portion 910 and an occiput contact portion 920. The hair band 900 is a wire-shaped tube member and is formed on any character.

That is, the hair band 900 is asymmetrical (front and rear asymmetry) based on the position to be brought into contact with the vertex, and is common to the hair band 600 shown in FIGS. 39A to 39C due to the fact that the occiput contact portion 920 is in a lower positional relationship compared to the jaw contact portion 910 during mounting.

However, the hair band 900 is extended over the jaw contact portion 910 from the position to be brought into contact with the vertex in a straight line manner, and is sharply bent inward (the occiput contact portion 920 side) in the contact vicinity portion CRP with the jaw contact portion 910. This point is different from the hair band 600 that is bent along the head portion shape from the position to be brought into contact with the vertex over the jaw contact portion 610.

Thus, in the hair band 900, the portion coming into contact with the head portion during mounting becomes only a part (as shown in FIGS. 42A and 42B, a portion excluding the gap OPG of the front of the head portion) of the outline passing through the medial sagittal plane in two points of the forehead and the occiput. For this reason, in the hair band 900, compared to the hair band 2, the hair band 600 or the like of the biological signal measuring equipment 60, the pressing to the head portion due to the weight of the head portion itself is reduced. As a result, a migraine or discomfort due to the mounting is greatly relieved.

Furthermore, the width of the hair band 900 has a value smaller than the distance between the straight line connecting "F3" and "P3" in the international 10-20 system and the straight line connecting "F4" and "P4", and, preferably, is equal to or less than 25 mm.

For this reason, in the hair band 900, the migraine or the discomfort due to the lying of a subject is greatly relieved, the pressing amount to the nerve, the blood vessel system, the lymph system, and the muscle system is suppressed to the minimum, and the migraine or the discomfort due to the mounting is also greatly relieved.

Figure 43:
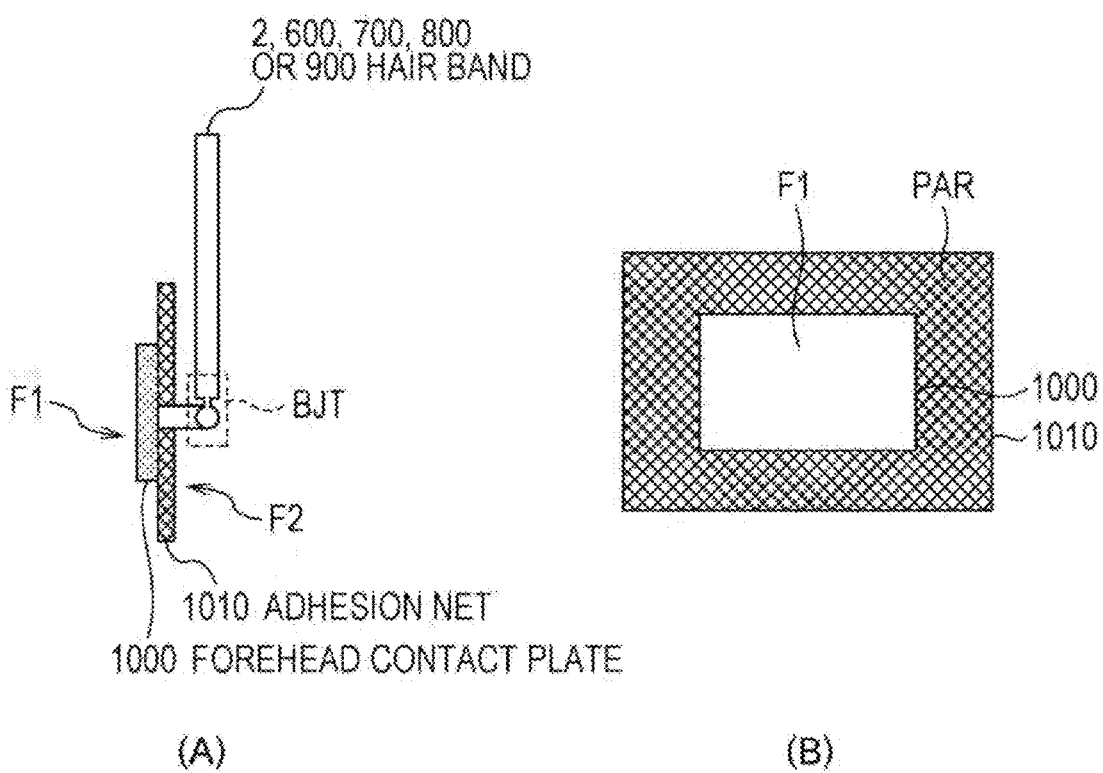
FIGS. 43A and 43B are diagrams that schematically show a structure of a jaw contact portion in another embodiment.

As the structure of the portion coming into contact with the jaw in the hair band 2, 600, 700, 800 or 900, a structure shown in FIG. 43 can be applied.

That is, the tip of the hair band 2, 600, 700, 800 or 900 and a plate member (hereinafter, also referred to as a jaw contact plate) 1000 to be brought into contact with the jaw are connected to each other by a ball type joint BJT.

The ball type joint BJT includes a ball-like convex stud, and a concave stud fitted to the ball portion of the convex stud in a freely slidable manner as components. The components are fixed to any one of the tip of the hair band (2, 600, 700, 800 or 900) or the jaw contact plate 1000.

In the liquid contact plate 1000, on the rear surface F2 of a side opposite to the surface F1 to be brought into contact with the jaw, a mesh-like member (hereinafter, also referred to as an adhesion net) 1010 having stickiness is mounted. The adhesion net 1010 has an area greater than the surfaces F1 and F2 of the jaw contact plate 1000, and a region (half-tone portion of FIG. 43B) other than the region to be attached to the surface F2 is a region (hereinafter, also referred to as a jaw sticking region) PAR to be stuck to the claw.

That is, the portion (the surface F1) coming into contact with the jaw and the stuck portion (the jaw sticking region PAR) are separated from each other, and the surface F1 is stuck to the jaw so as to be covered from the rear side.

Thus, compared to the case where the surface F1 itself to be brought into contact with the jaw is formed of an adhesion sheet, even when there is a change in jaw surface such as a wrinkle generated when the face frowns, the deviation of the portion (the surface F1) coming into contact with the jaw is reduced.

Furthermore, the jaw contact plate 1000 is connected to the hair band (2, 600, 700, 800 or 900) via a mobile portion (the ball type joint BJT). Thus, force added to the jaw contact plate 1000 or the adhesion net 1010 by the change in jaw surface is absorbed in the ball type joint BJT. As a result, compared to a case where the portion between the jaw contact plate 1000 and the hair band is immovable, the deviation of the jaw contact plate 1000 due to the change in jaw surface or the fall-out of the adhesion net 1010 is reduced.

In addition, the adhesion net 1010 is formed of a mesh shape and is formed as the state having a regular elasticity, and thus, compared to the case of using the adhesion material of a simple sheet shape, the deviation of the jaw contact plate 1000 due to the change in jaw surface or the fall-out of the adhesion net 1010 is reduced.

In addition, the jaw contact plate 1000 is formed of an electrode, and like the electrode contact detection treatment in the analyzing portion 34 mentioned above, the presence or the absence of the contact of the jaw contact plate 1000 to the forehead may be determined.

Figure 44:
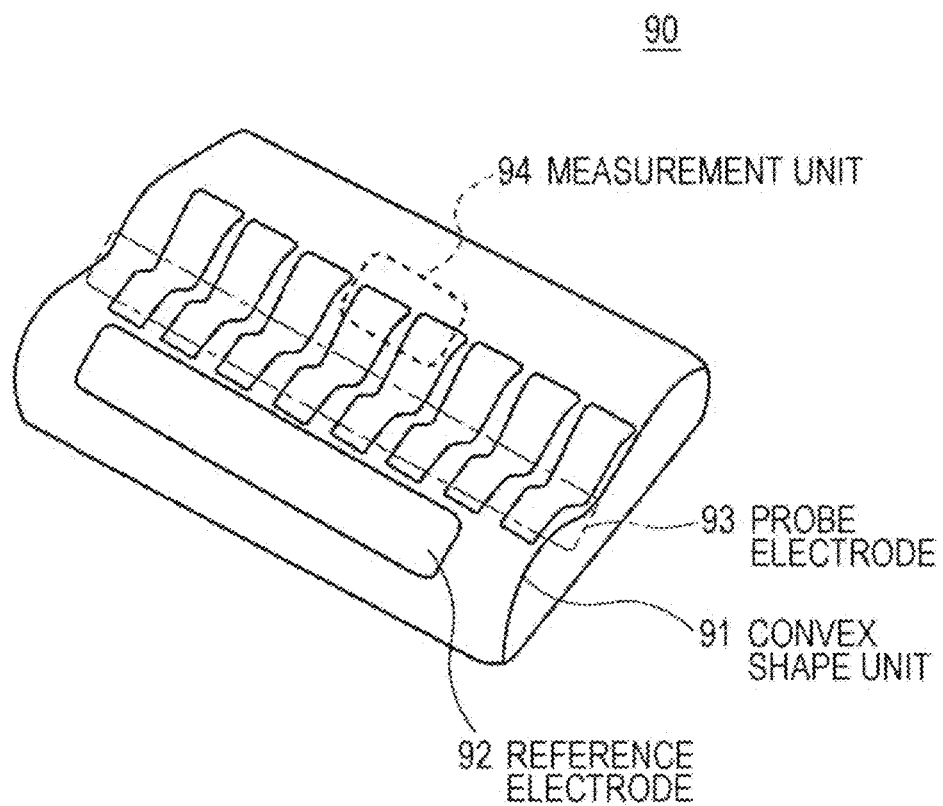
FIG. 44 is a diagram that schematically shows a configuration of a biological signal measuring pillow.

Instead of the pieces of biological signal measuring equipment 1, 50, and 60, the head brace 300 or the jaw brace 500 in the first to third embodiments mentioned above, a biological signal measuring pillow 90 shown in FIG. 44 can also be applied.

The biological signal measuring pillow 90 has a structure including a part 91 (hereinafter, also referred to as a convex shape portion) in which one end is ridged in a convex shape compared to the other end so as to be fitted together with the head. On the slope surface of the side opposite to the slope facing the other end of the slope in the convex shape portion 91, a sheet-shaped reference electrode 92 is provided.

Meanwhile, among the surface in the biological signal measuring pillow 90, in the region of the root of the slope facing the other end in the convex shape portion 91 and the predetermined position from the root to the other end, a plurality of probe electrodes 93 having a plate shape is arranged at equal intervals. Furthermore, in the inner portion of the biological signal measuring pillow 90, a measurement portion 94 is provided which measures the potential difference between the probe electrode 93 and the reference electrode 92. As the measurement portion 94, the measurement portion mentioned in the first embodiment or the third embodiment can be applied.

According to the biological signal measuring pillow 90, since the mounting of the tool is not forced to a subject, the burden on a subject can be reduced. Furthermore, since the reference electrode 92 and the probe electrode 93 can be pressed to the head, surface, and the scalp by the weight of the subject itself, uniform measurement sensitivity can be ensured.

Furthermore, the structure of the biological signal measuring pillow 90 is not limited to one shown in FIG. 44, but, for example, it is possible to apply various structures such as a structure having a concave middle or a structure having a middle ridged in a convex shape.

Furthermore, the arrangement shape of the probe electrode 92 is also not limited to the shape shown in FIG. 44. For example, as shown in FIG. 45, a plurality of electrodes formed in a line shape may be arranged in a row or column direction at equal intervals (FIG. 45A), may be arranged in the row and column direction at equal intervals (FIG. 45B), and may be radially arranged (FIG. 45C).

Figure 46:
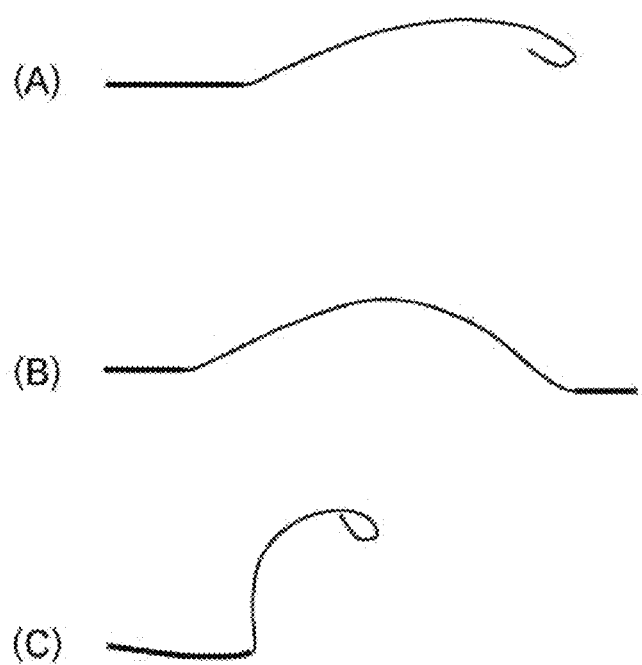
FIGS. 46A to 46C are diagrams that schematically show a shape of an electrode of another embodiment.

Furthermore, the shape of the probe electrode 92 is also not limited to the shape shown in FIG. 43. For example, as shown in FIGS. 46A to 46C, a comb shape may be adopted (FIG. 46A), a mountain shape may be adopted (FIG. 46B), and a pistil shape may be adopted (FIG. 46C). In addition, the thick line in FIGS. 45A to 45C indicates the fixing part. Furthermore, the electrode shapes can be applied as the shapes of teeth that configure the probe electrodes 13 and 55 or the reference electrode 12.

Figure 47:
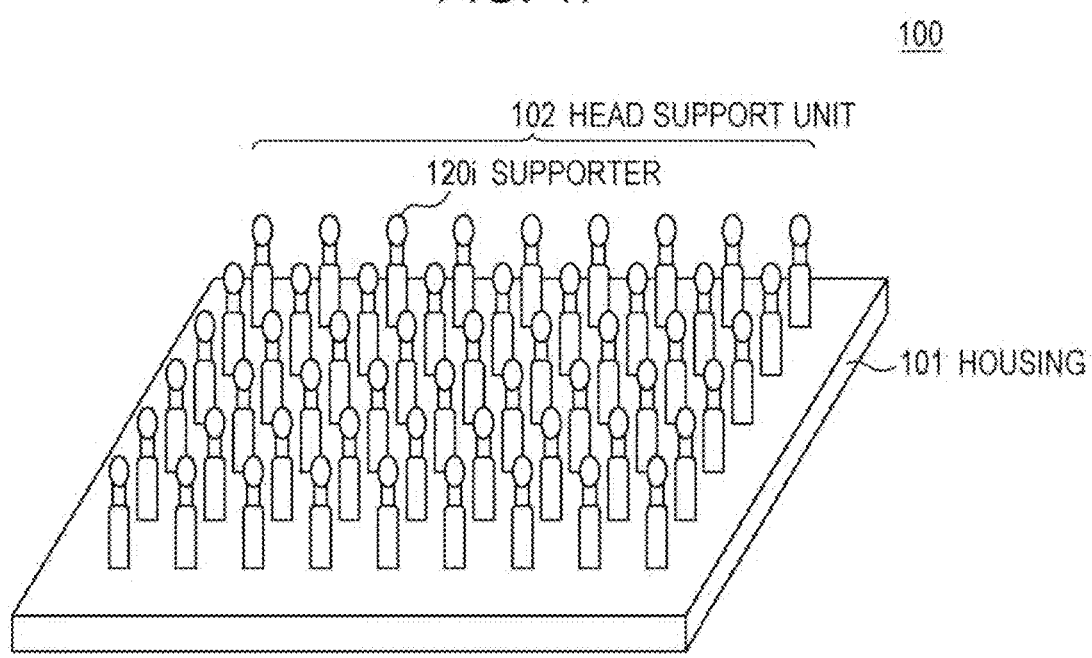
FIG. 47 is a diagram that schematically shows a configuration of a biological signal measuring pillow.

Furthermore, instead of the biological signal measuring pillow 90, a biological signal measuring pillow 100 shown in FIG. 47 can be applied. The biological signal measuring pillow 100 has a sheet-shaped case 101 and a portion 102 (hereinafter, also referred to as a head support portion) supporting the head.

The case 101 is formed of a non-conductive material, and one surface in the case 101 is a pedestal on which the head support portion 102 is installed.

Figure 48:
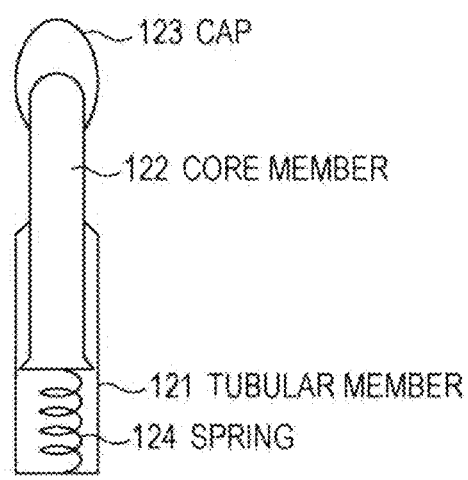
FIG. 48 is a diagram that schematically shows a configuration of a supporter.

The head support portion 102 has a structure in which a plurality of supporters $120_i$ (i=2, 3, . . . , or m (m is an integer) is arranged in the column direction and the row direction at equal intervals. As shown in FIG. 48, the supporter $120_i$ has a conductive tubular-shaped member 121, and a conductive tubular-shaped core member 122 that is inserted into the hollow of the tubular-shaped member 121 in a freely slidable manner. A round conductive cap 123 having flexibility is attached to one end of the core member 122, and a conductive spring 124 is attached to the other end thereof. Specifically, for example, a conductive rubber or the like can be applied as the cap 123.

When the head portion is in the head support portion 102 for sleeping, the core members 122 of each of the supporters $120_i$ smoothly slides in the hollow of the tubular-shaped member 121 due to gravity (weight of the supporters themselves) added to the part of the corresponding head portion and the elasticity of the spring 124 to be attached to the other end of the core member 122.

Figure 49:
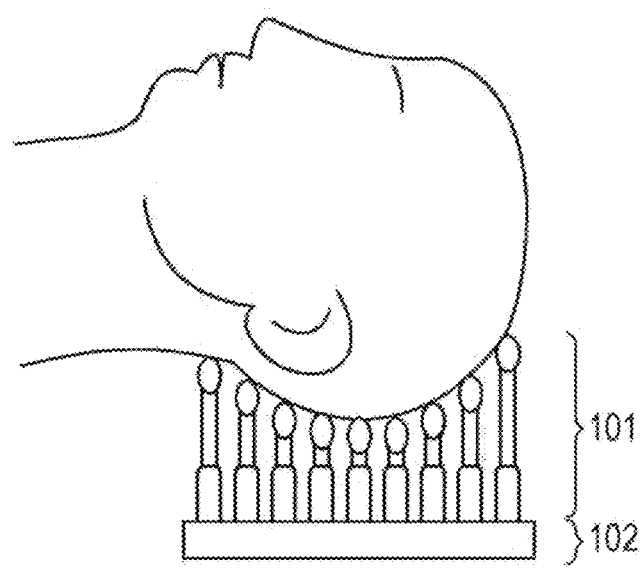
FIG. 49 is a diagram that schematically shows a sleep state.

Thus, as shown in FIG. 49, the head support portion 102 can fit each supporter $120_i$ to the shape of the head portion regardless of the individual variation and can relieve the impact when putting the head portion on the head support portion 102. In addition, since the adhesion of the cap 123 to the scalp is improved compared to the biological signal measuring pillow 90, the measurement sensitivity is improved.

Furthermore, since the rounded cap 123 having flexibility is attached to one end of the core member 122, when the head portion is in the head support portion 102, the pain of the contact portion on the head portion is relieved.

In addition, the supporters $120_i$ can be applied as the teeth that constitute the probe electrodes 13, 55, 320A, 320B, 400A, 400B, 510A, and 510B, the reference electrodes 57C, 77, 370A, and 370B or the reference electrode 12. Furthermore, the supporters can also be replaced with the shape shown in FIGS. 46A to 46C. Additionally, the supporter $120_i$ can also be applied to the conductive fiber 321 mentioned above.

Figure 50:
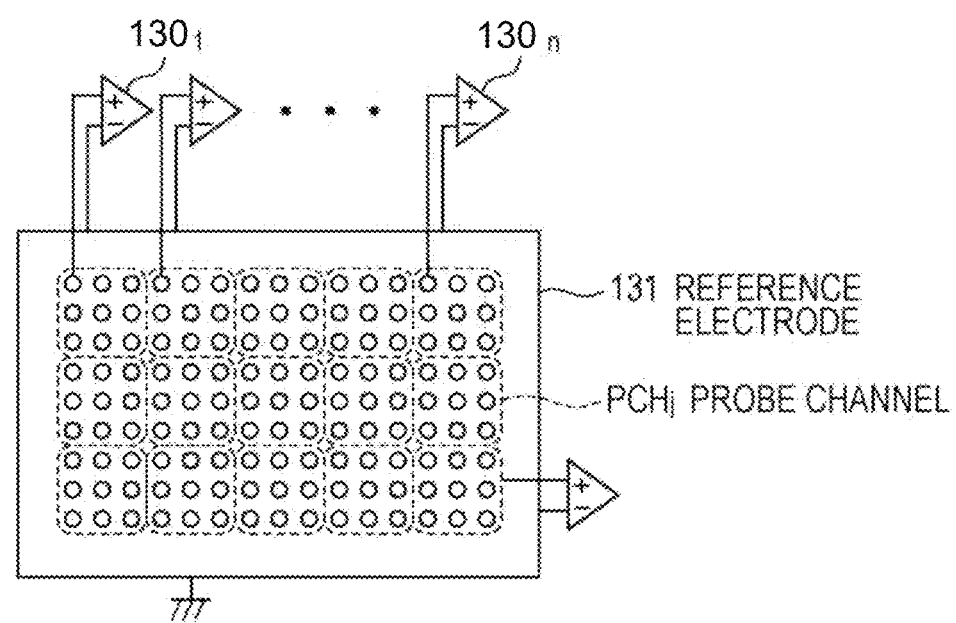
FIG. 50 is a schematic diagram that is provided in the description of an allocation of a probe channel.

Meanwhile, each supporter $120_i$ is also used as the probe electrode. As shown in FIG. 50, in the biological signal measuring pillow 100, supporters of x column×y row are allocated as the probe channel $PCH_j$ (j=2, 3, . . . , or n (n is an integer)).

The supporter constituting the probe channel $PCH_j$ is connected to one input end in the corresponding amp 130, and the reference electrode 131 is connected to the other input end in the amp 130. The amp 130 and the reference electrode 131 are stored in the inner portion of the case 101.

Figure 51:
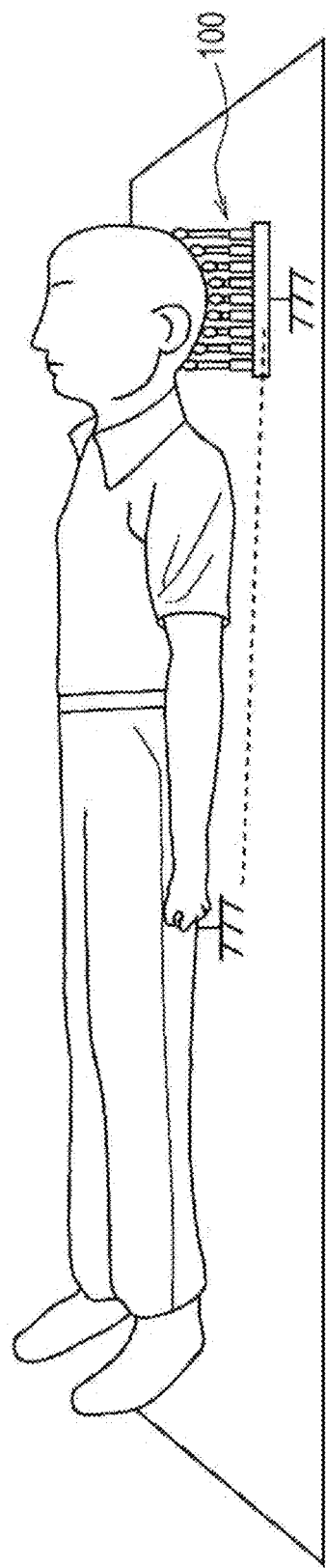
FIG. 51 is a diagram that schematically shows a grounded state of a biological signal measuring pillow.

In addition, as shown in FIG. 51, the biological signal measuring pillow 100 is grounded to a human body or via a blanket covering the human body, and is not physically grounded.

Figure 52:
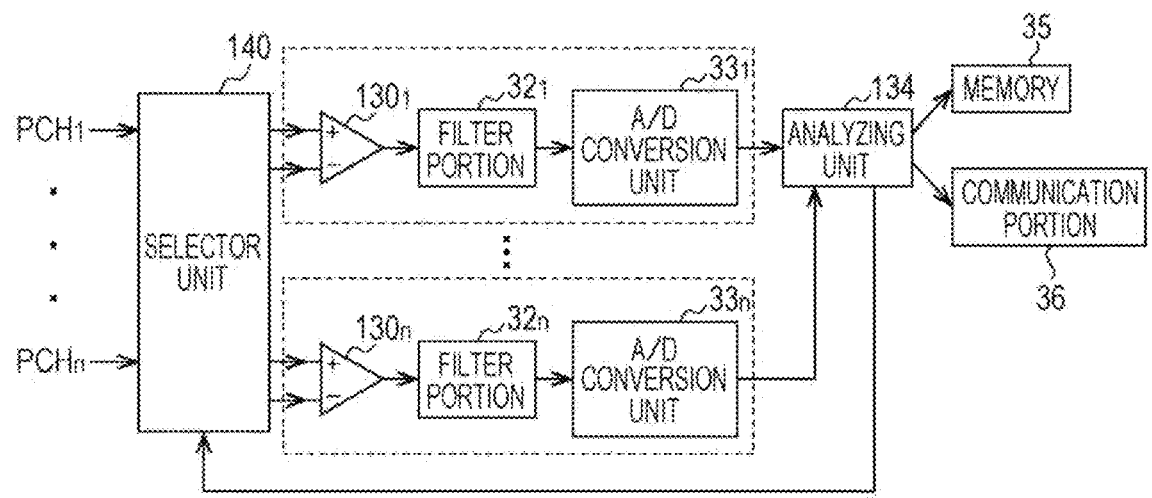
FIG. 52 is a diagram that schematically shows a configuration of a measurement portion in another embodiment.

Herein, the configuration of the measurement portion stored in the inner portion of the case 101 is shown in FIG. 52 in which the portions corresponding to FIG. 4 are denoted by the same reference numerals. The measurement portion is different from the measurement portion shown in FIG. 4 in that it newly has a function of selecting the probe channel to be sensed from the probe channel $PCH_j$. Specifically, an analyzing portion 134 is adopted in which a new treatment is added to the treatment in the analyzing portion 34, and a selector portion 140 is newly provided.

A difference of the total potential obtained from the supporters constituting the probe channel $PCH_j$ to the reference electrode 131 is amplified for each probe channel $PCH_j$, and the difference is input to the analyzing portion 134 sequentially via the corresponding filter portion $32_j$ and the A/D conversion portion $33_j$ as the biological signal.

Figure 53:
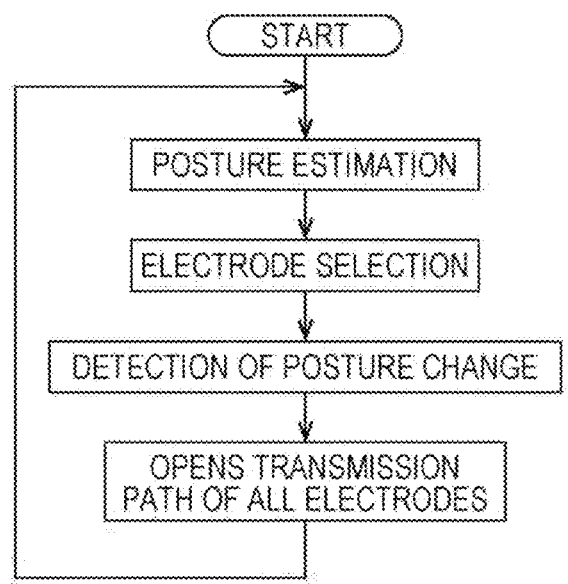
FIG. 53 is a flowchart that shows an electrode selection treatment sequence.

The analyzing portion 134 executes the same treatment as mentioned in the analyzing portion 34 using the biological signals, and, for example, executes the selection treatment of the electrode (the probe channel) according to the flowchart shown in FIG. 53.

That is, the analyzing portion 134 assumes the state of an object (a head portion) to the head support portion 102 as a first step. The parameter (the assumption element) necessary for the assumption is, for example, a level of the biological signal in a unit time zone among the biological signal corresponding to each probe channel $PCH_j$, and position information to which the probe channel $PCH_j$ is allocated.

The analyzing portion 134 detects the probe channel $PCH_j$ to be selected based on the assumption result of the state (the posture) of the object (the head portion) to the head support portion 102, as a second step, and gives the selector portion 140 the selection command corresponding to the detection result. Specifically, for example, the probe channel $PCH_j$ other than the probe channel $PCH_j$ corresponding to the position, where the level of the biological signal is less than a predetermined value, is a probe channel $PCH_j$ to be selected. Thus, in the selector portion 140, the transmission path of the probe channel $PCH_j$ corresponding to the position, where the level of the biological signal is less than the predetermined value, is cut off, and, as a result, the transmission path of only the probe channel $PCH_j$ is selected in which the head portion is punt on the head support portion 102.

The analyzing portion 134 detects a change in state (posture) of the object (the head portion) to the head portion 102 based on the biological signal corresponding to the probe channel $PCH_j$ selected at the second step, as a third step. The parameter (the detection element) necessary for the detection is a rate of reduction of the level per unit time in the biological signal, and the number of the biological signal greater than the threshold vale to be set to the rate of reduction. In this example, when, among the biological signals corresponding to the probe channel $PCH_j$ selected at the second step, the biological signal having the rate of reduction greater than the threshold value exceeds a predetermined number, the posture of the head portion, which is in the head support portion 102, is changed.

When the change in state (posture) of the object (the head portion) to the head support portion 102 is detected, the analyzing portion 134 gives the command, which needs to open the transmission paths of the whole probe channels $PCH_j$, to the selector portion 140, as a fourth step, and then, the analyzing portion 134 executes each treatment from the first step to the third step.

In this manner, the analyzing portion 134 executes the selection treatment of the electrode (the prove channel).

Figure 54:
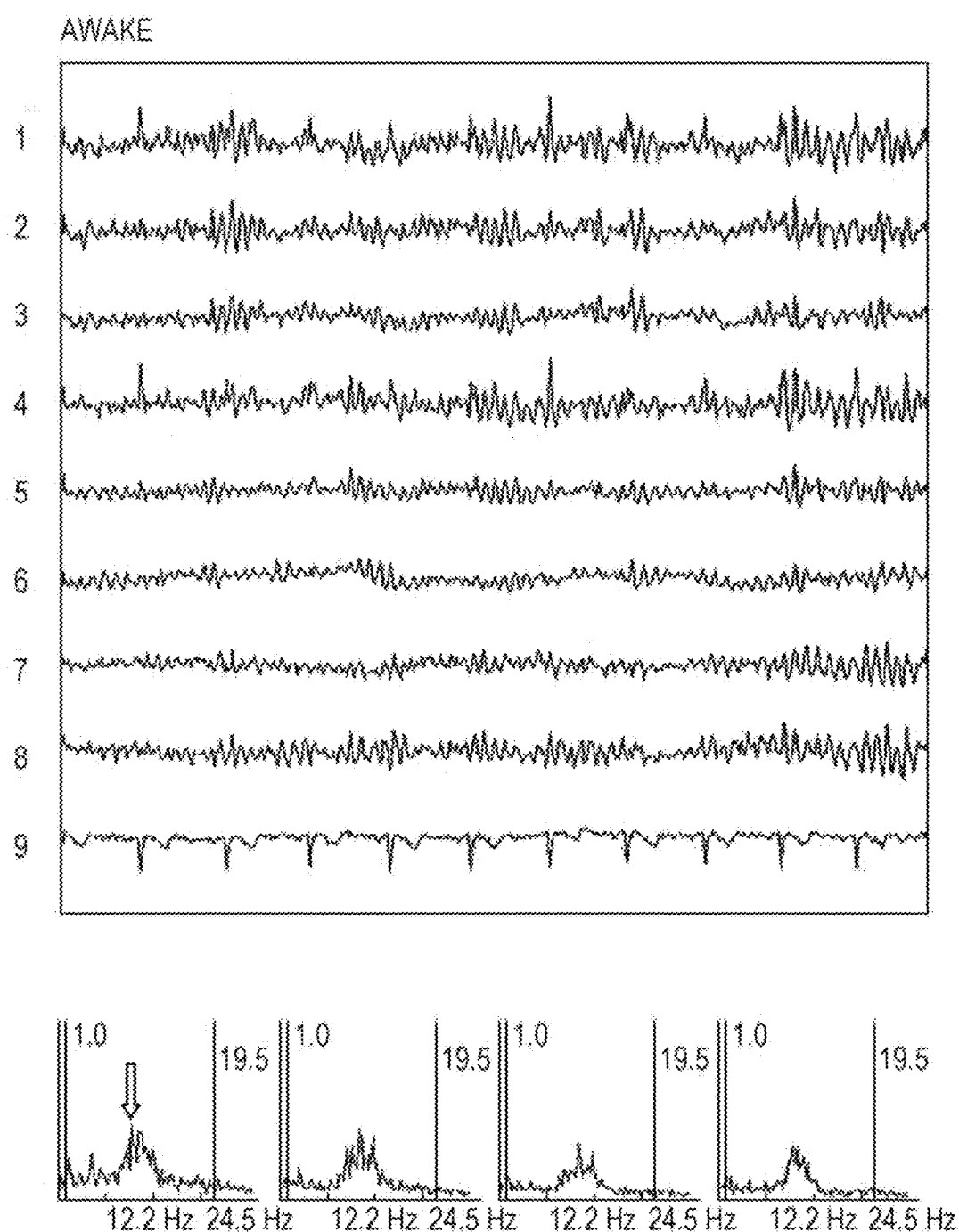
FIG. 54 is a graph that shows a test result.
Figure 55:
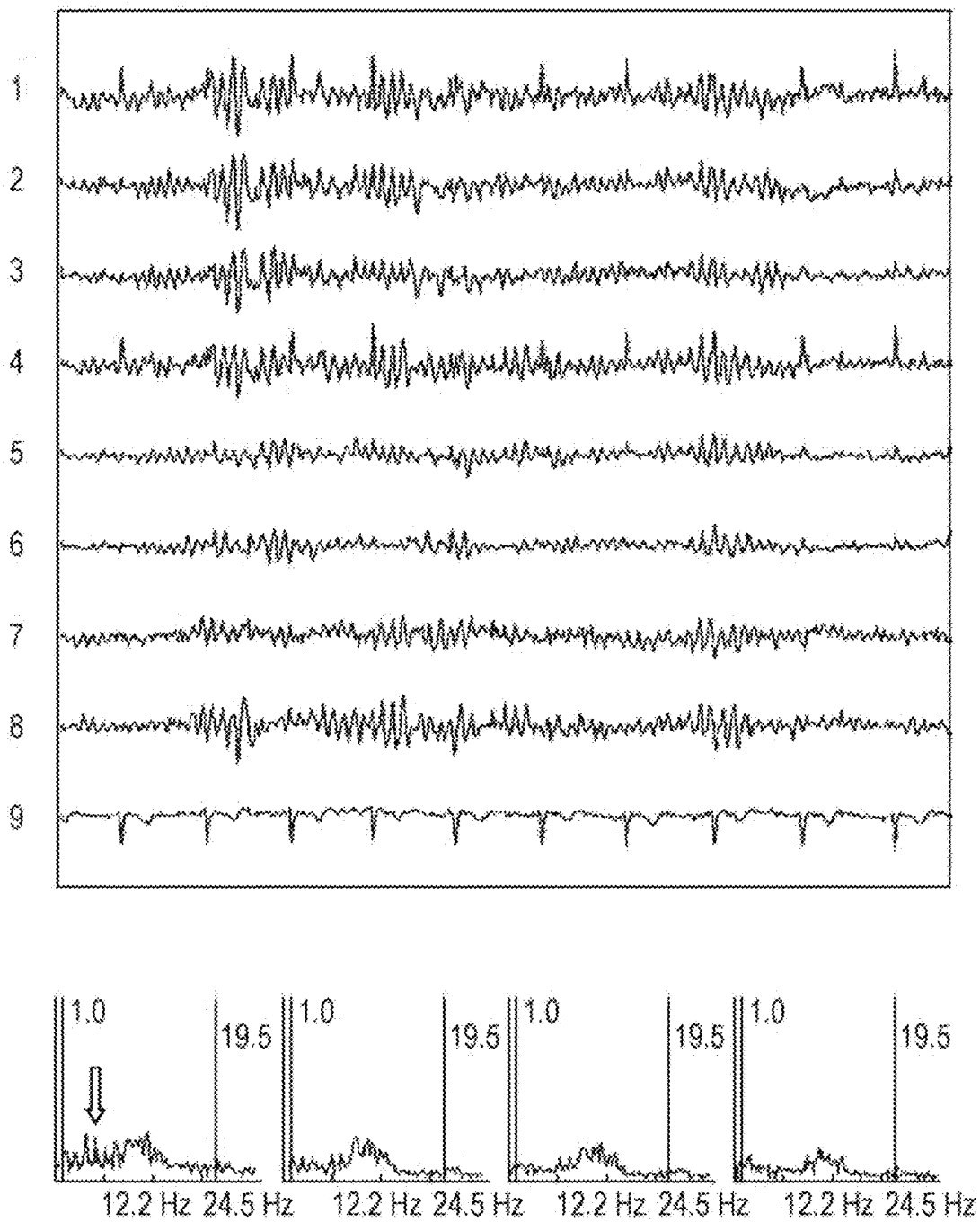
FIG. 55 is a graph that shows the test result.
Figure 56:
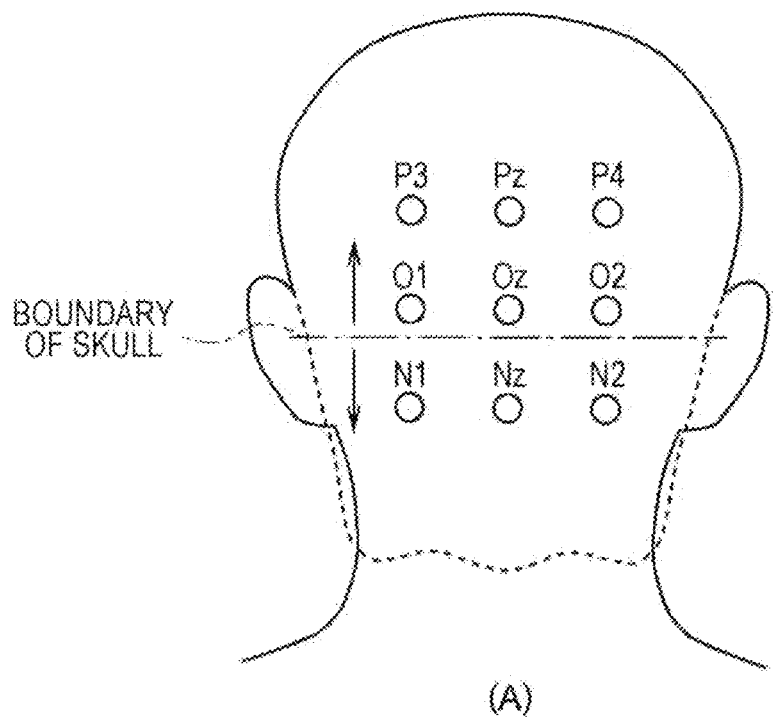
FIGS. 56A and 56B are diagrams that schematically show an electrode arrangement during the test.

In addition, the test result, in which the biological signal measuring pillow 100 is assumed, is shown in FIGS. 54 and 55, and the electrode arrangement in the test is shown in FIG. 56. As is apparent from the test result, the biological signal was observed by the measurement sensitivity having no substantial problem.

INDUSTRIAL APPLICABILITY

The present invention can be applied to the medical industry, the game industry or the like.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A biological signal measuring equipment, comprising:
a supporter including:
an arm;
a forehead contact portion configured to come into contact with a forehead of a head portion;
an occiput contact portion configured to come into contact with an occiput of the head portion; and
a fixing region, connected to the forehead contact portion,
wherein the supporter is configured to be positioned between the forehead contact portion and the occiput contact portion when the supporter is arranged on the head portion;
an attachment opening present in the fixing region and configured to attach the arm that extends from the supporter in a freely attachable and detachable manner;
a first electrode attached to a portion of the supporter situated on a median sagittal plane of the supporter;
a second electrode configured to be positioned at an earlobe and attached to the arm;
a plurality of magnets, wherein the plurality of magnets and the second electrode are configured to affix to the earlobe so that the earlobe is interposed between the plurality of magnets and the second electrode;
a case that protrudes from the supporter at the fixing region; and
an electronic device configured to interface with the first electrode and the second electrode.

2. The biological signal measuring equipment of claim 1, wherein the electronic device includes an analog-based electronic circuit, which is present at the fixing region on the supporter, and a digital-based electronic circuit.

3. The biological signal measuring equipment of claim 1, further comprising:
a plurality of amplification portions that are present at the fixing region on the supporter,
wherein the plurality of amplification portions corresponds to the first electrode and the second electrode, and
wherein a ground of the plurality of amplification portions is concentrated at the fixing region on the supporter.

4. The biological signal measuring equipment of claim 1, further comprising:
a measurement portion configured to measure a potential difference between the first electrode and the second electrode as a biological signal of the head portion,
wherein the measurement portion is further configured to measure a level in biological signals for each of a plurality of periods and compare an average of the level in the biological signals for each of the plurality of periods with a threshold value, and based on a determination that the average is lower than the threshold value, the measurement portion is further configured to notify, via a speaker, that the first electrode and the second electrode need to be remounted.

5. The biological signal measuring equipment of claim 1, wherein the supporter further comprises a supporter portion situated on the median sagittal plane of the supporter, and a pair of branching portions branched from the supporter portion, wherein the occiput contact portion comprises a first occiput contact portion which is configured to contact a first neck side slope portion of a right side external occiput ridge and a second occiput contact portion which is configured to contact a second neck side slope portion of a left side external occiput ridge, and
wherein the first occiput contact portion is connected to a first one of the pair of branching portions as a first rear end, and
wherein the second occiput contact portion is connected to a second one of the pair of branching portions as a second rear end.

6. The biological signal measuring equipment of claim 5, wherein a position on the supporter portion from which the pair of branching portions is branched is a position nearer an occiput side of the head portion than a forehead side of the head portion from a center of the head portion.

7. The biological signal measuring equipment of claim 1, further comprising:
a plurality of grooves on the supporter at regular intervals in a lengthwise direction of the supporter; and
an adjuster section configured to slide in a lengthwise direction of the supporter,
wherein a portion of an inner surface of the adjuster section that faces the plurality of grooves has a claw configured to fit in each of the plurality of grooves.

8. The biological signal measuring equipment of claim 1, wherein the fixing region is positioned closer to the forehead contact portion than the occiput contact portion.

* * * * *